(12) United States Patent
Cossío Mora et al.

(10) Patent No.: US 8,685,992 B2
(45) Date of Patent: Apr. 1, 2014

(54) HISTONE DEACETYLASE INHIBITORS BASED SIMULTANEOUSLY ON TRISUBSTITUTED 1H-PYRROLES AND AROMATIC AND HETEROAROMATIC SPACERS

(75) Inventors: Fernando Pedro Cossío Mora, Donostia-San Sebastián (ES); Aizpea Zubia Olascoaga, Donostia-San Sebastián (ES); Yosu Vara Salazar, Donostia-San Sebastián (ES); Eider Ion San Sebastián Larzabal, Donostia-San Sebastián (ES); Dorleta Otaegui Ansa, Donostia-San Sebastián (ES); María del Carmen Masdeu Margalef, Donostia-San Sebastián (ES); Eneko Aldaba Arévalo, Donostia-San Sebastián (ES)

(73) Assignees: Universidad del País Vasco, Leioa-Vizcaya (ES); Ikerschem, S.L., Donostia-San Sebastian (ES)

( * ) Notice: Subject to any disclaimer, the term of this patent is extended or adjusted under 35 U.S.C. 154(b) by 0 days.

(21) Appl. No.: 13/499,839

(22) PCT Filed: Oct. 1, 2010

(86) PCT No.: PCT/EP2010/064653
§ 371 (c)(1),
(2), (4) Date: Apr. 2, 2012

(87) PCT Pub. No.: WO2011/039353
PCT Pub. Date: Apr. 7, 2011

(65) Prior Publication Data
US 2012/0196885 A1    Aug. 2, 2012

(30) Foreign Application Priority Data
Oct. 2, 2009   (EP) .................................... 09382193

(51) Int. Cl.
*A01N 43/54*    (2006.01)
*A61K 31/505*   (2006.01)

(52) U.S. Cl.
USPC ........... 514/275; 514/408; 514/422; 514/343; 544/331; 546/279.1; 548/517; 548/519; 548/537

(58) Field of Classification Search
USPC .......... 514/275, 422, 343, 423; 548/517, 537, 548/532; 546/279.1; 544/331
See application file for complete search history.

(56) References Cited

U.S. PATENT DOCUMENTS

2005/0154042 A1* 7/2005 Bratton et al. ................. 514/408

FOREIGN PATENT DOCUMENTS

| WO | 2005028447 A1 | 3/2005 |
|----|---------------|--------|
| WO | 2006108864 A2 | 10/2006 |
| WO | 2007074176 A1 | 7/2007 |

OTHER PUBLICATIONS

A.M. Traynor et al., Drugs of Today, 40(8), 697-710 (2004).*
S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
M. Kobel et al., PLoS Medicine, 5(12) 1749-1760 (2008).*
A.J. Tiltman, Best Practice & Research Clinical Obstetrics & Gynaecology, 485-500, 19(4) (2005).*
J. L. Raizer, Journal of Neuro-Oncology, 74(1), 77-86 (2005).*
R.G.W. Verhaak et al., Cancer Cell, 17(1), 1-24 (2010).*
S.K. Libutti, Colon Cancer in, 1 Cancer Principles & Practice of Oncology 1232, 1243 (V.T. DeVita, Jr. et al. eds., 8th ed., 2008).*
L. Pusztai, Histopathologic and Molecular Markers of Prognosis and Response to Therapy, in Breast Cancer 324, 326-328 (Kelly k. Hunt et al., ed., 2nd ed., 2008).*

(Continued)

*Primary Examiner* — James O Wilson
*Assistant Examiner* — Alexander R Pagano
(74) *Attorney, Agent, or Firm* — Tristan A. Fuierer; Moore & Van Allen, PLLC

(57) ABSTRACT

The present invention refers to compounds derived from trisubstituted 1H-pyrrole rings and aromatic rings, which have the following formula (I):

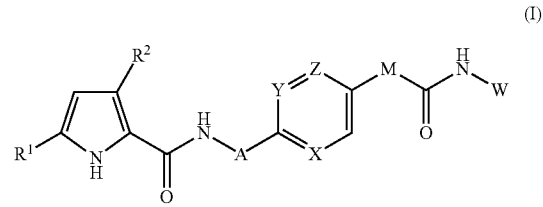

(I)

wherein:
  $R^1$ and $R^2$ represent, independently, an optionally substituted $C_6$-$C_{10}$ aryl radical or an optionally substituted heteroaryl radical;
  A and M represent, independently, a methylene group or a single bond, in which case the adjacent aromatic ring would be attached directly to the amide group;
  the Y=Z group represents together and indistinctly an oxygen atom, a sulfur atom, a cis-vinylidene group, an imino group, or a methine group with a $sp^2$-hybridized carbon atom;
  X represents indistinctly a methine group, a cis-vinylidene group or a nitrogen atom; and
  W represents a hydroxyl group, an optionally substituted $C_1$-$C_6$ alkyl group, an optionally substituted heteroaryl group or an optionally substituted $C_6$-$C_{10}$ aryl group;
or a salt, solvate or prodrug thereof,
as well as to the process for their preparation and the use thereof for the treatment of cancer.

23 Claims, No Drawings

(56) References Cited

OTHER PUBLICATIONS

D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
F.F. De Arruda, et al., Int. J. Radiation Oncology Biol. Phys., 64(2), 363-373 (2006).*
B.C. Bastian, Genetic Progression, in From Melanocytes to Melanoma the Progression to Malignancy 197, 201 (V. J. Hearing et al., eds., 2006).*
J. Tsai et al., 105 PNAS 3041-3046, 3041 (2008).*
T. Carling et al., Thyroid Tumors in, 2 Cancer Principles & Practice of Oncology 1503 (V.T. DeVita, Jr. et al. eds., 8th ed., 2008).*
B Testa et al., Prodrug Design in, 5 Encyclopedia of Pharmaceutical Technology, 3008-3014 (J. Swarbrick ed., 3rd ed., 2007).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
K. Odunsi et al, Molecular Biology of Gynecological Cancers, in 2 Cancer Principles & Practice of Oncology 1487, 1492 (V.T. DeVita, Jr. et al. eds., 8th ed., 2008).*
J.E. Bolden et al., 5 Nature Reviews Drug Discovery, 769-784 (2006).*
M. Dokmanovic et al., 5 Molecular Cancer Research, 981-989 (2007).*
W. Weichert, 280 Cancer Letters, 168-176 (2009).*
A. Kamb, Nature Reviews Drug Discovery 2, 161-165 (2005).*
N.E. Sharpless et al., Nature Reviews Drug Discovery 5, 741-754, 742 (2006).*
K.P. Olive et al., Clinical Cancer Research 12, 5277-5287 (2006).*
A-M Bleau et al., 8 Cell Cycle 2937-2945 (2009).*
Marks, P.A. et al.; "Histone Deacetylases and Cancer:Causes and Therapies," Nature Review Cancer, 2001, pp. 194-203, vol. 1.
Bolden J.E., et al., "Anticancer activities of histone deacetylase inhibitors," Nature Review Drug Discovery, 2006, pp. 769-785, vol. 5.
Gallinari, P., et al.; "HDACs, histone deacetylation and gene transcription: from molecular biology to cancer therapeutics," Cell Research., 2007, pp. 195-211, vol. 17.
Glaser, K.B.; "HDAC inhibitors: Clinical update and mechanism-based potential," Biochemistry Pharmacology, 2007, pp. 659-670, vol. 74.
Pan, L., et al.; "HDAC Inhibitors: A Potential new Category of Anti-Tumor Agents," Cellular & Molecular Immunology, 2007, pp. 337-343, vol. 4.
Haberland, M., et al.; "The many roles of histone deacetylases in development and physiology: implications for disease and therapy," Nature Review Genetics, 2009, pp. 32-42, vol. 10.
Zhang, Y., et al.; "The Structure and Function of Histone Deacetylases: The Target for Anit-cancer Therapy," Current Medicinal Chemistry, 2008, pp. 2840-2849, vol. 15.
Ropero, S., et al.; "The role of histon deacetylases (HDACs) in human cancer," Molecular Oncology, 2007, pp. 19-25, vol. 1.
Kazantsev, A.G., et al.; "Therapeutic application of histone deacetylase inhibitors for central nervous system disorders," Nature Review Drug Discovery, 2008, pp. 854-869, vol. 7.

Villar-Garea, A., et al.; "Histone Deacetylase Inhibitors: Understand a New Wave of Anticancer Agents," Int. Journal of Cancer, 2004, pp. 171-178, vol. 112.
Miller, T.A., et al.; "Histone Deacetylase Inhibitors," Journal of Medicinal Chemistry, 2003, pp. 5097-5116, vol. 46.
Suzuki, T., et al.; "Non-hydroxamate Histone Deacetylase Inhibitors," Current Medicinal Chemistry, 2005, pp. 2867-2880, vol. 12.
Paris, M., et al.; "Histone Deacetylase Inhibigots: From Bench to Clinic," Journal of Medicinal Chemistry, 2008, pp. 1505-1529, vol. 51.
Wong, J.C., et al.; "Structural Biasing Elements for In-Cell Histone Deacetylase Paralog Selectivity," Journal of American Chemical Society, 2003, pp. 5586-5587, vol. 125.
Estiu, G., et al.; "Structural Origin of Selectivity in Class II—Selective Histone Deacetylase Inhibitors," Journal of Medicinal Chemistry, 2008, pp. 2898-2906, vol. 51.
Butler, K.V., et al.; "Chemical Origins of Isoform Selectivity in Histone Deacetylase Inhibitors," Current Pharmaceutical Design, 2008, pp. 505-528, vol. 14.
Karagiannis, T.C., et al.; "Will broad-spectrum histone deacetylase inhibitors be superseded by more specific compounds?, " Leukemia, 2007, pp. 61-65, vol. 21.
Massa, S., et al.; "Synthesis and Antimicrobial and Cytotoxic Activities of Pyrrole-Containing Analogues of Trichostatin A," Journal of Medicinal Chemistry, 1990, pp. 2845-2849, vol. 33.
Massa, S., et al.; "3-(4-Aroyl-1H-pyrrol-2-yl)-N-hydroxy-2-propenamides, a New Class of Synthetic Histone Deacetylase Inhibitors," Journal of Medicinal Chemistry, 2001, pp. 2069-2072, vol. 44.
Mai, A., et al.; "3-(4-Aroyl-1-methyl-1H-2-pyrrolyl)-N-hydroxy-2-alkylamides as a New Class of Synthetic Histome Deacetylast Inhibitors. 1. Design, Synthesis, Biological Evaluation, and Binding Mode Studies Performed through Three Different Docking Procedures," Journal of Medicinal Chemistry, 2003, pp. 512-524, vol. 46.
Inoue, S., et al.; "Inhibition of Histone Deacetylase Class I but not Class II Is Critical for the Sensitization of Leukemic Cells to Tumor Necrosis Factor-Related Apoptosis-Inducing Ligan-Induced Apoptosis," Cancer Research, 2006, pp. 6785-6792, vol. 66.
Dai, Y., et al.; "Indole Amide Hydroxamic Acids as Potent Inhinitors of Histone Deacetylases," Bioorganic Medicinal Chemistry Letters, 2003, pp. 1897-1901, vol. 13.
Arrieta, A., et al.; "Solvent-Free Thermal and Microwace-Assisted [3+2] Cycloadditions between Stabilized Azomethine Ylides and Nirtostyrenes. An Experimental and Theoretical Study," Journal of Organic Chemistry, 2007, pp. 4313-4322, vol. 72.
Zubia, A., et al.; "Identification of (1H)-pyrooles as histone deacetylase inhibitors with antitumoral activity," Oncogene, 2009, pp. 1477-1484, vol. 28.
Otaegui, D., et al.; "Pharmacokinetics and tissue distribution of Kendine 91, a novel histone deacetylase inhibitor, in mice," Cancer Chemotherapy Pharmacology, 2009, pp. 153-159, vol. 64.
Otaegui, D., et al.; "Development and validation of a liquid chromatography-tandem mass spectrometry for the determination of Kendine 91, a novel histone deacetylase inhibitor, in mice plasma and tissues: Application to a pharmacokinetic study," Journal of Chromatography B, 2008, pp. 109-116 vol. 870.
Kim, S.H., et al.; "Facile Regiocontrolled Three-Step Synthesis of Poly-Substituted Furans, Pyrroles, and Thiophenes: Consecutive Michael Addition of Methyl Cyanoacetate to Appha, Beta-Enone, Cul-Mediated Aerobic Oxidation, and Acid-Catalyzed Paal-Knorr Synthesis," Bull. Korean Chem. Soc., 2012, pp. 620-624, vol. 33.
Aginagalde, M. et al.; "Formation of Y-Oxoacides and 1H-Pyrrol-2(5H)-ones from Alpha, Beta-Unsaturated Ketones and EthylNitroacetate," Journal of Organic Chemistry, 2010, pp. 7435-7438S, vol. 75.
International Search Report, Nov. 25, 2010.

* cited by examiner

HISTONE DEACETYLASE INHIBITORS BASED SIMULTANEOUSLY ON TRISUBSTITUTED 1H-PYRROLES AND AROMATIC AND HETEROAROMATIC SPACERS

CROSS-REFERENCE TO RELATED APPLICATIONS

This application is filed under the provisions of 35 U.S.C. §371 and claims the priority of International Patent Application No. PCT/EP2010/064653 filed on 1 Oct. 2010 entitled "New Histone Deacetylase Inhibitors Based Simultaneously on Trisubstituted 1H-Pyrroles and Aromatic and Heteroaromatic Spacers" in the name of Fernando Pedro COSSÍO MORA, et al., which claims priority to European Patent Application No. 09382193.2 filed on 2 Oct. 2009, both of which are hereby incorporated by reference herein in their entirety.

FIELD OF THE INVENTION

The present invention relates to new compounds derived from trisubstituted pyrroles and conformationally restricted intermediate aromatic rings, with the processes for their preparation and with the use thereof as drugs for the treatment of cancer in pharmaceutical compositions due to their inhibitory action over class I and class II histone deacetylases.

BACKGROUND OF THE INVENTION

Histone deacetylases (HDAC) constitute an interesting therapeutic target for the treatment of cancer (cf. P. A. Marks et al. *Nature Rev. Cancer* 2001, 1, 194; J. E. Bolden et al. *Nature Rev. Drug Discov.* 2006, 5, 769; P. Gallinari et al. *Cell Res.* 2007, 17, 195; K. B. Glaser *Biochem. Pharmacol.* 2007, 74, 659; L. Pan et al. *Cell. Mol. Immunol.* 2007, 4, 337; M. Haberland et al. *Nature Rev. Genetics* 2009, 10, 32; Y. Zhang et al. *Curr. Med. Chem.* 2008, 15, 2840; S. Ropero, M. Esteller *Mol. Oncol.* 2007, 1, 19) and other diseases such as those related to central nervous system (cf. A. G. Kazantsev, L. M. Thompson. *Nature Rev. Drug Discov.* 2006, 7, 854).

Several families of HDAC inhibitors (HDACis) have been designed, whose general structures can be found in different reviews (cf. A. Villar-Garea, M. Esteller *Int. J. Cancer* 2004, 112, 171; T. A. Miller et al. *J. Med. Chem.* 2003, 46, 5097; T. Suzuki, N. Miyata *Curr. Med. Chem.* 2005, 12, 2867; M. Paris et al. *J. Med. Chem.* 2008, 51, 1505). The general structure of these inhibitors consists of a cyclic structure, a spacer and a chelating group capable of binding to the Zn (II) cation of the active center of the different HDAC isoforms that belong to the class I (HDAC1, HDAC2, HDAC3 and HDAC8), class II (HDAC4, HDAC5, HDAC6, HDAC7, HDAC9 and HDAC10) and class IV (HDAC11). Despite having a similar inhibition mode, occasionally some selectivity in the inhibition of different HDAC isoforms has been observed (cf. J. C. Wong et al. *J. Am. Chem. Soc.* 2003, 125, 5586; G. Estiu et al. *J. Med. Chem.* 2008, 51, 2898). The mentioned selectivity is of therapeutic interest (cf. K. V. Butler, A. P. Kozikowski *Curr. Pharm. Design* 2008, 14, 505; T. C. Karagiannis, A. El-Osta *Leukemia* 2007, 21, 61).

Among the chelating groups capable of binding to the Zn cation in the different isoforms of HDAC, several functional groups have been developed, such as, inter alia, carboxylic acids, hydroxamic acids, methyl and trifluoromethyl ketones, epoxides, sulfides and disulfides, o-aminobenzamides, N-hydroxyformyl derivatives, mercaptoamides, sulfones and phosphones (cf. M. Paris et al. op. cit.; T. Suzuki, N. Miyata, op. cit.). As spacer groups that connect the chelating group with the opposite side of the inhibitors, aliphatic linear chains and aromatic and heteroaromatic groups have been described. As examples of HDACis that incorporate aromatic and heteroaromatic spacers the following can be mentioned: Belinostat (PXD101), Panobinostat (LBH-589), CRA-024781, MGDC0103, Entinostat (MS-275, also described as SNDX-275), ITF2357, JNJ-16241199, Tacedinaline (CI-994) and LAQ-824 (cf. M. Paris et al. op. cit. and cited references).

On the other hand, as terminal groups that are on the opposite side of the chelating groups of the inhibitors, several cyclic, heteroaromatic and aromatic systems have been studied (cf. M. Paris et al. op. cit.; T. A. Miller op. cit.; T. Suzuki, N. Miyata op. cit.). In particular, the following groups have been used for this purpose or as spacers: 2,4-substituted-1H-pyrroles, with aroyl groups in position 4 (cf. S. Massa et al. *J. Med. Chem.* 1990, 33, 2845; S. Massa et al. *J. Med. Chem.* 2001, 44, 2069; A. Mai et al. *J. Med. Chem.* 2003, 46, 512) or cinnamoyl groups at the same position (cf. D. Chen et al. Benzimidazole derivatives: Preparation and pharmaceutical applications. WO/2005/028447, 2005; S. Inoue. et al. *Cancer Res.* 2006, 66, 6785). Likewise, concerning the monosubstituted 1H-pyrroles, the use of N-(7-(hydroxyamino)-7-oxoheptyl)-1H-pyrrol-2-carboxamide as HDACi has been described (cf. Y. Dai et al. *Bioorg. Med. Chem. Lett.* 2003, 13, 1897). Finally, some of the authors of the present invention have described the synthesis of tri- and tetrasubstituted 1H-pyrroles (cf. A. Arrieta et al. *J. Org. Chem.* 2007, 72, 4313) as well as their use as terminal groups in the obtention of HDACis (cf. A. Zubia et al. *Oncogene* 2009, 28, 1477; D. Otaegui et al. *Cancer Chemother. Pharm.* 2009, 64, 153; D. Otaegui et al. *J. Chromatography B* 2008, 870, 109; F. P. Cossío et al. Nuevos derivados pirrólicos con actividad inhibidora de desacetilasas de histonas WO/2007/074176, 2005). However, in that case only the activity of inhibitors containing pyrrole rings with linear aliphatic chains as spacers is described. The activity of 3,5-substituted 2-carboxamide-1H-pyrroles connected with the chelating groups through structures containing aromatic or heteroaromatic rings is unknown.

Within this context, the present invention describes the chemical synthesis and the HDACi activity of novel trisubstituted pyrrolic derivatives connected with the chelating groups through aromatic and heteroaromatic groups, that show inhibitory activity against several HDAC isoforms, in particular those belonging to class I and II.

OBJECT OF THE INVENTION

In an aspect, the present invention relates to the pyrrole derivatives of general formula (I):

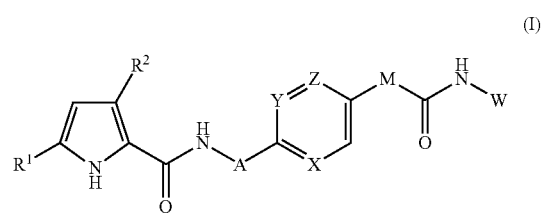

or salts, solvates or prodrugs thereof.

Likewise, another aspect of the present invention is a process for the preparation of a compound of general formula (I).

Another aspect of the present invention relates to a compound of general formula (I), or a salt, solvate or prodrug thereof, for use as a medicament.

Another aspect of the present invention relates to a compound of general formula (I), or a salt, solvate or prodrug thereof, for use as a medicament for the treatment of cancer.

Another aspect of the present invention relates to the use of a compound of general formula (I), or a salt, solvate or prodrug thereof, in the preparation of a medicament for the treatment of cancer.

According to another aspect, the present invention relates to a method of treating cancer which comprises administering to a patient needing such treatment, a therapeutically effective amount of at least one compound of general formula (I) or a salt, solvate or prodrug thereof.

According to a particular embodiment, the compounds of general formula (I) are useful for the treatment of various types of cancer by restricting tumor growth or other processes that stop the development of primary or metastatic tumors, through the inhibition of certain histone deacetylases.

Finally, in another aspect, the present invention relates to a pharmaceutical composition comprising at least one compound of general formula (I), or a salt, solvate or prodrug thereof, and at least one pharmaceutically acceptable excipient.

DETAILED DESCRIPTION OF THE INVENTION

First, the present invention provides compounds derived from 2,3,5-trisubstituted 1H-pyrrole rings having the following formula (I):

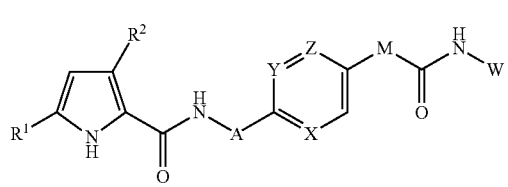

wherein:
- $R^1$ and $R^2$ represent, independently of each other, an optionally substituted $C_6$-$C_{10}$ aryl radical or an optionally substituted heteroaryl radical,
- A and M represent, independently of each other, a methylene group or a single bond, in which case the adjacent aromatic ring would be attached directly to the amide group,
- the Y=Z group represents indistinctly an oxygen atom (—O—), a sulfur atom (—S—), a cis-vinylidene group (—CH=CH—), an imino group (—N=CH— or —CH=N—), or a methine group with a sp²-hybridized carbon atom (=CH—),
- X represents indistinctly a methine group (=CH—), a cis-vinylidene group (—CH=CH—) or a nitrogen atom (=N—),
- W represents equally a hydroxyl group (—OH), an optionally substituted $C_1$-$C_6$ alkyl group, an optionally substituted heteroaryl group or an optionally substituted $C_6$-$C_{10}$ aryl group, or a salt, solvate or prodrug thereof.

According to a preferred embodiment, $R^1$ and $R^2$ represent, independently of each other, an optionally substituted phenyl group or an optionally substituted 5 or 6 membered heteroaryl group. More preferably, $R^1$ and $R^2$ represent, independently, an optionally substituted phenyl group, an optionally substituted pyridine ring, an optionally substituted furan or an optionally substituted thiophene.

According to a particular embodiment, when $R^1$ and $R^2$ represent a substituted group, such substituents are preferably selected from a $C_1$-$C_3$ alkyl group, a halogen, a nitro group, a cyano group, a trifluoromethyl group, OR', SR', SOR', SO$_2$R', NR'R'', C(O)R', C(O)OR', C(O)NR'R'' or OC(O)R'; where R' and R'' are selected, independently, between a hydrogen atom, a $C_1$-$C_3$ alkyl group, preferably a methyl, or a $C_6$-$C_{10}$ aryl group, preferably a phenyl.

According to a particular embodiment, $R^1$ and $R^2$ represent, independently, a group selected from:

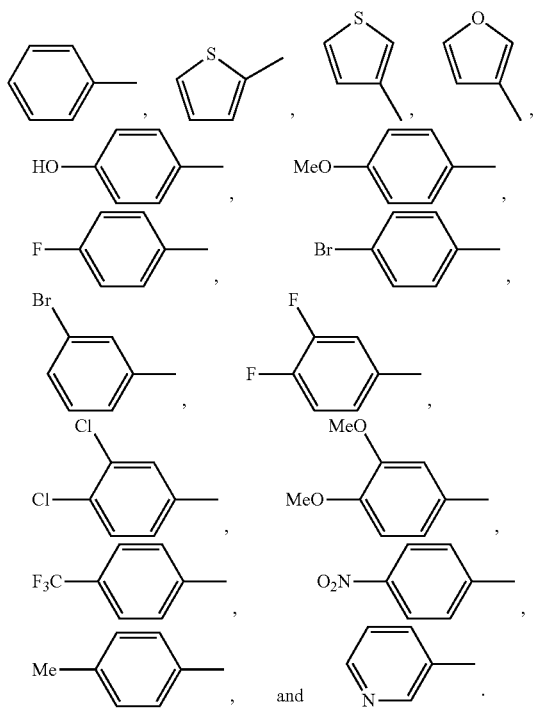

According to a particular embodiment, at least one of the groups A or M is a methylene group. According to another particular embodiment, at least one of the groups A or M is a single bond. In a preferred embodiment A is a methylene group. In another preferred embodiment M is a single bond.

According to a particular embodiment, Y=Z and X form together with the carbon atoms which they are attached to, a phenyl, a pyridine, a pyrazine or a furan ring.

According to a particular embodiment, W represents a hydroxyl group (—OH); a $C_1$-$C_6$ alkyl group, preferably an optionally substituted $C_1$-$C_3$ alkyl group; a 5 or 6 membered heteroaryl group, preferably a 5 or 6 membered heteroaryl group containing nitrogen, preferably an optionally substituted pyridine or pyrimidine group; or a $C_6$-$C_{10}$ aryl group, preferably an optionally substituted phenyl group.

According to a particular embodiment, when W represents a substituted group, such substituents are selected preferably between a $C_1$-$C_3$ alkyl, halogen, nitro, cyano, OR', SR', SOR', SO$_2$R', NR'R'', C(O)R', C(O)OR', C(O)NR'R'' or OC(O)R'; where R' and R'' are selected, independently, from a hydrogen atom, a $C_1$-$C_3$ alkyl group, preferably a methyl, or a $C_6$-$C_{10}$ aryl group, preferably a phenyl.

According to a particular embodiment, W represents a group selected from:

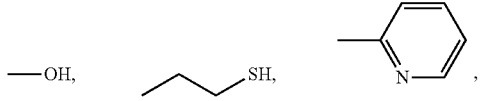

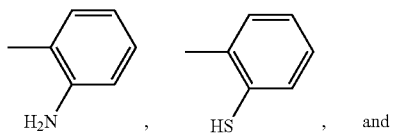

and

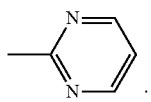

In a preferred embodiment, the compounds of general formula (I) are selected from:

[1] 5-(3-Furyl)-N-{4-[(hydroxyamino)carbonyl]benzyl}-3-(4-hydroxyphenyl)-1H-pyrrole-2-carboxamide, with the following structural formula:

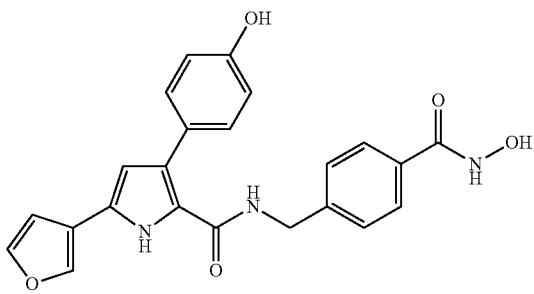 [SMILES: O=C(NO)c1ccc(CNC(=O)c2[nH]c(-c3ccoc3)cc2-c2ccc(O)cc2)cc1]

[2] N-{4-[(Hydroxyamino)carbonyl]benzyl}-3-(4-hydroxyphenyl)-5-phenyl-1H-pyrrole-2-carboxamide, with the following structural formula:

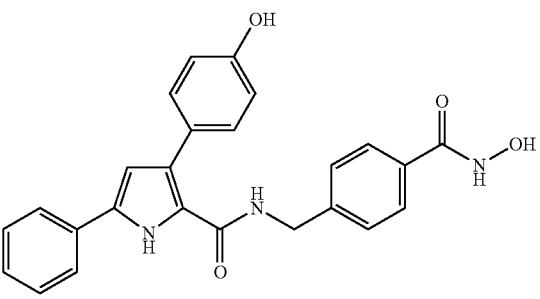 [SMILES: O=C(NO)c1ccc(CNC(=O)c2[nH]c(-c3ccccc3)cc2-c2ccc(O)cc2)cc1]

[3] 6-[({[3-(4-Fluorophenyl)-5-(2-thienyl)-1H-pyrrol-2-yl]carbonyl}amino)methyl]-N-hydroxynicotinamide, with the following structural formula:

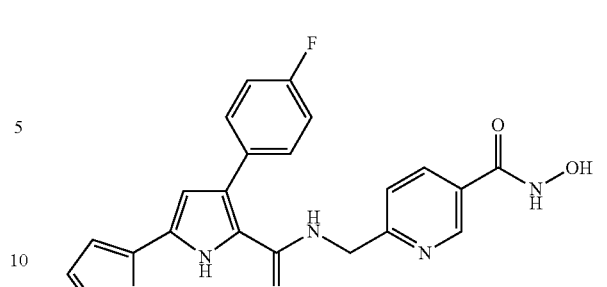

[4] 3-(4-Fluorophenyl)-5-(3-furyl)-N-{4-[(hydroxyamino)carbonyl]benzyl}-1H-pyrrole-2-carboxamide, with the following structural formula:

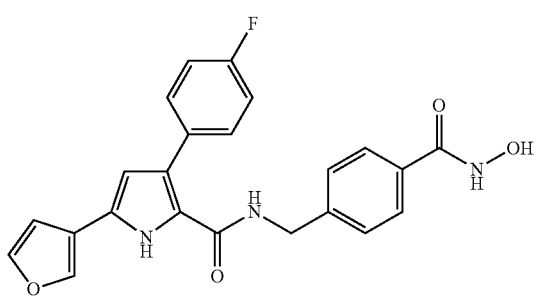 [SMILES: O=C(NO)c1ccc(CNC(=O)c2[nH]c(-c3ccoc3)cc2-c2ccc(F)cc2)cc1]

[5] N-{4-[(Hydroxyamino)carbonyl]benzyl}-3-(4-hydroxyphenyl)-5-(2-thienyl)-1H-pyrrole-2-carboxamide, with the following structural formula:

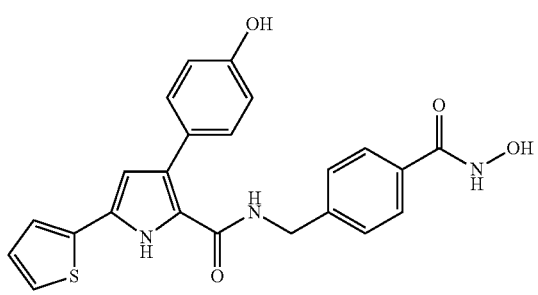 [SMILES: O=C(NO)c1ccc(CNC(=O)c2[nH]c(-c3cccs3)cc2-c2ccc(O)cc2)cc1]

[6] N-{5-[(Hydroxyamino)carbonyl]-2-furyl}-3-(4-methoxyphenyl)-5-phenyl-1H-pyrrole-2-carboxamide, with the following structural formula:

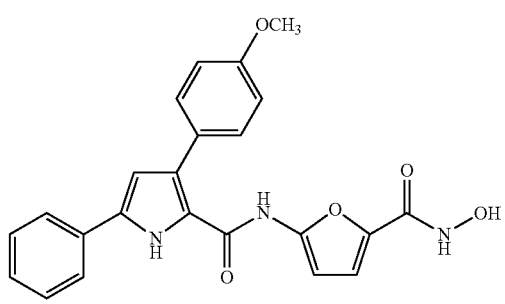 [SMILES: COc1ccc(-c2cc(-c3ccccc3)[nH]c2C(=O)Nc2ccc(C(=O)NO)o2)cc1]

[7] 3-(4-Fluorophenyl)-N-({5-[(hydroxyamino)carbonyl]-2-furyl}methyl)-5-phenyl-1H-pyrrole-2-carboxamide, with the following structural formula:

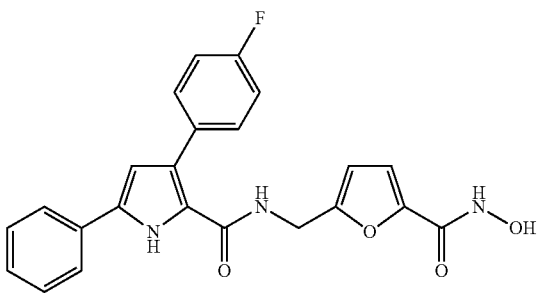 [SMILES: O=C(NO)c1ccc(CNC(=O)c2[nH]c(-c3ccccc3)cc2-c2ccc(F)cc2)o1]

[8] N-{3-[2-(hydroxyamino)-2-oxoethyl]phenyl}-3-(4-methoxyphenyl)-5-phenyl-1H-pyrrole-2-carboxamide, with the following structural formula:

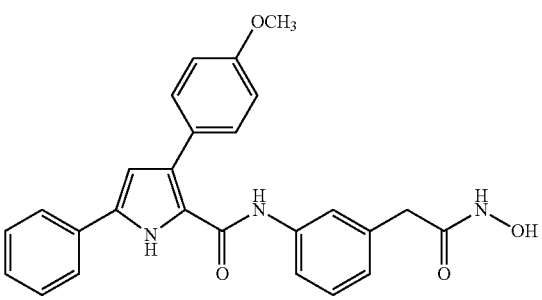 [SMILES: COc1ccc(-c2cc(-c3ccccc3)[nH]c2C(=O)Nc2cccc(CC(=O)NO)c2)cc1]

[9] N-{4-[(Hydroxyamino)carbonyl]benzyl}-5-(4-hydroxyphenyl)-3-(3-thienyl)-1H-pyrrole-2-carboxamide, with the following structural formula:

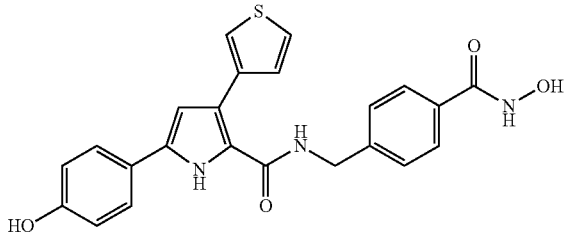 [SMILES: O=C(NO)c1ccc(CNC(=O)c2[nH]c(-c3ccc(O)cc3)cc2-c2ccsc2)cc1]

[10] 3-(3-Furyl)-N-{4-[(hydroxyamino)carbonyl]benzyl}-5-(4-hydroxyphenyl)-1H-pyrrole-2-carboxamide, with the following structural formula:

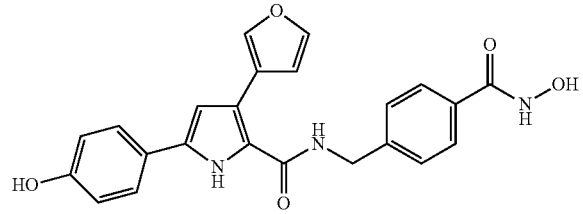

[11] N-(4-{[(2-Aminophenyl)amino]carbonyl}benzyl)-3-(4-methoxyphenyl)-5-phenyl-1H-pyrrole-2-carboxamide, with the following structural formula:

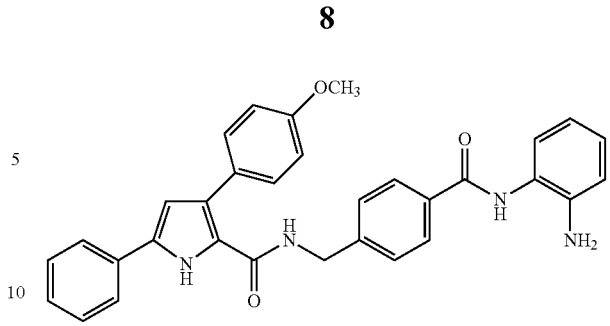

[12] 3-(4-Methoxyphenyl)-5-phenyl-N-(4-{[(2-sulfanylphenyl)amino]carbonyl}benzyl)-1H-pyrrole-2-carboxamide, with the following structural formula:

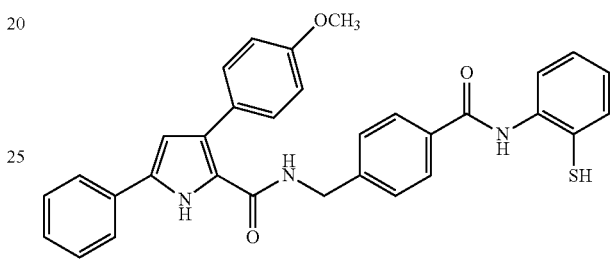

[13] 3-(4-Methoxyphenyl)-5-phenyl-N-(4-{[(2-sulfanylethyl)amino]carbonyl}benzyl)-1H-pyrrole-2-carboxamide, with the following structural formula:

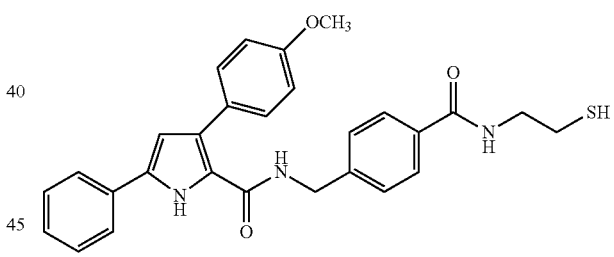

[14] 3-(4-Methoxyphenyl)-5-phenyl-N-{4-[(pyridin-2-ylamino)carbonyl]benzyl}-1H-pyrrole-2-carboxamide, with the following structural formula:

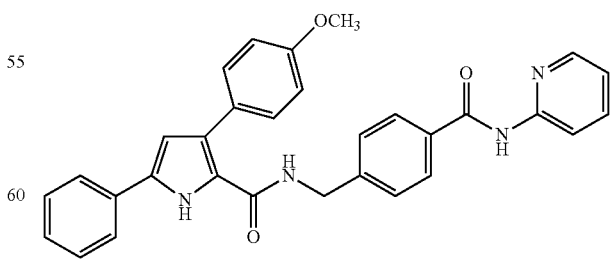

[15] 3-(4-Methoxyphenyl)-5-phenyl-N-{4-[(pyrimidin-2-ylamino)carbonyl]benzyl}-1H-pyrrole-2-carboxamide, with the following structural formula:

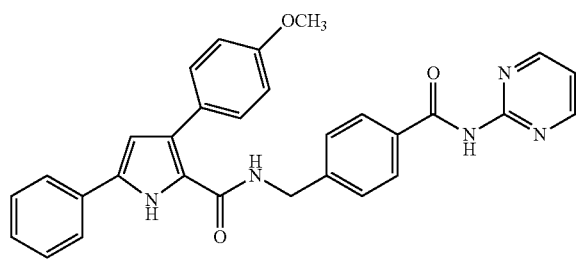

[16] N-{4-[(hydroxyamino)carbonyl]phenyl}-3-(4-methoxyphenyl)-5-phenyl-1H-pyrrole-2-carboxamide, with the following structural formula:

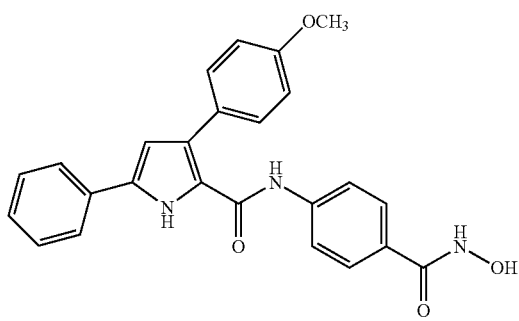 [SMILES: COc1ccc(-c2cc(-c3ccccc3)[nH]c2C(=O)Nc2ccc(C(=O)NO)cc2)cc1]

[17] 3-(3-Furyl)-N-{4-[(hydroxyamino)carbonyl]benzyl}-5-(4-methoxyphenyl)-1H-pyrrole-2-carboxamide, with the following structural formula:

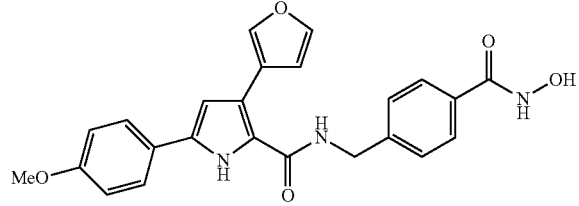 [SMILES: COc1ccc(-c2cc(-c3ccoc3)c(C(=O)NCc3ccc(C(=O)NO)cc3)[nH]2)cc1]

[18] N-{4-[(hydroxyamino)carbonyl]benzyl}-5-(4-methoxyphenyl)-3-(3-thienyl)-1H-pyrrole-2-carboxamide, with the following structural formula:

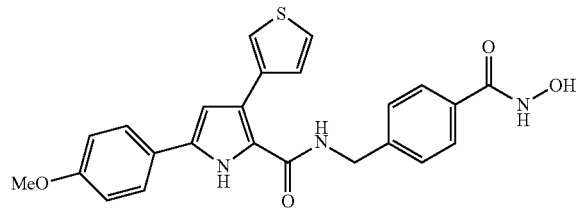 [SMILES: COc1ccc(-c2cc(-c3ccsc3)c(C(=O)NCc3ccc(C(=O)NO)cc3)[nH]2)cc1]

[19] 3-(4-Fluorophenyl)-N-{4-[(hydroxyamino)carbonyl]benzyl}-5-phenyl-1H-pyrrole-2-carboxamide, with the following structural formula:

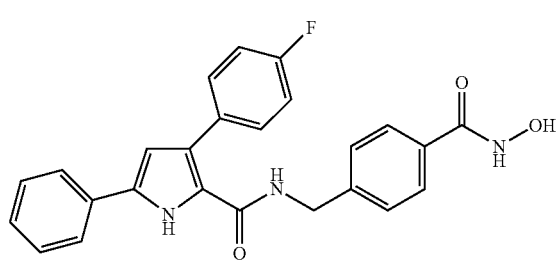 [SMILES: O=C(NO)c1ccc(CNC(=O)c2[nH]c(-c3ccccc3)cc2-c2ccc(F)cc2)cc1]

[20] 3,5-Bis-(4-fluorophenyl)-N-{4-[(hydroxyamino)carbonyl]benzyl}-1H-pyrrole-2-carboxamide, with the following structural formula:

[21] 3-(4-Fluorophenyl)-N-{4-[(hydroxyamino)carbonyl]benzyl}-5-(2-thienyl)-1H-pyrrole-2-carboxamide, with the following structural formula:

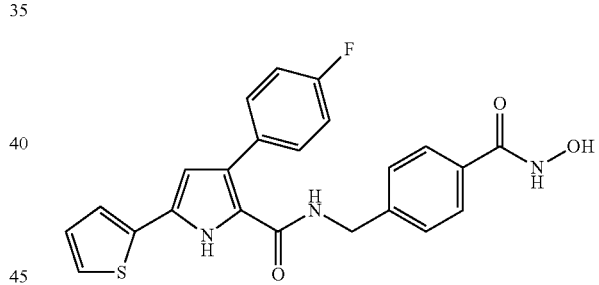

[22] 3-(4-Fluorophenyl)-N-{2-[(hydroxyamino)carbonyl]-5-pyridyl-methyl}-5-(2-thienyl)-1H-pyrrole-2-carboxamide, with the following structural formula:

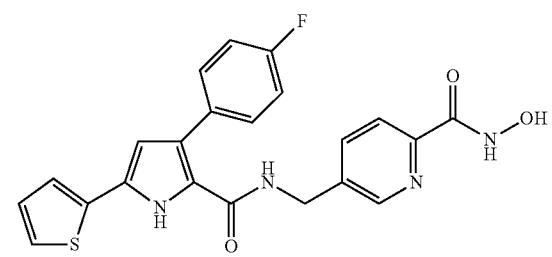 [SMILES: O=C(NO)c1ccc(CNC(=O)c2[nH]c(-c3cccs3)cc2-c2ccc(F)cc2)cn1]

[23] N-(4-{[(2-Aminophenyl)amino)carbonyl]benzyl}-5-(4-hydroxyphenyl)-3-(3-thienyl)-1H-pyrrole-2-carboxamide, with the following structural formula:

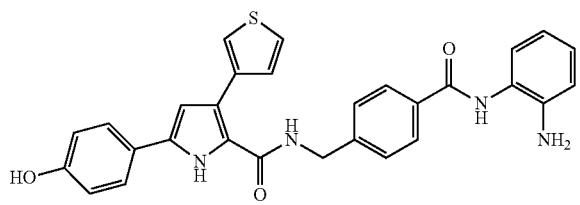 [SMILES: Nc1ccccc1NC(=O)c1ccc(CNC(=O)c2[nH]c(-c3ccc(O)cc3)cc2-c2ccsc2)cc1]

[24] N-(4-{[(2-Aminophenyl)amino)carbonyl]benzyl}-5-(3-furyl)-3-(4-hydroxyphenyl)-1H-pyrrole-2-carboxamide, with the following structural formula:

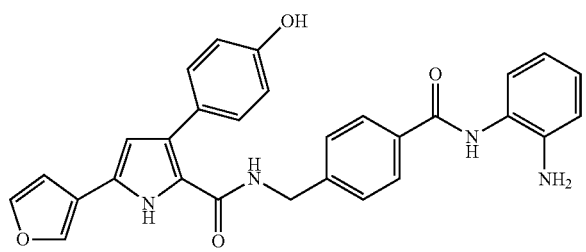 [SMILES: Nc1ccccc1NC(=O)c1ccc(CNC(=O)c2[nH]c(-c3ccoc3)cc2-c2ccc(O)cc2)cc1]

[25] N-(4-{[(2-Aminophenyl)amino)carbonyl]benzyl}-5-(4-hydroxyphenyl)-3-phenyl-1H-pyrrole-2-carboxamide, with the following structural formula:

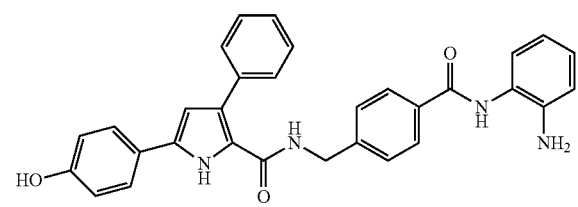 [SMILES: Nc1ccccc1NC(=O)c1ccc(CNC(=O)c2[nH]c(-c3ccc(O)cc3)cc2-c2ccccc2)cc1]

[26] N-(4-{[(2-Aminophenyl)amino)carbonyl]benzyl}-3-(4-hydroxyphenyl)-5-(3-thienyl)-1H-pyrrole-2-carboxamide, with the following structural formula:

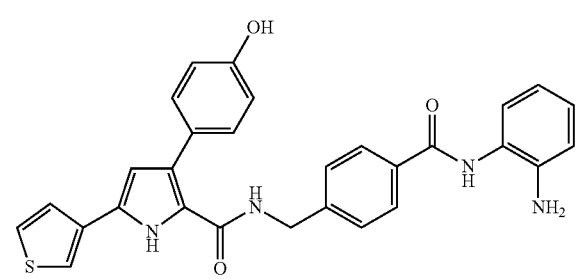 [SMILES: Nc1ccccc1NC(=O)c1ccc(CNC(=O)c2[nH]c(-c3ccsc3)cc2-c2ccc(O)cc2)cc1]

[27] N-(4-{[(2-Aminophenyl)amino)carbonyl]benzyl}-3-(3-furyl)-5-(4-hydroxyphenyl)-1H-pyrrole-2-carboxamide,

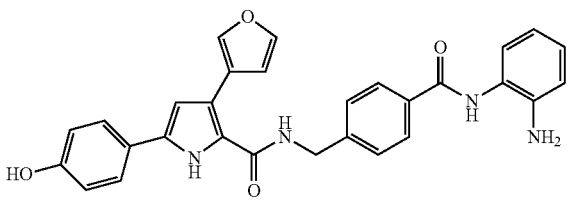

[28] N-{4-[(Hydroxyamino)carbonyl]benzyl}-3-(4-methoxyphenyl)-5-phenyl-1H-pyrrole-2-carboxamide, with the following structural formula:

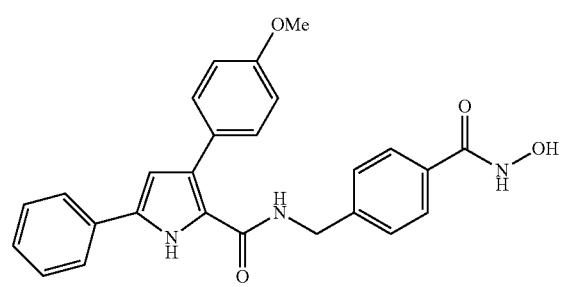 [SMILES: COc1ccc(-c2cc(-c3ccccc3)[nH]c2C(=O)NCc2ccc(C(=O)NO)cc2)cc1]

[29] N-{4-[(Hydroxyamino)carbonyl]benzyl}-5-phenyl-3-(4-trifluoromethylphenyl)-1H-pyrrole-2-carboxamide, with the following structural formula:

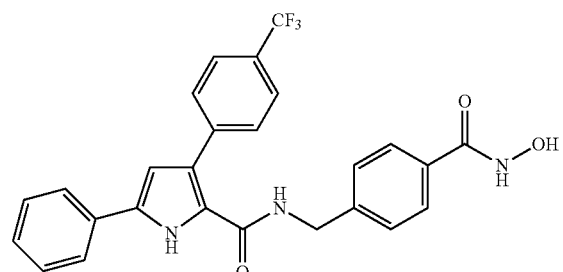

[30] 3-(4-Bromophenyl)-N-{4-[(Hydroxyamino)carbonyl]benzyl}-5-phenyl-1H-pyrrole-2-carboxamide, with the following structural formula:

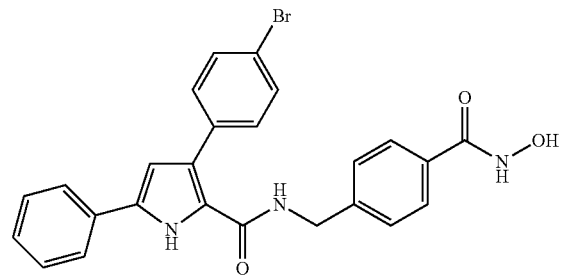

[31] N-{4-[(Hydroxyamino)carbonyl]benzyl}-3-(3,4-dimethoxyphenyl)-5-phenyl-1H-pyrrole-2-carboxamide, with the following structural formula:

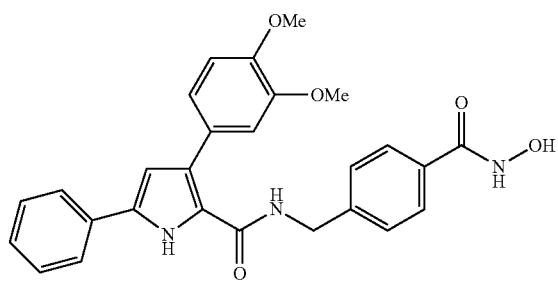 [SMILES: COc1ccc(-c2cc(-c3ccccc3)[nH]c2C(=O)NCc2ccc(C(=O)NO)cc2)cc1OC]

[32] 3-(3,4-Difluorophenyl)-N-{4-[(hydroxyamino)carbonyl]benzyl}-5-phenyl-1H-pyrrole-2-carboxamide, with the following structural formula:

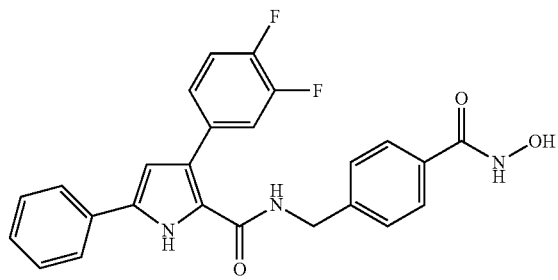 [SMILES: O=C(NO)c1ccc(CNC(=O)c2[nH]c(-c3ccccc3)cc2-c2ccc(F)c(F)c2)cc1]

[33] N-{4-[(Hydroxyamino)carbonyl]benzyl}-3-(4-nitrophenyl)-5-phenyl-1H-pyrrole-2-carboxamide, with the following structural formula:

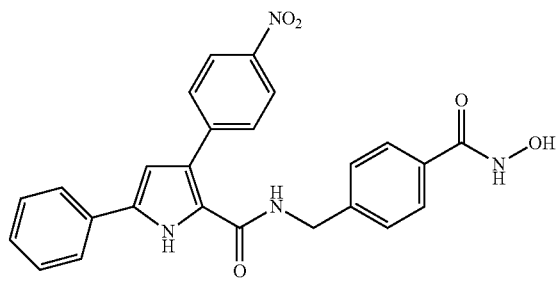

[34] 3-(3,4-Dichlorophenyl)-N-{4-[(hydroxyamino)carbonyl]benzyl}-5-phenyl-1H-pyrrole-2-carboxamide, with the following structural formula:

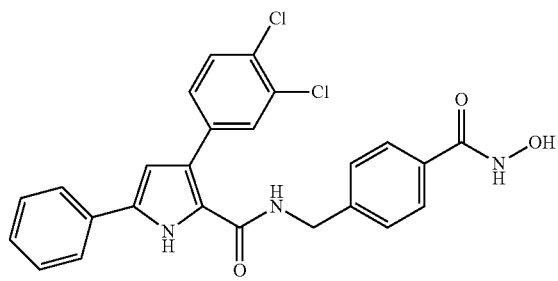

[35] 3-(3-Bromophenyl)-N-{4-[(hydroxyamino)carbonyl]benzyl}-5-phenyl-1H-pyrrole-2-carboxamide, with the following structural formula:

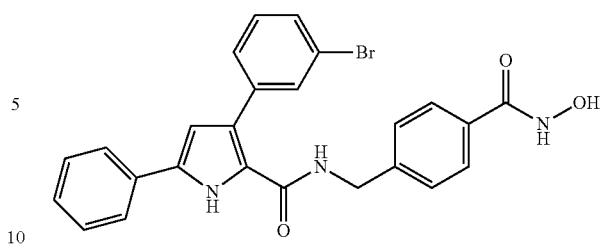

[36] 3-(4-Fluorophenyl)-N-{4-[(hydroxyamino)carbonyl]benzyl}-5-(3-pyridinyl)-1H-pyrrole-2-carboxamide, with the following structural formula:

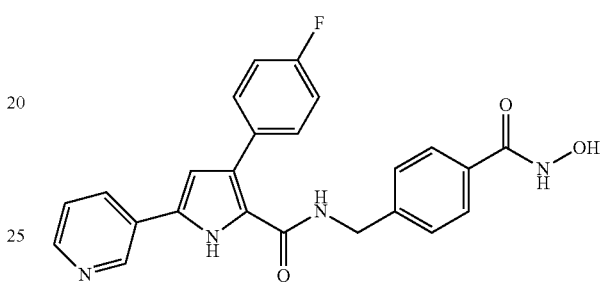

[37] 3-(4-Fluorophenyl)-N-{4-[(hydroxyamino)carbonyl]benzyl}-5-(4-methylphenyl)-1H-pyrrole-2-carboxamide, with the following structural formula:

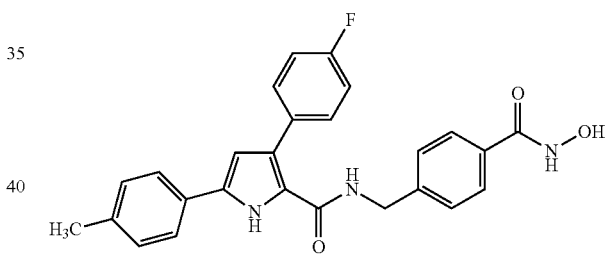

or a salt, solvate or prodrug thereof.

In the context of the present invention, the following terms have the meanings detailed below:

The term "$C_1$-$C_6$ alkyl" refers to a linear or branched hydrocarbon chain consisting of carbon and hydrogen atoms, containing no unsaturation, having from 1 to 6 carbon atoms, preferably between 1 and 3 ("$C_1$-$C_3$ alkyl"), and which is attached to the rest of the molecule through a single bond, including for example and in a non limiting sense, methyl, ethyl, n-propyl, i-propyl, n-butyl, t-butyl, n-pentyl, etc.

The term "$C_6$-$C_{10}$ aryl" refers to an aromatic group having 6 to 10 carbon atoms, comprising 1, 2 or 3 aromatic rings, linked by a carbon-carbon bond or condensed, including for example and in a non limiting sense, phenyl, naphthyl, biphenyl, indenyl, etc. Preferably "aryl" refers to phenyl.

"Heteroaryl" refers to a stable 3 to 10 membered aromatic ring, preferably a 5 or 6 membered aromatic ring, which consists of carbon atoms and from one to five heteroatoms selected from nitrogen, oxygen and sulfur. For the purposes of this invention, the heteroaryl radical may be a monocyclic, bicyclic or tricyclic ring system, which may include condensed ring systems; and nitrogen, carbon or sulfur atoms in the heteroaryl radical may be optionally oxidized; and the nitrogen atom may be optionally quaternized. Examples of such heteroaryl include, but are not limited to, benzimidazole, benzothiazole, furan, thiophene, pyrrole, pyridine, pyrimidine, isothiazole, imidazole, indole, purine, quinoline, thiadiazole.

The term "halogen" refers to bromine, chlorine, iodine or fluorine.

As commonly understood in this technical area, there may be a degree of substitution in the radicals defined above. Thus, there may be substitution in either group of the present invention. References in this document with respect to substituted groups in the groups of the present invention indicate that the specified radical may be substituted in one or more positions available with one or more substituents. These substituents include, for example and in a non limiting sense, $C_{1-6}$ alkyl, $C_6$-$C_{10}$ aryl, heteroaryl, halogen, cyano, nitro, trifluoromethyl, —N(R')(R''), —OR', —SR', —SOR', —SO$_2$R', —C(O)R', —C(O)OR', —C(O)N(R')(R''), —OC(O)R'; where R' and R'' are independently selected from hydrogen, $C_1$-$C_6$ alkyl, aryl, heteroaryl and trifluoromethyl.

The compounds of formula (I) may be in the form of salts, preferably as pharmaceutically acceptable salts, as solvates or as prodrugs.

The term "pharmaceutically acceptable salts" refers to salts which, when administered to the recipient, can provide (directly or indirectly) a compound as described in the present document. "Pharmaceutically acceptable" preferably refers to compositions and molecular entities that are physiologically tolerable and do not usually produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The preparation of salts can be accomplished by methods known in the art. For example, the pharmaceutically acceptable salts of compounds provided herein are synthesized from the original compound, which contains basic residues, by conventional chemical methods. Generally, such salts are prepared, for example, by reacting free base forms of these compounds with the appropriate base or acid in water or in an organic solvent or in a mixture of both. In general, non-aqueous media like ether, ethyl acetate, ethanol, isopropanol or acetonitrile are preferred. Examples of acid addition salts include mineral acid addition salts such as, e.g. hydrochloride, hydrobromide, hydroiodide, sulfate, nitrate, phosphate salts and organic acid addition salts such as, for example, acetate, maleate, fumarate, citrate, oxalate, succinate, tartrate, malate, mandelate, methanesulfonate and p-toluenesulfonate salts. Examples of base addition salts include inorganic salts such as, for example, sodium, potassium, calcium, ammonium, magnesium, aluminum and lithium salts, and organic salts such as, for example, ethylenediamine, ethanolamine, N,N-dialkylenethanolamine, triethanolamine, glucamine and basic salts of aminoacids.

The term "prodrug" is used in its broadest sense and encompasses those derivatives that are converted in vivo into the compounds of the invention. Experts in the art would readily produce such derivatives, and include, depending on the functional groups present in the molecule and without limitation, the following derivatives of the present compounds: disulfides, thioesters, esters, amino acid esters, phosphate esters, esters of metallic salt sulfonates, carbamates and amides.

The term "solvate" according to this invention is to be understood as any form of the active compound of the invention which has another molecule (most likely a polar solvent) attached to it through noncovalent bonds. Examples of solvates include hydrates and alcoholates, for example methanolate. The compounds of the invention can be in crystalline form, either as free compounds or as solvates. Methods of solvation are known within the art. In a particular embodiment the solvate is a hydrate.

Salts, solvates and prodrugs can be prepared by methods known in the state of the art. Note that the non-pharmaceutically acceptable salts, solvates and prodrugs also fall within the scope of the invention because they can be useful in preparing pharmaceutically acceptable salts, solvates or prodrugs.

The compounds of the invention also seek to include compounds that differ only in the presence of one or more isotopically enriched atoms. For example, compounds having the present structures except for the replacement of a hydrogen by a deuterium or tritium, or the replacement of a carbon by a carbon enriched in $^{11}C$, $^{13}C$ or $^{14}C$ or a $^{15}N$ enriched nitrogen are within the scope of this invention.

Another aspect of the invention refers to different processes to obtain compounds of general formula (I). The following methods A to C describe the processes for obtaining compounds of general formula (I), or salts, solvates or prodrugs thereof, among which include compounds of formula (Ia).

Method A

Method A represents a process for the preparation of compounds of general formula (Ia):

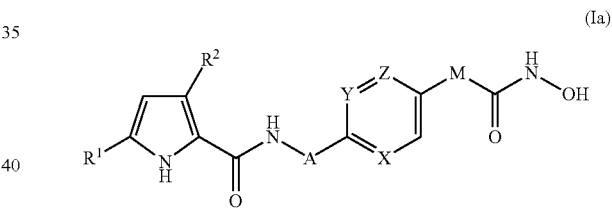

(Ia)

wherein $R^1$, $R^2$, A, M, X, Y and Z have the meaning given above in connection with the compound of formula (I), which comprises reacting:
a) a compound of formula (II);

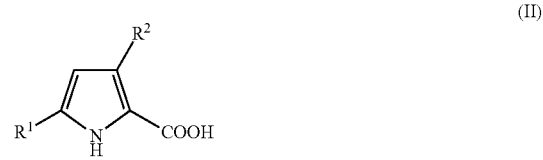

(II)

wherein $R^1$ and $R^2$ have the meaning given above,
b) a compound of formula (III),

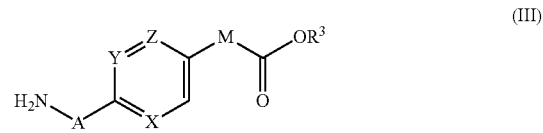

(III)

wherein R¹ and R² have the meaning given above, and R³ is a $C_1$-$C_6$ alkyl group;

c) at least one reagent for the activation of the carboxyl group; and d) a tertiary amine, preferably a tertiary amine selected from among the cyclic or acyclic aliphatic amines with $C_3$-$C_{10}$ carbon atoms and the alkano-aromatic amines with $C_9$-$C_{15}$ carbon atoms, to obtain a compound of general formula (IV),

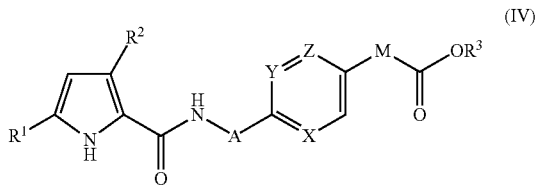
(IV)

wherein R¹, R², A, M, X, Y and Z have the meaning given above, and reacting the obtained compound of formula (IV) with a mixture of hydroxylamine hydrochloride and phenolphthalein in the presence of an excess of sodium methoxide in methanol.

For the aims of the invention, the reaction mixture made up of the four compounds a) to d) can be made by adding one of the components to the mixture formed by the three other components in an organic solvent and at a temperature ranging from −85° C. to +25° C., preferably at temperatures close to 0° C. After completion of the addition, the reaction mixture is stirred until completion of the reaction, while reaching room temperature. Upon completion of the amide formation, the ester obtained following the mentioned process is added to a mixture of hydroxylamine hydrochloride and phenolphtalein in the presence of an excess of sodium methoxide in methanol. Once the reaction is completed, after the corresponding treatment, compounds of general formula (Ia) are obtained.

Method B

Method B represents a process for the preparation of compounds of general formula (I), which comprises:

a) preparing a compound of general formula (IV) as described in Method A;

b) subjecting the mentioned compound to a hydrolysis reaction, preferably in the presence of an alkaline hydroxide and water, and an alcohol and/or a cyclic or acyclic ether, at a temperature ranging from 0° C. to 100° C., preferably at temperatures close to the range of 50° C. to 100° C., to yield an acid of general formula (V)

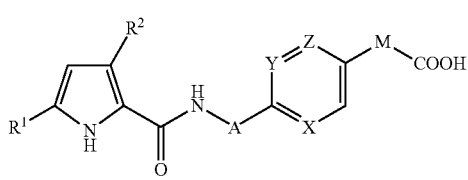
(V)

wherein R¹, R², A, M, X, Y and Z have the meaning given above in connection with the compound of formula (I); and c) reacting the compound of formula (V) with a compound of general formula (VI)

(VI)

wherein W has the meaning given above in connection with the compound of formula (I);

in the presence of a reagent for the activation of the carboxyl group, an organic solvent and a tertiary amine, preferably at temperatures ranging from 0° C. to +25° C.

Method C

Method C represents a process for the preparation of compounds of general formula (I), which comprises of the reaction of a mixture made up of:

a) a compound of general formula (II)

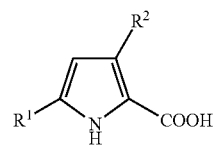
(II)

wherein R¹ and R² have the meaning given above in connection with the compound of formula (I);

b) a compound of general formula (VII)

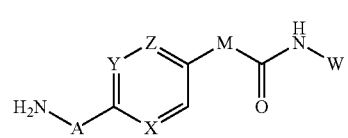
(VII)

wherein A, M, X, Y, Z and W have the meaning given above in connection with the compound of formula (I);

c) at least one reagent for the activation of the carboxyl group; and d) a tertiary amine, preferably a tertiary amine selected among the cyclic or acyclic aliphatic amines with $C_3$-$C_{10}$ carbon atoms and the alkano-aromatic amines with $C_9$-$C_{15}$ carbon atoms.

For the aims of the invention, the reaction mixture made up of the four compounds a) to d) can be made by adding one of the components to the mixture formed by the three other components in an organic solvent and at a temperature ranging from −85° C. to +25° C., preferably at temperatures close to 0° C. After completion of the addition, the reaction mixture is stirred until completion of the reaction, while reaching room temperature. Upon completion of the reaction, after the corresponding isolation and purification methods, compounds of general formula (I) are obtained.

Methods A-C may include protection and deprotection steps of functional groups, if necessary. Protecting groups and methods of protection and deprotection are well known to the skilled in the art. Illustrative examples of such protecting groups are described in Green T. W. et al. "Protective Groups in Organic Synthesis", 3rd Edition (1999), Ed. John Wiley & Sons.

According to a particular embodiment, when using a trityl group (triphenylmethyl) as a thiol protecting group in any of the compounds of the invention, the deprotection reaction is carried out preferably by reaction with a trisubstituted silane, preferably triethylsilane, an acid, preferably trifluoroacetic acid, a suitable organic solvent, preferably dichloromethane, and a salt of basic character, preferably sodium bicarbonate.

As a common element for methods A-C, the reagent or group of reagents for the activation of the carboxyl group is preferably oxalyl chloride, phenyl dichlorophosphate, diethyl cyanophosphonate (DEPC), or the 1-hydroxybenzotriazole (HOBt) and N-(3-dimethylaminopropyl)-N-ethylcarbodiimide (EDC) system. Also, the organic solvent is preferably a polar organic solvent, most preferred is N,N-dimethylformamide or 1,2-dimethoxyethane, and the tertiary amine is preferably selected among triethylamine, pyridine, N-methylpyrrolidine or N-methylmorpholine.

The preparation of compounds of formula (II) described above is performed by a process which comprises reacting a mixture formed by:

a) a α,β-unsaturated carbonylic compound with the following formula (VIII):

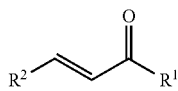

(VIII)

wherein $R^1$ and $R^2$ have the meanings given above in connection with the compound of formula (I);

b) an ester of the nitroacetic acid of general formula (IX):

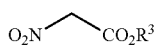

(IX)

wherein $R^3$ has the meaning given above in connection with the compound of formula (III) or (IV); and c) a primary, secondary or tertiary amine, or an inorganic base; preferably a cyclic or acyclic aliphatic or monounsaturated tertiary amine, more preferably, triethylamine, N,N-diisopropyl ethylamine (DIPEA), N-methyl morpholine, 1,8-diazabicyclo[5.4.0]undec-7-ene (DBU), or mixtures thereof.

The resulting mixture is stirred at a temperature ranging from 50° C. to 100° C. Upon completion of the reaction, the resulting product, comprising a mixture of diastereomers of α-nitro-δ-oxoester of general formula (X):

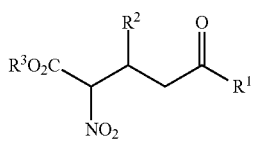

(X)

wherein $R^1$, $R^2$ and $R^3$ have the meaning given above, may be oxidized to a compound of general formula (XI). In a particular embodiment the oxidation step is performed in the presence of potassium permanganate, dimethyldioxirane, potassium peroxomonosulfate (Oxone™), titanium (III) chloride, m-chloroperoxybenzoic acid (MCPBA), freshly prepared chromium (II) chloride or mixtures thereof. In a preferred embodiment, the compound of general formula (X) is treated with an excess of sodium methoxide in methanol or sodium ethoxide in ethanol at a temperature ranging from −25° C. to +50° C., preferably at temperatures close to +25° C. The nitronate thus obtained is hydrolyzed in the presence of a strong acid and a protic solvent at a temperature ranging from −85° C. to 0° C., preferably at temperatures close to −25° C. For the purposes of the invention, a preferred embodiment refers to the use of methanol and sulfuric acid to yield the corresponding α,δ-dioxoesters of general formula (XI):

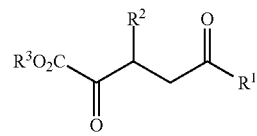

(XI)

wherein $R^1$, $R^2$ and $R^3$ have the meaning given above.

1H-Pyrrole-2-carboxylic acids of general formula (II) are obtained by treatment of previously described esters of formula (XI) with ammonium hydroxide or an ammonium salt of an aliphatic carboxylic acid of less than 5 carbon atoms in the presence of acetic acid at a temperature ranging from 25° C. to 100° C., and subsequent hydrolysis, preferably in the presence of an alkaline hydroxide, water, an alcohol and a cyclic or acyclic ether, at a temperature between 0° C. and 100° C., preferably at temperatures close to the range from 50° C. to 100° C. yielding, after the corresponding treatment, the compounds of general formula (II).

Another aspect of the present invention relates to a compound of general formula (I) or a salt, solvate or prodrug thereof, for use as a medicament.

Another aspect of the present invention relates to a compound of general formula (I) or a salt, solvate or prodrug thereof, for use as a medicament for the treatment of cancer.

Another aspect of the present invention relates to the use of a compound of general formula (I) or a salt, solvate or prodrug thereof, in the preparation of a medicament for the treatment of cancer.

In a particular embodiment, the cancer is selected from breast cancer, chronic myelogenous (or myeloid) leukemia (CML), colorectal cancer, fibrosarcoma, gastric cancer, glioblastoma, kidney cancer, liver cancer, lung cancer, melanoma, nasopharyngeal cancer, oral cancer, orthotopic multiple myeloma, osteosarcoma, ovarian cancer, pancreatic cancer, and prostate cancer.

The mechanism of action of the compounds of formula (I) is explained by their antagonist properties against histone deacetylases involved in the regulation of processes related to apoptosis, cell growth, tumor progression, cancer metastasis, cell adhesion and others. These properties prevent the binding of HDACs to their natural ligands, which can be histones or cytoplasmic proteins such as tubulin, as well as their normal catalytic activation, namely the deacetylation of ε-N-acetyl lysine residues present in these proteins.

Another aspect of the invention relates to a pharmaceutical composition comprising at least one compound of general formula (I) or a salt, solvate or prodrug thereof, and at least one pharmaceutically acceptable excipient.

The compounds of the present invention can be used with at least another drug to provide a combination therapy. This other drug or drugs may be part of the same composition, or may be provided as a separate composition and can be administered at the same time or at different times.

The term "treatment" or "treating" in the context of this document means administration of a compound or a formulation of the invention to prevent, improve or eliminate the disease or one or more symptoms associated with the disease. "Treatment" also encompasses preventing, improving or eliminating the physiological sequelae of the disease.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol, particularly for injectable solutions, are preferably used as vehicles. Suitable pharmaceutical vehicles are described in "Remington's Pharmaceutical Sciences" by E. W. Martin, 1995.

Examples of pharmaceutical compositions include any solid composition (tablets, pills, capsules, granules, etc.) or liquid composition (solutions, suspensions or emulsions) for oral, topical or parenteral administration.

In a preferred embodiment the pharmaceutical compositions are in oral delivery form. Pharmaceutical forms suitable for oral administration may be tablets and capsules and may contain conventional excipients known in the art such as binders, for example syrup, gum arabic, gelatin, sorbitol, tragacanth or polyvinylpyrrolidone; fillers, for example lactose, sugar, cornstarch, calcium phosphate, sorbitol or glycine; lubricants for the preparation of tablets, for example magnesium stearate; disintegrants, for example starch, polyvinylpyrrolidone, sodium starch glycolate or microcrystalline cellulose; or pharmaceutically acceptable wetting agents such as sodium lauryl sulphate.

Solid oral compositions can be prepared by conventional methods of blending, filling or preparation of tablets. Repeated blending operations can be used to distribute the active ingredient in all the compositions that use large amounts of fillers. Such operations are conventional in the art. The tablets can be prepared, for example, by dry or wet granulation and optionally can be coated by well known methods in normal pharmaceutical practice, in particular using a enteric coating.

Pharmaceutical compositions can also be adapted for parenteral administration, such as sterile solutions, suspensions or lyophilized products in the appropriate unit dosage form. Suitable excipients such as fillers, buffering agents or surfactants can be used.

The mentioned formulations will be prepared using standard methods such as those described or referred to in the Spanish and U.S. Pharmacopoeias and similar reference texts.

In general, the effective amount of a compound of the invention to be administered will depend on the relative efficacy of the compound chosen, the severity of the disorder being treated and the patient's weight. However, the active compounds will normally be administered one or more times a day for example 1, 2, 3 or 4 times daily, with typical total daily doses in the range from 0.01 up to 1,000 mg/kg/day.

In order to facilitate the understanding of the preceding ideas, some examples of embodiment of the present invention are described below. These examples are merely illustrative.

EXAMPLES

Example 1

Preparation of 3-(4-methoxyphenyl)-5-phenyl-1H-pyrrole-2-carboxylic acid, with the following structural formula

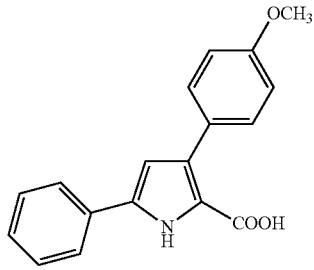 [SMILES: COc1ccc(-c2cc(-c3ccccc3)[nH]c2C(=O)O)cc1]

A solution of (2E)-3-(4-methoxyphenyl)-1-phenylprop-2-en-1-one (5 g, 20.98 mmol) and ethyl nitroacetate (2.32 ml, 20.98 mmol) in triethylamine (8.77 ml, 62.94 mmol) was stirred at 75° C. for 4 h. Ethyl acetate (500 ml) was added and the solution obtained was washed with HCl 1N (4×250 ml), dried over $Na_2SO_4$ and evaporated under reduced pressure, to obtain 7.21 g of ethyl 3-(4-methoxyphenyl)-2-nitro-5-oxo-5-phenylpentanoate.

To this material a 0.5 M solution of sodium methoxide in methanol (58.2 ml) was added and the mixture was stirred for 4 h. Then it was poured over a mixture of $H_2SO_4$ (12 ml) and MeOH (59 ml) at −20° C. The resulting mixture was stirred at −20° C. for 5 minutes, and then allowed to reach room temperature. $H_2O$ (50 ml) was added, methanol was removed under reduced pressure and the resulting aqueous solution was extracted with $CH_2Cl_2$ (2×1000 ml). The combined organic layers were washed with NaOH (2×360 ml, 1% aqueous solution) and with NaCl (2×360 ml, saturated aqueous solution), dried over $Na_2SO_4$ and evaporated under reduced pressure, to obtain 5.14 g of ethyl 3-(4-methoxyphenyl)-2,5-dioxo-5-phenylpentanoate.

To this material ammonium acetate (4.53 g, 11.75 mmol) and glacial acetic acid (7.2 ml) were added, and the mixture was stirred at 75° C. for 1 h. After reaching room temperature, ethyl acetate (800 ml) was added and the resulting solution was washed with $NaHCO_3$ (3×200 ml, saturated aqueous solution), dried over $Na_2SO_4$ and evaporated under reduced pressure, to obtain 3.28 g of ethyl 3-(4-methoxyphenyl)-5-phenyl-1H-pyrrole-2-carboxylate. This material was dissolved in ethanol (105 ml) and ethyleneglycol dimethyl ether (3 ml) and 10% NaOH (38.4 ml, aqueous solution) was added dropwise. The resulting mixture was stirred under reflux and the progress of the reaction was monitored by TLC. Upon completion of the reaction, ethanol was removed under reduced pressure and the resulting aqueous solution was cooled to 0° C., neutralized with HCl 6N and extracted with ethyl acetate (3×100 ml). The combined organic layers were dried over $Na_2SO_4$ and evaporated under reduced pressure, to obtain 2.86 g of 3-(4-methoxyphenyl)-5-phenyl-1H-pyrrole-2-carboxylic acid: Yield 41%; m.p. 198° C. (dec.); IR 3467, 1643 $cm^{-1}$; $^1$H-NMR (500 MHz, δ ppm, DMSO-$d_6$) 11.72 (s, 1H), 7.88 (d, 2H, J=7.7 Hz), 7.51 (d, 2H, J=8.4 Hz), 7.38 (t, 2H, J=7.6 Hz), 7.26 (t, 1H, J=7.2 Hz), 6.91 (d, 2H, J=8.4 Hz), 6.69 (s, 1H), 3.78 (s, 3H), 3.34 ($s_b$, 1H); $^{13}$C-NMR (126 MHz, δ ppm, DMSO-$d_6$) 162.5, 157.9, 134.4, 131.3, 131.2, 130.3, 128.6, 127.9, 127.0, 125.1, 119.8, 113.0, 112.9, 109.3, 55.0, 54.9.

Example 2

Preparation of 3-(4-hydroxyphenyl)-5-phenyl-1H-pyrrole-2-carboxylic acid, with the following structural formula

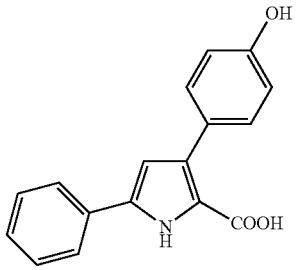 [SMILES: O=C(O)c1[nH]c(-c2ccccc2)cc1-c1ccc(O)cc1]

This material was prepared using a method substantially similar to that of Example 1 from (2E)-3-(4-hydroxyphenyl)-1-phenylprop-2-en-1-one, yielding the title compound. 3-(4-Hydroxyphenyl)-5-phenyl-1H-pyrrole-2-carboxylic acid: Yield 53%; m.p. 192-193° C.; IR 3466, 3321, 1644, 1504, 1252, 1142, 804, 747 cm$^{-1}$; $^1$H-NMR (500 MHz, δ ppm, DMSO-d$_6$) 12.14 (s$_b$, 1H), 11.63 (s, 1H), 9.29 (s, 1H), 7.87 (d, J=7.5 Hz, 2H), 7.38 (m, 4H), 7.27 (t, J=7.3 Hz, 1H), 6.74 (d, J=8.3 Hz, 2H), 6.64 (s, 1H); $^1$C-NMR (75 MHz, δ ppm, DMSO-d$_6$) 162.0, 156.2, 134.9, 132.4, 131.2, 130.4, 128.5, 127.1, 126.1, 125.2, 118.7, 114.4, 109.4.

Example 3

Preparation of 3-(4-fluorophenyl)-5-(2-thienyl)-1H-pyrrole-2-carboxylic acid, with the following structural formula

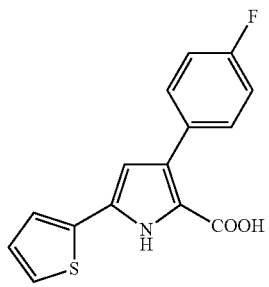 [SMILES: O=C(O)c1[nH]c(-c2cccs2)cc1-c1ccc(F)cc1]

This material was prepared using a method substantially similar to that of Example 1 from (2E)-3-(4-fluorophenyl)-1-(2-thienyl)prop-2-en-1-one, yielding the title compound. 3-(4-Fluorophenyl)-5-(2-thienyl)-1H-pyrrole-2-carboxylic acid: Yield 56%; m.p. 194-195° C.; IR 3425, 1635, 1380 cm$^{-1}$; $^1$H-NMR (300 MHz, δ ppm, DMSO-d$_6$) 7.92 (s, 1H), 7.82 (dd, J=8.5 Hz, J'=5.9 Hz, 2H), 7.53 (s, 1H), 7.36 (d, J=5.1 Hz, 1H), 7.10-6.99 (m, 4H), 6.41 (s, 1H); $^{13}$C-NMR (126 MHz, δ ppm, DMSO-d$_6$) 163.2, 161.5, 161.2, 145.0, 134.1, 132.8, 130.9, 130.8, 129.5, 129.4, 128.5, 127.8, 126.9, 115.4, 115.3, 113.8, 108.1.

Example 4

Preparation of 5-(3-furyl)-3-(4-hydroxyphenyl)-1H-pyrrole-2-carboxylic acid

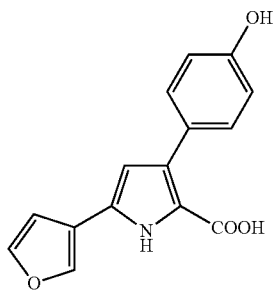 [SMILES: O=C(O)c1[nH]c(-c2ccoc2)cc1-c1ccc(O)cc1]

This material was prepared using a method substantially similar to that of Example 1 from (2E)-1-(3-furyl)-3-(4-hydroxyphenyl)prop-2-en-1-one, yielding the title compound. 5-(3-Furyl)-3-(4-hydroxyphenyl)-1H-pyrrole-2-carboxylic acid: Yield 52%; m.p. 154-156° C.; IR 3431, 3326, 1652, 1507, 1252, 1145, 782 cm$^{-1}$; $^1$H-NMR (300 MHz, δ ppm, DMSO-d$_6$) 11.47 (s, 1H), 9.31 (s$_b$, 1H), 8.22 (s, 1H), 7.66 (t, J=1.7 Hz, 1H), 7.42 (d, J=8.0 Hz, 2H), 6.97 (s, 1H), 6.71 (d, J=8.6 Hz, 2H), 6.42 (s, 1H); $^{13}$C-NMR (126 MHz, δ ppm, DMSO-d$_6$) 163.1, 156.0, 143.6, 139.1, 136.6, 132.1, 130.3, 127.0, 126.4, 118.2, 114.4, 109.0, 108.9.

Example 5

Preparation of methyl 4-[({[5-(3-furyl)-3-(4-hydroxyphenyl)-1H-pyrrol-2-yl]carbonyl}amino)methyl]benzoate

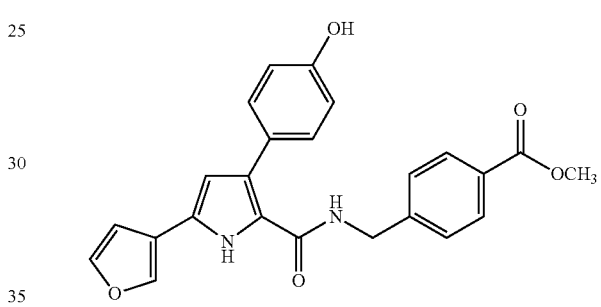

A solution of 5-(3-furyl)-3-(4-hydroxyphenyl)-1H-pyrrole-2-carboxylic acid (1.45 g, 5.5 mmol) and methyl 4-(aminomethyl)benzoate hydrochloride (1.10 g, 5.5 mmol) in DMF (27.5 ml) was cooled to 0° C. Triethylamine (4.22 ml, 30.25 mol), 1-hydroxybenzotriazole (0.81 g, 6.0 mmol), N-(3-dimethylaminopropyl)-N'-ethylcarbodiimide hydrochloride (1.17 g, 6.0 mmol) and N-methylmorpholine (0.61 ml, 5.5 mmol) were added subsequently, and the mixture was stirred for 2 h at 0° C., and for an additional 96 h at room temperature. Ethyl acetate (400 ml) was added, and the obtained solution was washed with water (75 ml), Na$_2$S$_2$O$_3$ 1N (75 ml, aqueous solution), water (75 ml), NaHCO$_3$ (75 ml, saturated aqueous solution), and NaCl (75 ml, saturated aqueous solution), dried over Na$_2$SO$_4$ and evaporated under reduced pressure, to obtain 1.43 g (3.47 mmol) of methyl 4-[({[5-(3-furyl)-3-(4-hydroxyphenyl)-1H-pyrrol-2-yl]carbonyl}amino)methyl]benzoate: Yield 63%; m.p. 223-224° C.; IR 3390, 3321, 1700, 1616, 1532, 1272 cm$^{-1}$; $^1$H-NMR (500 MHz, δ ppm, DMSO-d$_6$) 11.51 (s, 1H), 9.35 (s, 1H), 8.13 (s, 1H), 7.91 (d, J=8.2 Hz, 2H), 7.67 (t$_b$, 1H), 7.37 (d, J=8.3 Hz, 3H), 7.26 (d, J=8.5 Hz, 2H), 6.93 (d, J=0.9 Hz, 1H), 6.73 (d, J=8.5 Hz, 2H), 6.38 (d, J=2.6 Hz, 1H), 4.45 (d, J=5.8 Hz, 2H), 3.85 (s, 3H); $^{13}$C-NMR (126 MHz, δ ppm, DMSO-d$_6$) 166.0, 161.2, 156.3, 145.0, 143.6, 138.5, 129.9, 129.1, 128.1, 127.5, 127.4, 126.0, 125.9, 121.3, 118.2, 115.1, 108.7, 108.3, 51.9, 42.1.

Example 6

Preparation of methyl 6-[({[3-(4-fluorophenyl)-5-(2-thienyl)-1H-pyrrol-2-yl]carbonyl}amino)methyl]nicotinate

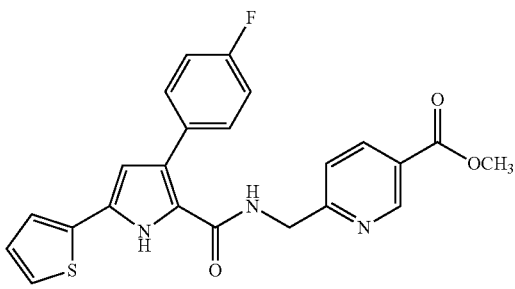 [SMILES: COC(=O)c1ccc(CNC(=O)c2[nH]c(-c3cccs3)cc2-c2ccc(F)cc2)nc1]

This material was prepared using a method substantially similar to that of Example 5 from 3-(4-fluorophenyl)-5-(2-thienyl)-1H-pyrrole-2-carboxylic acid and methyl 6-(aminomethyl)nicotinate hydrochloride, yielding the title compound. Methyl 6-[({[3-(4-fluorophenyl)-5-(2-thienyl)-1H-pyrrol-2-yl]carbonyl}amino)methyl]nicotinate: Yield 91%; m.p. 174-176° C.; IR 3378, 3245, 1723, 1618, 1505, 1433, 1218, 1113, 843 cm$^{-1}$; $^1$H-NMR (500 MHz, δ ppm, CDCl$_3$) 9.45 (s$_b$, 1H), 8.95 (s, 1H), 8.21 (dd, J=8.1 Hz, J'=2.1 Hz, 1H), 7.48 (dd, J=8.6 Hz, J'=5.4 Hz, 2H), 7.31-7.23 (m, 2H), 7.21 (d, J=3.6 Hz, 1H), 7.15 (t, J=8.6 Hz, 2H), 7.06 (dd, J=5.0 Hz, J'=3.7 Hz, 1H), 6.88 (t$_b$, J=4.6 Hz, 1H), 6.40 (d, J=3.0 Hz, 1H), 4.65 (d, J=5.0 Hz, 2H), 3.96 (s, 3H); $^{13}$C-NMR (126 MHz, δ ppm, DMSO-d$_6$) 165.9, 162.9, 161.0, 157.9, 150.0, 142.4, 138.7, 138.3, 136.7, 130.8, 128.6, 128.0, 127.6, 127.2, 122.6, 122.4, 119.3, 116.2, 116.0, 109.1, 51.5, 48.7.

Example 7

Preparation of methyl 5-[({[3-(4-fluorophenyl)-5-(2-thienyl)-1H-pyrrol-2-yl]carbonyl}amino)methyl]pyridine-2-carboxylate

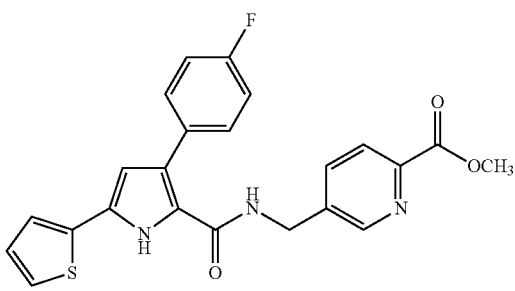

This material was prepared using a method substantially similar to that of Example 5 from 3-(4-fluorophenyl)-5-(2-thienyl)-1H-pyrrole-2-carboxylic acid and methyl 5-(aminomethyl)pyridine-2-carboxylate hydrochloride, yielding the title compound. Methyl 5-[({[3-(4-fluorophenyl)-5-(2-thienyl)-1H-pyrrol-2-yl]carbonyl}amino)methyl]pyridine-2-carboxylate: Yield 66%; m.p. 174-175° C.; IR 3398, 3255, 1733, 1643, 1541, 1432, 1258, 1121 cm$^{-1}$; $^1$H-NMR (500 MHz, δ ppm, CDCl$_3$) 9.59 (s$_b$, 1H), 8.56 (s, 1H), 8.07 (d, J=8.0 Hz, 1H), 7.66 (dd, J=8.0 Hz, J'=2.1 Hz, 1H), 7.41 (dd, J=5.3 Hz, J'=2.1 Hz, 2H), 7.25 (dd, J=5.1 Hz, J'=1.0 Hz, 1H), 7.22 (dd, J=3.6 Hz, J'=1.0 Hz, 1H), 7.10 (t, J=8.6 Hz, 2H), 7.05 (dd, J=5.0 Hz, J'=3.6 Hz, 1H), 6.38 (d, J=3.0 Hz, 1H), 6.01 (t$_b$, J=5.9 Hz, 1H), 4.53 (d, J=6.1 Hz, 2H), 4.01 (s, 3H); $^{13}$C-NMR (126 MHz, δ ppm, CDCl$_3$) 165.6, 163.8, 161.8, 161.4, 149.1, 147.3, 137.9, 136.2, 134.3, 131.4, 131.3, 131.2, 129.7, 128.1, 127.6, 125.2, 124.8, 123.5, 121.6, 116.5, 116.3, 110.4, 53.1, 40.8.

Example 8

Preparation of methyl 5-[({[3-(4-fluorophenyl)-5-(2-thienyl)-1H-pyrrol-2-yl]carbonyl}amino)methyl]pyrazine-2-carboxylate

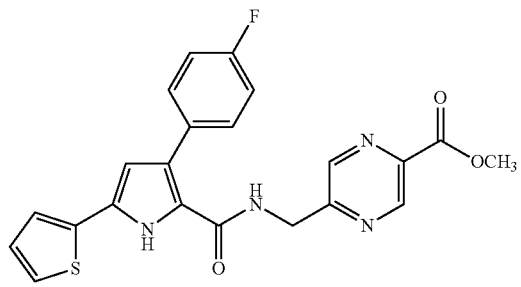

This material was prepared using a method substantially similar to that of Example 5 from 3-(4-fluorophenyl)-5-(2-thienyl)-1H-pyrrole-2-carboxylic acid and methyl 5-(aminomethyl)pyrazine-2-carboxylate hydrochloride, yielding the title compound. Methyl 5-[({[3-(4-fluorophenyl)-5-(2-thienyl)-1H-pyrrol-2-yl]carbonyl}amino)methyl]pyrazine-2-carboxylate: Yield 76%; $^1$H-NMR (500 MHz, δ ppm, CDCl$_3$) 9.47 (s$_b$, 1H), 9.07 (s, 1H), 8.64 (s, 1H), 7.47 (dd, J=8.3 Hz, J'=5.5 Hz, 2H), 7.24 (d, J=4.5 Hz, 1H), 7.21 (d, J=3.0 Hz, 1H), 7.16 (t, J=8.6 Hz, 2H), 7.06 (dd, J=4.5 Hz, J'=4.1 Hz, 1H), 6.64 (t, J=4.6 Hz, 1H), 6.40 (d, J=2.9 Hz, 1H), 4.72 (d, J=5.2 Hz, 2H), 4.04 (s, 3H).

Example 9

Preparation of 5-(3-furyl)-N-{4-[(hydroxyamino)carbonyl]benzyl}-3-(4-hydroxyphenyl)-1H-pyrrole-2-carboxamide

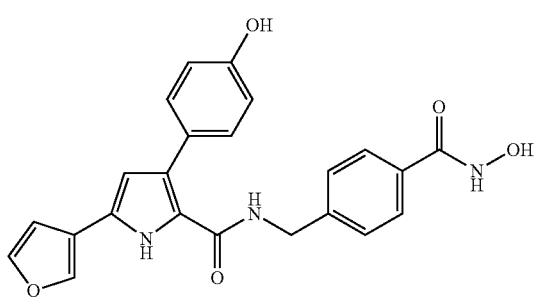 [SMILES: O=C(NO)c1ccc(CNC(=O)c2[nH]c(-c3ccoc3)cc2-c2ccc(O)cc2)cc1]

To a solution of hydroxylamine hydrochloride (0.48 g, 7.5 mmol) and phenolphtalein (1 mg) in methanol (1.25 ml)

under inert atmosphere, an aliquot of sodium methoxide in methanol (taken from a solution of 2.70 g, 50 mmol of sodium methoxide in 10 ml of methanol) was added dropwise until a permanent pink color was observed. Methyl 4-[({[5-(3-furyl)-3-(4-hydroxyphenyl)-1H-pyrrol-2-yl]carbonyl}amino)methyl]benzoate (0.52 g, 1.25 mmol) and sodium methoxide in methanol (12.5 mmol, 2.46 ml of the previously prepared solution) were subsequently added. The reaction mixture was stirred for 26 h, the formation of a dense precipitate being observed. Water (3 ml) was added, and this solution was acidified with glacial acetic acid and extracted with $CH_2Cl_2$ (3×10 ml). The combined organic fractions were dried over $Na_2SO_4$ and evaporated under reduced pressure, to obtain 0.49 g of 5-(3-furyl)-N-{4-[(hydroxyamino)carbonyl]benzyl}-3-(4-hydroxyphenyl)-1H-pyrrole-2-carboxamide: Yield 94%; m.p. 159-160° C.; IR 3406, 3243, 1626, 1526, 1268 cm$^{-1}$; $^1$H-NMR (500 MHz, δ ppm, DMSO-d$_6$) 11.50 (s, 1H), 11.13 (s, 1H), 9.36 (s, 1H), 8.94 (s, 1H), 8.13 (s, 1H), 7.69 (d, J=8.1 Hz, 2H), 7.67 (t$_b$, 1H), 7.34 (t, J=5.7 Hz, 1H), 7.30 (d, J=8.0 Hz, 2H), 7.26 (d, J=8.4 Hz, 2H), 6.93 (s, 1H), 6.74 (d, J=8.4 Hz, 2H), 6.37 (d, J=2.5 Hz, 1H), 4.41 (d, J=5.8 Hz, 2H); $^{13}$C-NMR (126 MHz, δ ppm, DMSO-d$_6$) 164.0, 161.2, 156.3, 143.6, 142.6, 138.5, 131.2, 129.9, 127.4; 127.1, 126.8, 125.9, 121.3, 118.2, 115.1, 108.7, 108.3, 42.0.

Example 10

Preparation of N-{4-[(hydroxyamino)carbonyl]benzyl}-3-(4-hydroxyphenyl)-5-phenyl-1H-pyrrole-2-carboxamide

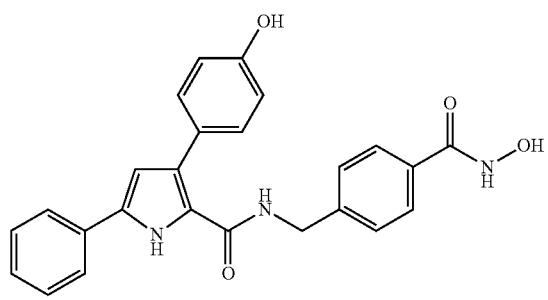 [SMILES: O=C(NO)c1ccc(CNC(=O)c2[nH]c(-c3ccccc3)cc2-c2ccc(O)cc2)cc1]

This material was prepared using a method substantially similar to that of Example 9 from methyl 4-[({[3-(4-hydroxyphenyl)-5-phenyl-1H-pyrrol-2-yl]carbonyl}amino)methyl]benzoate, yielding the title compound. N-{4-[(Hydroxyamino)carbonyl]benzyl}-3-(4-hydroxyphenyl)-5-phenyl-1H-pyrrole-2-carboxamide: Yield 69%; m.p. 139-141° C.; IR 3407, 3251, 1627, 1527, 1494, 1260 cm$^{-1}$; $^1$H-NMR (500 MHz, δ ppm, DMSO-d$_6$) 11.48 (s, 1H), 11.14 (s, 1H), 9.32 (s, 1H), 8.94 (s, 1H), 7.79 (d, J=7.9 Hz, 3H), 7.71 (d, J=8.1 Hz, 2H), 7.39 (t, J=7.6 Hz, 2H), 7.34 (d, J=8.0 Hz, 2H), 7.31 (d, J=8.4 Hz, 2H), 7.25 (t, J=7.2 Hz, 1H), 6.73 (d, J=8.4 Hz, 2H), 6.61 (d, J=2.5 Hz, 1H), 4.44 (d, J=5.6 Hz, 2H); $^{13}$C-NMR (126 MHz, δ ppm, DMSO-d$_6$) 164.1, 161.2, 156.2, 142.7, 141.1, 132.9, 131.6, 129.9, 128.7, 128.6, 127.2, 126.8, 126.7, 125.0, 124.6, 122.4, 114.8, 108.4, 42.1.

Example 11

Preparation of 6-[({[3-(4-fluorophenyl)-5-(2-thienyl)-1H-pyrrol-2-yl]carbonyl}amino)methyl]-N-hydroxynicotinamide

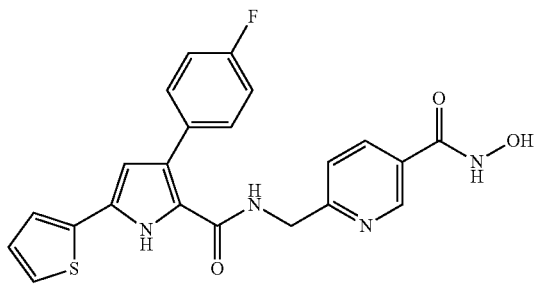 [SMILES: O=C(NO)c1ccc(CNC(=O)c2[nH]c(-c3cccs3)cc2-c2ccc(F)cc2)nc1]

This material was prepared using a method substantially similar to that of Example 9 from methyl 6-[({[3-(4-fluorophenyl)-5-(2-thienyl)-1H-pyrrol-2-yl]carbonyl}amino)methyl]nicotinate, yielding the title compound. 6-[({[3-(4-Fluorophenyl)-5-(2-thienyl)-1H-pyrrol-2-yl]carbonyl}amino)methyl]-N-hydroxynicotinamide: Yield 96%; m.p. 151-152° C.; IR 3406, 3202, 1620, 1547, 1504 cm$^{-1}$; $^1$H-NMR (500 MHz, δ ppm, DMSO-d$_6$) 11.80 (s, 1H), 11.33 (s, 1H), 9.13 (s, 1H), 8.81 (s, 1H), 8.11-8.04 (m, 2H), 7.54 (dd, J=8.5 Hz, J'=5.8 Hz, 2H), 7.51 (d, J=3.4 Hz, 1H), 7.46 (d, J=5.0 Hz, 1H), 7.42 (d, J=8.2 Hz, 1H), 7.15 (t, J=8.9 Hz, 2H), 7.10 (dd, J=4.9 Hz, J'=3.7 Hz, 1H), 6.47 (d, J=2.1 Hz, 1H), 4.54 (d, J=5.6 Hz, 2H); $^{13}$C-NMR (126 MHz, δ ppm, DMSO-d$_6$) 162.6, 162.2, 161.0, 160.9, 160.2, 147.2, 135.2, 134.4, 131.6, 131.5, 130.9, 130.8, 128.0, 127.9, 127.3, 126.9, 124.5, 123.3, 122.4, 120.9, 114.8, 114.6, 108.7, 44.2.

Example 12

Preparation of 3-(4-fluorophenyl)-5-(3-furyl)-N-{4-[(hydroxyamino)carbonyl]benzyl}-1H-pyrrole-2-carboxamide

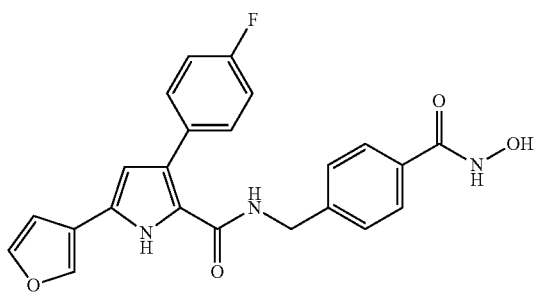 [SMILES: O=C(NO)c1ccc(CNC(=O)c2[nH]c(-c3ccoc3)cc2-c2ccc(F)cc2)cc1]

This material was prepared using a method substantially similar to that of Example 9 from methyl 4-[({[3-(4-fluorophenyl)-5-(3-furyl)-1H-pyrrol-2-yl]carbonyl}amino)methyl]benzoate, yielding the title compound. 3-(4-Fluorophenyl)-5-(3-furyl)-N-{4-[(hydroxyamino)carbonyl]benzyl}-1H-pyrrole-2-carboxamide: Yield 72%; m.p. 162-164° C.; IR 3427, 3378, 3206, 1627, 1538, 1293, 1012 cm$^{-1}$; $^1$H-NMR (200 MHz, δ ppm, DMSO-d$_6$) 11.70 (s, 1H), 11.20 (s$_b$, 1H), 9.04 (s$_b$, 1H), 8.13 (s, 1H), 7.96 (t$_b$, J=5.4 Hz, 1H), 7.72-7.68 (m, 3H), 7.48 (dd, J=8.3 Hz, J'=5.8 Hz, 2H), 7.33 (d, J=8.0 Hz, 2H), 7.14 (t, J=8.8 Hz, 2H), 6.93 (s, 1H), 6.48 (s, 1H), 4.41 (d, J=5.4 Hz, 2H); $^{13}$C-NMR (126 MHz, δ ppm, DMSO-d$_6$) 164.0, 161.9, 161.0, 160.0, 143.7, 142.7, 138.5, 131.9, 131.8, 131.2, 130.6, 130.6, 127.2, 126.8, 126.5, 125.9, 121.8, 118.1, 114.7, 114.6, 108.7, 108.2, 42.1.

Example 13

Preparation of N-{4-[(hydroxyamino)carbonyl]benzyl}-3-(4-hydroxyphenyl)-5-(2-thienyl)-1H-pyrrole-2-carboxamide

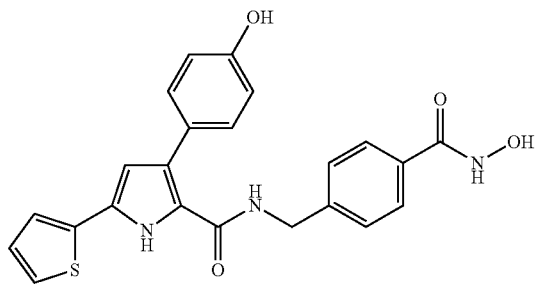 [SMILES: O=C(NO)c1ccc(CNC(=O)c2[nH]c(-c3cccs3)cc2-c2ccc(O)cc2)cc1]

This material was prepared using a method substantially similar to that of Example 9, yielding the title compound. N-{4-[(Hydroxyamino)carbonyl]benzyl}-3-(4-hydroxyphenyl)-5-(2-thienyl)-1H-pyrrole-2-carboxamide: Yield 64%; m.p. 171-172° C.; IR 3415, 3255, 1639, 1545, 1503, 1260 cm$^{-1}$; $^1$H-NMR (500 MHz, δ ppm, DMSO-d$_6$) 11.66 (s, 1H), 11.14 (s$_b$, 1H), 9.35 (s$_b$, 1H), 8.95 (s$_b$, 1H), 7.70 (d, J=7.6 Hz, 2H), 7.67 (t, J=5.7 Hz, 1H), 7.49 (d, J=3.5 Hz, 1H), 7.42 (d, J=4.9 Hz, 1H), 7.32 (d, J=7.9 Hz, 2H), 7.28 (d, J=7.8 Hz, 2H), 7.07 (dd, J=4.9 Hz, J'=3.7 Hz, 1H), 6.72 (d, J=8.0 Hz, 2H), 6.36 (s, 1H), 4.42 (d, J=5.7 Hz, 2H); $^{13}$C-NMR (126 MHz, δ ppm, DMSO-d$_6$) 161.0, 156.2, 142.6, 134.6, 131.2, 129.9, 128.0, 127.8, 127.7, 127.1, 126.7, 125.6, 124.1, 122.9, 122.0, 114.9, 108.4, 42.1.

Example 14

Preparation of N-{4-[(hydroxyamino)carbonyl]benzyl}-5-(4-hydroxyphenyl)-3-(3-thienyl)-1H-pyrrole-2-carboxamide

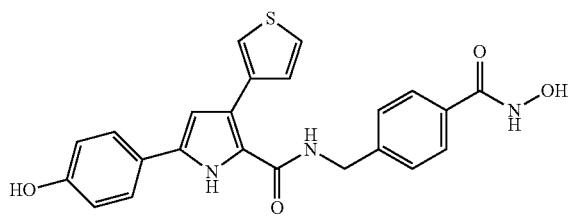 [SMILES: O=C(NO)c1ccc(CNC(=O)c2[nH]c(-c3ccc(O)cc3)cc2-c2ccoc2)cc1]

This material was prepared using a method substantially similar to that of Example 9, yielding the title compound. N-{4-[(Hydroxyamino)carbonyl]benzyl}-5-(4-hydroxyphenyl)-3-(3-thienyl)-1H-pyrrole-2-carboxamide: Yield 97%; m.p. 121-122° C.; IR 3373, 3199, 1652, 1612, 1536, 1501, 1270 cm$^{-1}$; $^1$H-NMR (300 MHz, δ ppm, DMSO-d$_6$) 11.24 (s, 1H), 11.15 (s, 1H), 9.51 (s, 1H), 8.95 (s, 1H), 8.17 (t, J=5.6 Hz, 1H), 7.81 (dd, J=2.6 Hz, J'=1.2 Hz, 1H), 7.72 (d, J=8.2 Hz, 2H), 7.60 (d, J=8.6 Hz, 2H), 7.48-7.42 (m, 2H), 7.40 (d, J=8.1 Hz, 2H), 6.80 (d, J=8.6 Hz, 2H), 6.64 (d, J=2.5 Hz, 1H), 4.49 (d, J=5.6 Hz, 2H); $^{13}$C-RMN (126 MHz, δ ppm, DMSO-d$_6$) 164.0, 161.0, 156.7, 142.8, 135.9, 133.6, 131.3, 129.1, 127.2, 126.8, 126.1, 124.5, 123.6, 122.6, 121.9, 121.4, 115.4, 106.9, 42.1.

Example 15

Preparation of 3-(3-furyl)-N-{4-[(hydroxyamino)carbonyl]benzyl}-5-(4-hydroxyphenyl)-1H-pyrrole-2-carboxamide

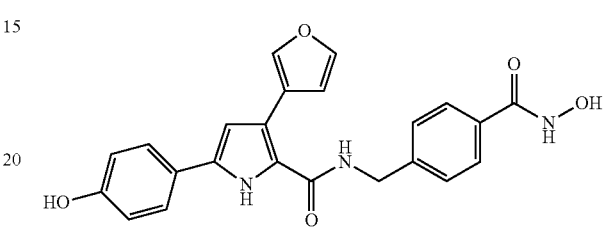

This material was prepared using a method substantially similar to that of Example 9, yielding the title compound. 3-(3-Furyl)-N-{4-[(hydroxyamino) carbonyl]benzyl}-5-(4-hydroxyphenyl)-1H-pyrrole-2-carboxamide: Yield 92%; m.p. 122-123° C.; IR 3390, 3245, 1655, 1614, 1539, 1264 cm$^{-1}$; $^1$H-NMR (300 MHz, δ ppm, DMSO-d$_6$) 11.15 (s, 2H), 9.53 (s, 1H), 8.95 (s, 1H), 8.29 (t, J=5.7 Hz, 1H), 8.25 (d, J=0.9 Hz, 1H), 7.73 (d, J=8.2 Hz, 2H), 7.61 (t, J=1.7 Hz, 1H), 7.57 (d, J=8.7 Hz, 2H), 7.42 (d, J=8.2 Hz, 2H), 6.89 (d, J=1.2 Hz, 1H), 6.82 (d, J=8.7 Hz, 2H), 6.69 (d, J=2.6 Hz, 1H), 4.52 (d, J=5.6 Hz, 2H); $^{13}$C-RMN (126 MHz, δ ppm, DMSO-d$_6$) 164.0, 160.7, 156.8, 142.9, 142.2, 140.9, 133.9, 131.3, 129.3, 127.2, 126.9, 126.1, 122.6, 120.9, 120.3, 119.6, 115.5, 111.4, 106.3, 42.0.

Example 16

Preparation of N-{5-[(hydroxyamino)carbonyl]-2-furyl}-3-(4-methoxyphenyl)-5-phenyl-1H-pyrrole-2-carboxamide

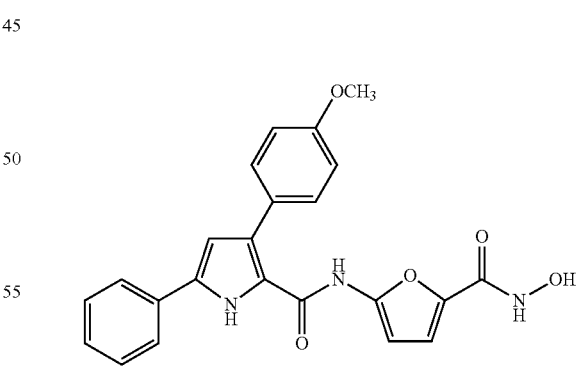

This material was prepared using a method substantially similar to that of Example 9, yielding the title compound. N-{5-[(Hydroxyamino)carbonyl]-2-furyl}-3-(4-methoxyphenyl)-5-phenyl-1H-pyrrole-2-carboxamide: Yield 74%; m.p. 160-162° C.; IR 3344, 3210, 1638, 1525, 1247, 1035 cm$^{-1}$; $^1$H-NMR (500 MHz, δ ppm, DMSO-d$_6$) 11.65 (s, 1H), 11.02 (s, 1H), 10.85 (s$_b$, 1H), 8.98 (s, 1H), 7.82 (d, J=7.7 Hz, 2H), 7.50 (d, J=8.6 Hz, 2H), 7.45 (t, J=7.7 Hz, 2H), 7.32 (t, J=7.3 Hz, 1H), 7.08 (d, J=3.0 Hz, 1H), 6.94 (d, J=8.6 Hz, 2H), 6.75 (s, 1H), 6.36 (d, J=3.5 Hz, 1H), 3.79 (s, 3H); $^{13}$C-NMR (126 MHz, δ ppm, DMSO-d$_6$) 158.1, 156.8, 149.1, 137.5, 134.1, 131.6, 131.2, 130.1, 128.7, 127.6, 127.3, 124.6, 120.5, 113.2, 109.2, 94.6, 55.0, 54.8.

Example 17

Preparation of 3-(4-fluorophenyl)-N-({5-[(hydroxyamino)carbonyl]-2-furyl}methyl)-5-phenyl-1H-pyrrole-2-carboxamide

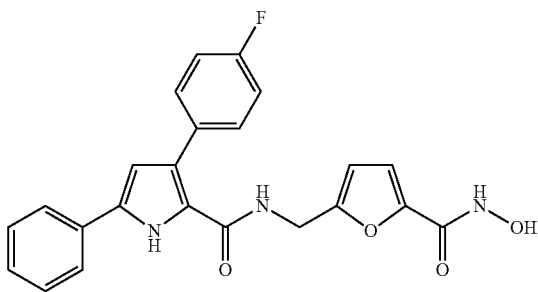 [SMILES: O=C(NO)c1ccc(CNC(=O)c2[nH]c(-c3ccccc3)cc2-c2ccc(F)cc2)o1]

This material was prepared using a method substantially similar to that of Example 9, yielding the title compound. 3-(4-Fluorophenyl)-N-({5-[(hydroxyamino)carbonyl]-2-furyl}methyl)-5-phenyl-1H-pyrrole-2-carboxamide: Yield 78%; m.p. 152-153° C.; IR 3408, 3239, 1635, 1527, 1493, 1214, 1041 cm$^{-1}$; $^1$H-NMR (500 MHz, δ ppm, DMSO-d$_6$) 11.62 (s, 1H), 11.05 (s, 1H), 9.06 (s, 1H), 8.18 (t, J=5.4 Hz, 1H), 7.79 (d, J=7.4 Hz, 2H), 7.54 (dd, J=8.6 Hz, 5.7, 2H), 7.41 (t, J=7.7 Hz, 2H), 7.27 (t, J=7.3 Hz, 1H), 7.14 (t, J=8.9 Hz, 2H), 6.99 (s, 1H), 6.72 (s, 1H), 6.41 (d, J=3.2 Hz, 1H), 4.45 (d, J=5.4 Hz, 2H); $^{13}$C-NMR (126 MHz, δ ppm, DMSO-d$_6$) 161.9, 160.7, 160.0, 156.5, 154.5, 145.0, 133.1, 131.8, 131.8, 131.4, 130.6, 130.6, 128.6, 127.7, 126.9, 124.6, 122.5, 114.5, 114.3, 113.5, 108.6, 108.4, 35.7.

Example 18

Preparation of N-{3-[2-(hydroxyamino)-2-oxoethyl]phenyl}-3-(4-methoxyphenyl)-5-phenyl-1H-pyrrole-2-carboxamide

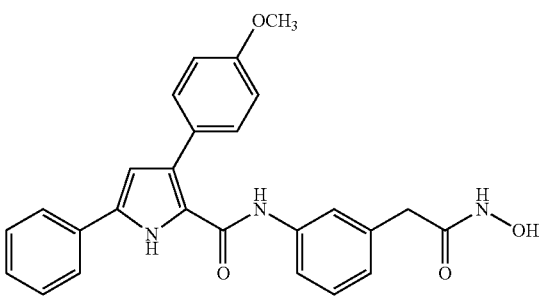 [SMILES: COc1ccc(-c2cc(-c3ccccc3)[nH]c2C(=O)Nc2cccc(CC(=O)NO)c2)cc1]

This material was prepared using a method substantially similar to that of Example 9, yielding the title compound. N-{3-[2-(Hydroxyamino)-2-oxoethyl]phenyl}-3-(4-methoxyphenyl)-5-phenyl-1H-pyrrole-2-carboxamide: Yield 82%; m.p. 205-206° C.; IR 3431, 3369, 3202, 1645, 1553, 1448, 1256 cm$^{-1}$; $^1$H-NMR (500 MHz, δ ppm, DMSO-d$_6$) 11.75 (s, 1H), 10.66 (s, 1H), 9.55 (s, 1H), 8.82 (s, 1H), 7.84 (d, J=7.7 Hz, 2H), 7.55 (s, 1H), 7.50 (d, J=7.8 Hz, 2H), 7.45-7.41 (m, 3H), 7.28 (t, J=7.2 Hz, 1H), 7.23 (t, J=7.8 Hz, 1H), 6.97-6.92 (m, 3H), 6.75 (s, 1H), 3.78 (s, 3H), 3.25 (s, 2H); $^{13}$C-NMR (126 MHz, δ ppm, DMSO-d$_6$) 166.8, 159.5, 158.0, 139.0, 136.4, 133.2, 131.5, 129.7, 128.6, 128.3, 127.7, 126.9, 124.6, 123.9, 122.9, 120.1, 117.8, 113.5, 108.3, 55.0, 36.5.

Example 19

Preparation of N-{4-[(hydroxyamino)carbonyl]phenyl}-3-(4-methoxyphenyl)-5-phenyl-1H-pyrrole-2-carboxamide

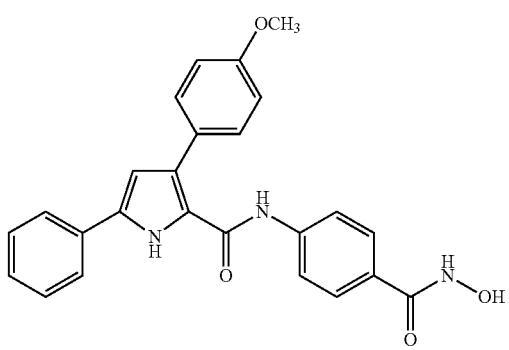 [SMILES: COc1ccc(-c2cc(-c3ccccc3)[nH]c2C(=O)Nc2ccc(C(=O)NO)cc2)cc1]

This material was prepared using a method substantially similar to that of Example 9, yielding the title compound. N-{4-[(hydroxyamino)carbonyl]phenyl}-3-(4-methoxyphenyl)-5-phenyl-1H-pyrrole-2-carboxamide: Yield 95%; m.p. 234-235° C.; IR 3349, 3247, 1637, 1528, 1438, 1245 cm$^{-1}$; $^1$H-NMR (500 MHz, δ ppm, DMSO-d$_6$) 11.84 (s, 1H), 11.10 (s, 1H), 9.81 (s, 1H), 8.93 (s$_b$, 1H), 7.86 (d, J=7.6 Hz, 2H), 7.72 (d, J=8.4 Hz, 2H), 7.66 (d, J=8.5 Hz, 2H), 7.50 (d, J=8.4 Hz, 2H), 7.43 (t, J=7.5 Hz, 2H), 7.29 (t, J=7.2 Hz, 1H), 6.94 (d, J=8.4 Hz, 2H), 6.78 (d$_b$, J=1.9 Hz, 1H), 3.77 (s, 3H); $^{13}$C-NMR (126 MHz, δ ppm, DMSO-d$_6$) 163.9, 159.8, 158.1, 141.7, 133.6, 131.4, 129.8, 129.1, 128.7, 127.6, 127.1, 127.0, 124.7, 122.7, 118.7, 113.5, 108.4, 55.0.

Example 20

Preparation of 4-[({[3-(4-methoxyphenyl)-5-phenyl-1H-pyrrol-2-yl]carbonyl}amino)methyl]benzoic acid

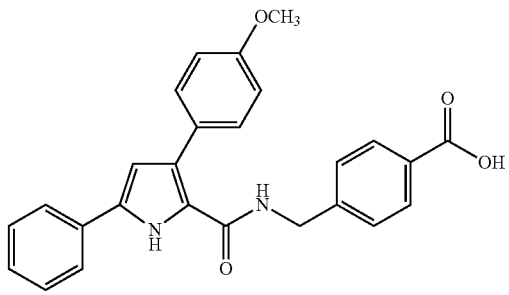 [SMILES: COc1ccc(-c2cc(-c3ccccc3)[nH]c2C(=O)NCc2ccc(C(=O)O)cc2)cc1]

To a solution of methyl 4-[({[3-(4-methoxyphenyl)-5-phenyl-1H-pyrrol-2-yl]carbonyl}amino)methyl]benzoate (1.5 g, 3.41 mmol) dissolved in ethanol (85 ml) and ethyleneglycol dimethyl ether (3.41 ml), 10% NaOH (34.1 ml, aqueous solution) was added dropwise. The resulting mixture was stirred under reflux and the progress of the reaction was monitored by TLC. Upon completion of the reaction, ethanol was removed under reduced pressure and the resulting aqueous solution was cooled to 0° C., neutralized with HCl 6N and extracted with ethyl acetate (3×100 ml). The combined organic layers were dried over $Na_2SO_4$ and evaporated under reduced pressure, to obtain 1.26 g of 4-[({[3-(4-methoxyphenyl)-5-phenyl-1H-pyrrol-2-yl]carbonyl}amino)methyl]benzoic acid: Yield 88%; m.p. 260° C. (dec); IR 3408, 3268, 1684, 1525, 1496, 1264 cm$^{-1}$; $^1$H-NMR (300 MHz, δ ppm, DMSO-d$_6$) 11.57 (s, 1H), 8.00 (t, J=5.9 Hz, 1H), 7.90 (d, J=8.2 Hz, 2H), 7.80 (d, J=7.3 Hz, 2H), 7.46-7.35 (m, 7H), 7.27 (d, J=7.0 Hz, 1H), 6.88 (d, J=8.8 Hz, 2H), 6.67 (d, J=2.2 Hz, 1H), 4.47 (d, J=5.5 Hz, 2H), 3.76 (s, 3H); $^{13}$C-NMR (126 MHz, δ ppm, DMSO-d$_6$) 167.1, 160.9, 157.9, 144.8, 133.0, 131.5, 130.1, 129.2, 128.8, 128.5, 128.0, 127.3, 126.7, 124.6, 122.3, 113.1, 108.5, 55.0, 42.0.

Example 21

Preparation of N-(4-{[(2-aminophenyl)amino]carbonyl}benzyl)-3-(4-methoxyphenyl)-5-phenyl-1H-pyrrole-2-carboxamide

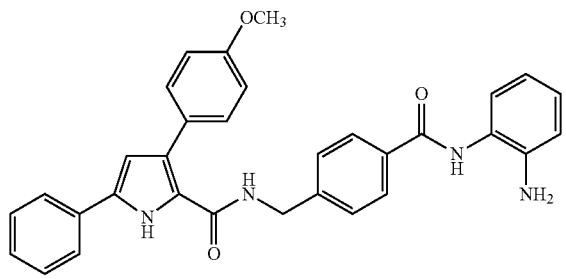 [SMILES: COc1ccc(-c2cc(-c3ccccc3)[nH]c2C(=O)NCc2ccc(C(=O)Nc3ccccc3N)cc2)cc1]

A solution of 4-[({[3-(4-methoxyphenyl)-5-phenyl-1H-pyrrol-2-yl]carbonyl}amino)methyl]benzoic acid (0.213 g, 0.5 mmol) and phenylenediamine (0.108 g, 1.0 mmol) in DMF (10 ml) was cooled to 0° C. Triethylamine (0.40 ml, 2.87 mol), 1-hydroxybenzotriazole (0.101 g, 0.75 mmol) and N-(3-dimethylaminopropyl)-N'-ethylcarbodiimide hydrochloride (0.144 g, 0.75 mmol) were added subsequently, and the mixture was stirred for 2 h at 0° C., and for an additional 96 h at room temperature. Ethyl acetate (40 ml) was added, and the obtained solution was washed with water (7 ml), $Na_2S_2O_3$ 1N (7 ml, aqueous solution), water (7 ml), NaHCO$_3$ (7 ml, saturated aqueous solution), and NaCl (7 ml, saturated aqueous solution), dried over $Na_2SO_4$ and evaporated under reduced pressure, to obtain 0.142 g (0.27 mmol) of N-(4-{[(2-aminophenyl)amino]carbonyl}benzyl)-3-(4-methoxyphenyl)-5-Phenyl-1H-pyrrole-2-carboxamide: Yield 55%; m.p. 142-143° C. (dec); IR 3407, 3296, 1627, 1530, 1493, 1246 cm$^{-1}$; $^1$H-NMR (300 MHz, δ ppm, DMSO-d$_6$) 11.54 (s, 1H), 9.61 (s, 1H), 7.95 (d, J=7.8 Hz, 3H), 7.80 (d, J=7.4 Hz, 2H), 7.45-7.38 (m, 6H), 7.26 (t, J=7.3 Hz, 1H), 7.17 (d, J=7.7 Hz, 1H), 6.97 (dt, J=8.0 Hz, J'=1.4 Hz, 1H), 6.90 (d, J=8.7 Hz, 2H), 6.79 (dd, J=7.9 Hz, J'=1.1 Hz, 1H), 6.67 (d, J=2.6 Hz, 1H), 6.60 (dt, J=7.5 Hz, J'=1.0 Hz, 1H), 4.86 (s, 2H), 4.49 (d, J=5.7 Hz, 2H), 3.77 (s, 3H); $^{13}$C-NMR (126 MHz, δ ppm, DMSO-d$_6$) 165.0, 161.1, 157.9, 143.0, 142.9, 133.1, 132.9, 131.5, 129.9, 128.6, 127.9, 127.8, 127.7, 127.1, 126.7, 126.6, 126.4, 124.5, 123.3, 122.6, 116.2, 116.1, 113.4, 108.3, 55.0, 42.1.

Example 22

Preparation of 3-(4-methoxyphenyl)-5-phenyl-N-(4-{[(2-sulfanylphenyl)amino]carbonyl}benzyl)-1H-pyrrole-2-carboxamide

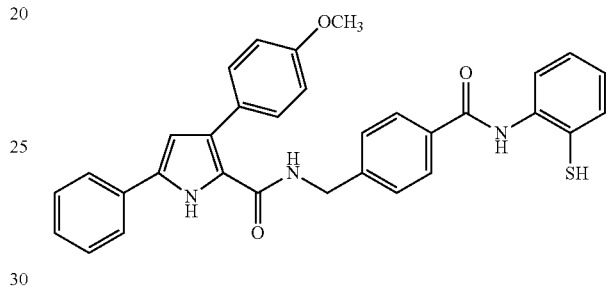

To a solution of phenyl dichlorophosphate (0.1 ml, 0.625 mmol) in DMF (0.1 ml) at 0° C. under inert atmosphere, was added dropwise a solution of 4-[({[3-(4-methoxyphenyl)-5-phenyl-1H-pyrrol-2-yl]carbonyl}amino)methyl]benzoic acid (0.206 g, 0.5 mmol) in $CH_2Cl_2$ (2.5 ml), and the resulting mixture was stirred at room temperature for 10 minutes. 2-(Tritylsulfanyl)aniline (0.404 g, 1.0 mmol) and triethylamine (4.17 ml, 30 mmol) were added subsequently, and the mixture was stirred at room temperature for 16 h. Ethyl acetate (40 ml) was added, and the obtained solution was washed with HCl 0.1N (3×7 ml), water (7 ml), and NaOH 1N (3×7 ml), dried over $Na_2SO_4$ and evaporated under reduced pressure. This material was dissolved in $CH_2Cl_2$ (5 ml), and cooled to 0° C. Trifluoroacetic acid (0.49 ml, 6.4 mmol) and triethylsilane (0.09 ml, 0.55 mmol) were added subsequently, and the resulting mixture was stirred at room temperature for 2 h. NaHCO$_3$ (7.7 ml, saturated aqueous solution) was added and the resulting mixture was stirred for 30 min. The organic layer was separated and the aqueous layer was extracted with $CH_2Cl_2$ (3×15 ml). The combined organic fractions were dried over $Na_2SO_4$ and evaporated under reduced pressure, to obtain 0.216 g (0.404 mmol) of 3-(4-methoxyphenyl)-5-phenyl-N-(4-{[(2-sulfanylphenyl)amino]carbonyl}benzyl)-1H-pyrrole-2-carboxamide: Yield 81%; m.p. 134-135° C.; IR 3407, 3384, 3233, 1681, 1638, 1525, 1493, 1249 cm$^{-1}$; $^1$H-NMR (300 MHz, δ ppm, CDCl$_3$) 10.22 (s, 1H), 8.93 (s, 1H), 8.48 (dd, J=8.3 Hz, J'=1.0 Hz, 1H), 7.63 (d, J=8.3 Hz, 4H), 7.43-7.35 (m, 6H), 7.34-7.20 (m, 4H), 6.97-6.90 (m, 3H), 6.49 (d, J=3.0 Hz, 1H), 6.24 (t, J=6.0 Hz, 1H), 4.51 (d, J=6.0 Hz, 2H), 3.81 (s, 3H); $^{13}$C-NMR (126 MHz, δ ppm, DMSO-d$_6$) 165.4, 161.2, 158.0, 143.5, 135.9, 133.5, 133.0, 132.3, 131.6, 129.9, 128.7, 127.9, 127.8, 127.6, 127.4, 127.1, 126.9, 126.8, 124.6, 123.9, 122.6, 114.0, 113.4, 108.3, 55.0, 42.2.

Example 23

Preparation of 3-(4-methoxyphenyl)-5-phenyl-N-(4-{[(2-sulfanylethyl)amino]carbonyl}benzyl)-1H-pyrrole-2-carboxamide

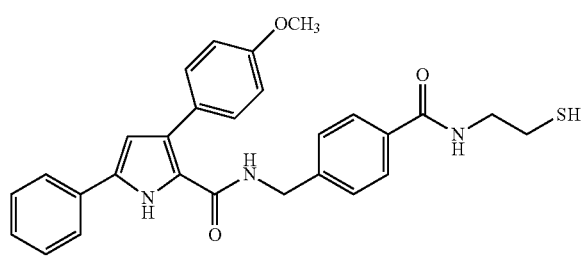 [SMILES: COc1ccc(-c2cc(-c3ccccc3)[nH]c2C(=O)NCc2ccc(C(=O)NCCS)cc2)cc1]

This material was prepared using a method substantially similar to that of Example 22 from 4-[({[3-(4-methoxyphenyl)-5-phenyl-1H-pyrrol-2-yl]carbonyl}amino)methyl]benzoic acid and 2-(tritylsulfanyl)ethanamine hydrochloride, yielding the title compound 3-(4-methoxyphenyl)-5-phenyl-N-(4-{[(2-sulfanylethyl)amino]carbonyl}benzyl)-1H-pyrrole-2 carboxamide: Yield 70%; m.p. 131-132° C.; IR 3396, 3280, 1635, 1524, 1499, 1246 cm$^{-1}$; $^1$H-NMR (500 MHz, δ ppm, CDCl$_3$) 9.99 (s, 1H), 7.72 (d, J=8.1 Hz, 2H), 7.59 (d, J=7.6 Hz, 2H), 7.38 (t, J=7.7 Hz, 2H), 7.35 (d, J=8.5 Hz, 2H), 7.28 (t, J=7.5 Hz, 1H); 7.17 (d, J=8.0 Hz, 2H), 7.03 (t, J=5.5 Hz, 1H), 6.89 (d, J=8.5 Hz, 2H), 6.47 (d, J=2.9 Hz, 1H), 6.17 (t, J=5.8 Hz, 1H), 4.45 (d, J=5.9 Hz, 2H), 3.85-3.73 (m, 5H), 2.97 (t, J=6.2 Hz, 2H), 1.62 (s, 1H); $^{13}$C-NMR (75 MHz, δ ppm, CDCl$_3$) 167.7, 161.7, 159.6, 142.4, 134.6, 133.4, 131.6, 130.8, 129.6, 129.2, 128.7, 128.5, 128.3, 127.7, 127.6, 124.9, 122.3, 114.7, 109.8, 55.6, 43.1, 39.5, 38.4, 29.9.

Example 24

Preparation of 4-(aminomethyl)-N-pyridin-2-ylbenzamide hydrochloride

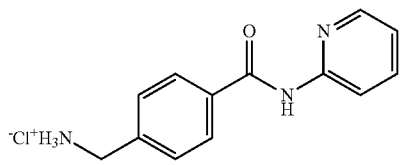

To a solution of 4-{[(tert-butoxycarbonyl)amino]methyl}benzoic acid (0.75 g, 3 mmol) in toluene (12 ml) under inert atmosphere, were added anhydrous DMF (0.03 ml), pyridine (1.5 ml, 18.62 mmol) and oxalyl chloride (0.52 ml, 6 mmol), and the resulting mixture was stirred for 6 h, the formation of a precipitate being observed. This precipitate was filtered off and washed with toluene. The combined filtrates were dried over Na$_2$SO$_4$ and evaporated under reduced pressure, to obtain the corresponding acid chloride. This solid was dissolved in pyridine (9.3 ml, 115 mmol) under inert atmosphere, and 2-aminopyridine (0.31 g, 3.3 mmol) was added. The resulting mixture was stirred for 16 h. CHCl$_3$ (100 ml) was added and the resulting solution was washed with NaHCO$_3$ (3×15 ml, saturated aqueous solution), and NaCl (3×15 ml, saturated aqueous solution), dried over Na$_2$SO$_4$ and evaporated under reduced pressure. The obtained material was dissolved in methanol (100 ml) and the resulting solution was cooled to 0° C. HCl 6N (7.5 ml) was added, and the reaction mixture was stirred at room temperature for 16 h. The solution was concentrated in vacuo to give 0.406 g (1.54 mmol) of 4-(aminomethyl)-N-pyridin-2-ylbenzamide hydrochloride: Yield 51%; m.p. 258-259° C.; IR 3442, 3303, 1672, 1609, 1571, 1437, 1249 cm$^{-1}$; $^1$H-NMR (500 MHz, δ ppm, DMSO-d$_6$) 10.89 (s, 1H), 8.41 (d, J=3.4 Hz, 1H), 8.39-8.31 (m, 3H), 8.19 (d, J=8.4 Hz, 1H), 8.09 (d, J=8.0 Hz, 2H), 7.89 (t, J=7.6 Hz, 1H), 7.61 (d, J=8.0 Hz, 2H), 7.21 (t, J=5.6 Hz, 1H), 4.12 (d, J=5.4 Hz, 2H); $^{13}$C-NMR (126 MHz, δ ppm, DMSO-d$_6$) 165.9, 150.6, 144.7, 141.1, 138.5, 133.0, 128.8, 128.3, 120.2, 115.6, 41.7.

Example 25

Preparation of 3-(4-methoxyphenyl)-5-phenyl-N-{4-[(pyridin-2-ylamino)carbonyl]benzyl}-1H-pyrrole-2-carboxamide

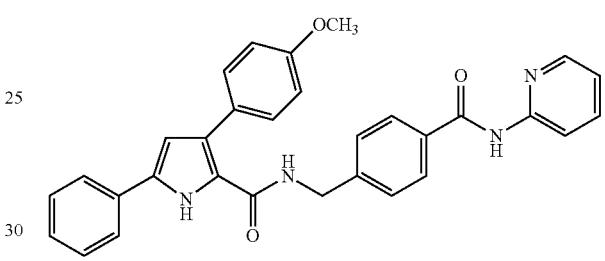

This material was prepared using a method substantially similar to that of Example 5 from 3-(4-methoxyphenyl)-5-phenyl-1H-pyrrole-2-carboxylic acid and 4-(aminomethyl)-N-pyridin-2-ylbenzamide hydrochloride, yielding the title compound. 3-(4-Methoxyphenyl)-5-phenyl-N-{4-[(pyridin-2-ylamino)carbonyl]benzyl}-1H-pyrrole-2-carboxamide: Yield 71%; m.p. 196° C. (dec.); IR 3402, 3239, 1623, 1536, 1432, 1304, 1246 cm$^{-1}$; $^1$H-NMR (300 MHz, δ ppm, CDCl$_3$) 9.75 (s, 1H), 8.77 (s, 1H), 8.39 (d, J=8.4 Hz, 1H), 8.29 (d, J=4.8 Hz, 1H), 7.88 (d, J=8.3 Hz, 2H), 7.77 (dt, J=7.0 Hz, J'=1.8 Hz, 1H), 7.57 (d, J=7.2 Hz, 2H), 7.45-7.27 (m, 7H), 7.07 (ddd, J=7.3 Hz, J'=5.0 Hz, J''=0.8 Hz, 1H), 6.90 (d, J=8.7 Hz, 2H), 6.49 (d, J=3.0 Hz, 1H), 6.13 (t, J=5.8 Hz, 1H), 4.52 (d, J=5.9 Hz, 2H), 3.82 (s, 3H); $^{13}$C-NMR (75 MHz, δ ppm, CDCl$_3$) 165.7, 161.6, 159.7, 151.9, 148.1, 143.0, 138.8, 134.7, 133.6, 131.6, 430.9, 129.2, 128.3, 127.9, 127.8, 127.7, 125.0, 122.4, 120.1, 114.7, 109.9, 55.6, 43.1.

Example 26

Preparation of 3-(4-methoxyphenyl)-5-phenyl-N-{4-[(pyrimidin-2-ylamino)carbonyl]benzyl}-1H-pyrrole-2-carboxamide

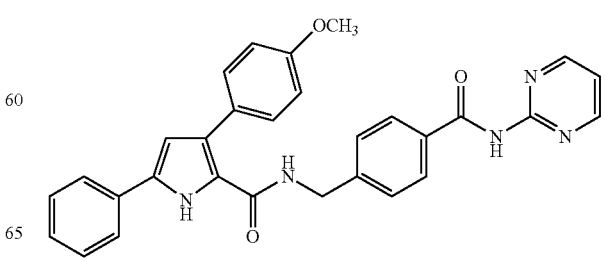

This material was prepared using a method substantially similar to that of Example 5 from 3-(4-methoxyphenyl)-5-phenyl-1H-pyrrole-2-carboxylic acid and 4-(aminomethyl)-N-pyrimidin-2-ylbenzamide hydrochloride, yielding the title compound. 3-(4-Methoxyphenyl)-5-phenyl-N-{4-[(pyrimidin-2-ylamino)carbonyl]benzyl}-1H-pyrrole-2-carboxamide: Yield 58%; m.p. 190-191° C.; IR 3396, 3251, 1623, 1571, 1525, 1429, 1243 cm$^{-1}$; $^{1}$H-NMR (300 MHz, δ ppm, CDCl$_3$) 9.72 (s, 1H), 8.83 (s, 1H), 8.66 (d, J=4.9 Hz, 2H), 7.88 (d, J=8.3 Hz, 3H), 7.57 (d, J=7.1 Hz, 2H), 7.44-7.23 (m, 6H), 7.06 (t, J=4.9 Hz, 1H), 6.90 (d, J=8.7 Hz, 2H), 6.49 (d, J=3.1 Hz, 1H), 6.12 (t, J=5.8 Hz, 1H), 4.51 (d, J=5.9 Hz, 2H), 3.82 (s, 3H); $^{1}$C-NMR (75 MHz, δ ppm, CDCl$_3$) 164.9, 161.6, 159.7, 158.7, 158.2, 143.1, 134.7, 133.6, 131.6, 130.9, 129.2, 128.4, 128.2, 127.9, 127.6, 125.0, 122.3, 117.1, 114.7, 109.9, 55.6, 43.1.

Example 27

Preparation of 3-(3-furyl)-N-{4-[(hydroxyamino)carbonyl]benzyl}-5-(4-methoxyphenyl)-1H-pyrrole-2-carboxamide

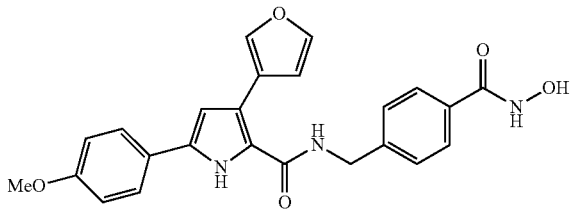

This material was prepared using a method substantially similar to that of Example 9, yielding the title compound. Yield 75%; m.p. 189-190° C.; IR 3390, 3292, 1626, 1600, 1534, 1435, 1258 cm$^{-1}$; $^{1}$H-NMR (500 MHz, δ ppm, DMSO-d$_6$) 11.33 (s, 1H), 11.18 (s, 1H), 8.99 (s, 1H), 8.42 (s, 1H), 8.27 (s, 1H), 7.73 (d, J=8.1 Hz, 4H), 7.63 (s, 1H), 7.43 (d, J=7.9 Hz, 2H), 7.01 (d, J=8.4 Hz, 2H), 6.91 (s, 1H), 6.78 (s, 1H), 4.53 (d, J=5.3 Hz, 2H), 3.80 (s, 3H); $^{13}$C-NMR (126 MHz, δ ppm, DMSO-d$_6$) 164.1, 160.8, 158.52, 142.9, 142.2, 141.0, 133.5, 131.3, 127.2, 126.9, 126.0, 124.1, 121.3, 120.4, 119.6, 114.2, 111.4, 106.8, 55.2, 42.1.

Example 28

Preparation of N-{4-[(hydroxyamino)carbonyl]benzyl}-5-(4-methoxyphenyl)-3-(3-thienyl)-1H-pyrrole-2-carboxamide

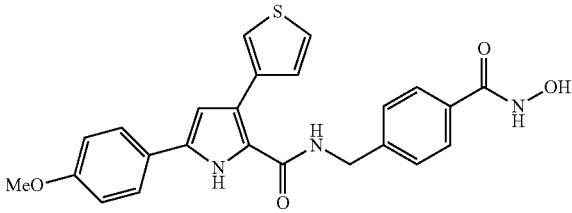 [SMILES: COc1ccc(-c2cc(-c3ccsc3)c(C(=O)NCc3ccc(C(=O)NO)cc3)[nH]2)cc1]

This material was prepared using a method substantially similar to that of Example 9, yielding the title compound. Yield 70%; m.p. 185 (dec.)° C.; IR 3384, 3303, 1619, 1612, 1530, 1434, 1254 cm$^{-1}$; $^{1}$H-NMR (300 MHz, δ ppm, DMSO-d$_6$) 11.42 (s, 1H), 8.27 (t, J=5.0 Hz, 1H), 7.80 (s, 1H), 7.73 (dd, J=8.1 Hz, J'=4.0 Hz, 4H), 7.49-7.35 (m, 4H), 6.99 (d, J=8.6 Hz, 2H), 6.72 (s, 1H), 4.49 (d, J=5.2 Hz, 2H), 3.79 (s, 3H); $^{13}$C-NMR (126 MHz, δ ppm, DMSO-d$_6$) 164.1, 161.2, 158.5, 142.9, 135.9, 133.3, 131.3, 129.2, 127.3, 126.9, 126.1, 124.7, 124.3, 123.8, 122.1, 121.9, 114.2, 107.5, 55.2, 42.2.

Example 29

Preparation of 3-(4-fluorophenyl)-N-{4-[(hydroxyamino)carbonyl]benzyl}-5-phenyl-1H-pyrrole-2-carboxamide

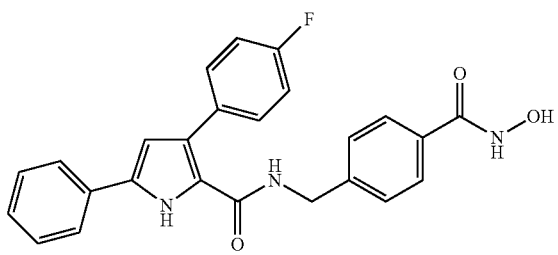 [SMILES: O=C(NO)c1ccc(CNC(=O)c2[nH]c(-c3ccccc3)cc2-c2ccc(F)cc2)cc1]

This material was prepared using a method substantially similar to that of Example 9, yielding the title compound. Yield 85%; m.p. 215-216° C.; IR 3404, 3296, 1619, 1614, 1523, 1439, 1258 cm$^{-1}$; $^{1}$H-NMR (500 MHz, δ ppm, DMSO-d$_6$) 11.85 (s, 1H), 11.17 (s, 1H), 8.97 (s, 1H), 8.57 (t, J=5.4 Hz, 1H), 8.17 (d, J=8.5 Hz, 2H), 7.80 (t, J=8.9 Hz, 4H), 7.73 (d, J=8.0 Hz, 2H), 7.45-7.40 (m, 4H), 7.29 (t, J=7.2 Hz, 1H), 6.91 (d, J=1.9 Hz, 1H), 4.48 (d, J=5.6 Hz, 2H); $^{13}$C-NMR (126 MHz, δ ppm, DMSO-d$_6$) 164.9, 161.8, 146.4, 143.7, 143.4, 134.4, 132.3, 132.1, 130.3, 130.2, 129.7, 128.3, 128.0, 127.8, 126.8, 125.6, 125.3, 123.9, 109.1, 43.2.

Example 30

Preparation of 3,5-bis-(4-fluorophenyl)-N-{4-[(hydroxyamino)carbonyl]benzyl}-1H-pyrrole-2-carboxamide

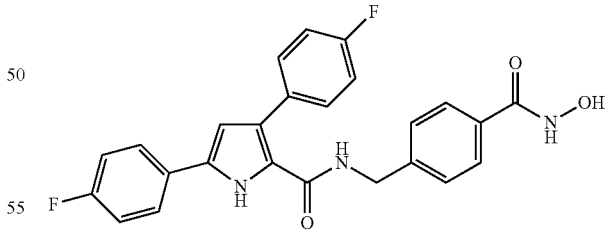

This material was prepared using a method substantially similar to that of Example 9, yielding the title compound. Yield 62%; m.p. 219-220° C.; IR 3430, 3269, 1668, 1633, 1523, 1498, 1267 cm$^{-1}$; $^{1}$H-NMR (500 MHz, δ ppm, DMSO-d$_6$) 11.62 (s, 1H), 11.18 (s, 1H), 8.99 (s, 1H), 8.17 (t, J=5.0 Hz, 1H), 7.83 (dd, J=6.9 Hz, J'=5.9 Hz, 2H), 7.71 (d, J=7.7 Hz, 2H), 7.52 (dd, J=6.9 Hz, J'=5.9 Hz, 2H), 7.37 (d, J=7.9 Hz, 2H), 7.26 (t, J=8.4 Hz, 2H), 7.14 (t, J=8.5 Hz, 2H), 6.70 (s, 1H), 4.44 (d, J=5.2 Hz, 2H); $^{13}$C-NMR (126 MHz, δ ppm, DMSO-d$_6$) 164.0, 162.2, 161.9, 160.9, 160.2, 160.0, 142.6, 132.1, 131.8, 131.3, 130.6, 129.2, 128.1, 127.4, 127.2, 127.1, 126.8, 126.6, 126.5, 122.9, 115.6, 115.4, 114.6, 114.4, 108.3, 42.1.

Example 31

Preparation of 3-(4-fluorophenyl)-N-{4-[(hydroxyamino)carbonyl]benzyl}-5-(2-thienyl)-1H-pyrrole-2-carboxamide

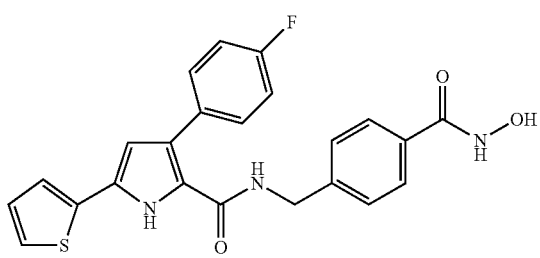 [SMILES: O=C(NO)c1ccc(CNC(=O)c2[nH]c(-c3cccs3)cc2-c2ccc(F)cc2)cc1]

This material was prepared using a method substantially similar to that of Example 9, yielding the title compound. Yield 31%; m.p. 214-216° C.; IR 3430, 3356, 1667, 1632, 1523, 1419, 1267 cm$^{-1}$; $^1$H-NMR (200 MHz, δ ppm, DMSO-d$_6$) 11.78 (s, 1H), 11.19 (s, 1H), 9.01 (s, 1H), 8.13 (t, J=5.3 Hz, 1H), 7.71 (d, J=8.1 Hz, 2H), 7.54-7.45 (m, 4H), 7.35 (d, J=8.1 Hz, 2H), 7.17-7.07 (m, 3H), 6.47 (s, 1H), 4.43 (d, J=5.5 Hz, 2H); $^{13}$C-NMR (126 MHz, δ ppm, DMSO-d$_6$) 164.6, 162.4, 161.5, 160.4, 142.5, 134.4, 131.5, 130.6, 130.6, 129.2, 127.9, 127.8, 127.4, 127.3, 127.1, 126.9, 126.8, 124.4, 123.1, 122.6, 114.6, 114.5, 108.4, 42.1.

Example 32

Preparation of 3-(4-fluorophenyl)-N-{2-[(hydroxyamino)carbonyl]-5-pyridyl-methyl}-5-(2-thienyl)-1H-pyrrole-2-carboxamide

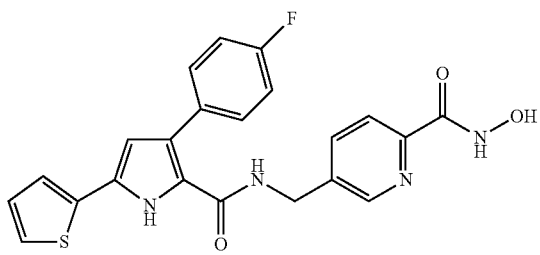 [SMILES: O=C(NO)c1ccc(CNC(=O)c2[nH]c(-c3cccs3)cc2-c2ccc(F)cc2)cn1]

This material was prepared using a method substantially similar to that of Example 9, yielding the title compound. Yield 24%; m.p. 189-191° C.; IR 3411, 3226, 1616, 1538, 1502, 1421, 1293, 1221, 1020 cm$^{-1}$; $^1$H-NMR (500 MHz, δ ppm, DMSO-d$_6$) 11.71 (s$_b$, 1H), 11.40 (s$_b$, 1H), 9.01 (s$_b$, 1H), 8.54 (s, 1H), 8.17 (s, 1H), 7.95-7.91 (m, 1H), 7.86 (d, J=6.5 Hz, 1H), 7.52-7.43 (m, 4H), 7.15-7.07 (m, 4H), 6.48 (s, 1H), 4.47 (s, 2H); $^{13}$C-NMR (126 MHz, δ ppm, DMSO-d$_6$) 162.0, 161.1, 160.1, 158.9, 148.7, 147.8, 137.6, 137.2, 136.5, 134.4, 131.4, 130.6, 130.5, 127.9, 127.0, 124.4, 123.2, 122.5, 121.4, 114.7, 114.5, 108.4, 107.5, 40.1.

Example 33

Preparation of N-(4-{[(2-aminophenyl)amino)carbonyl]benzyl}-5-(4-hydroxyphenyl)-3-(3-thienyl)-1H-pyrrole-2-carboxamide

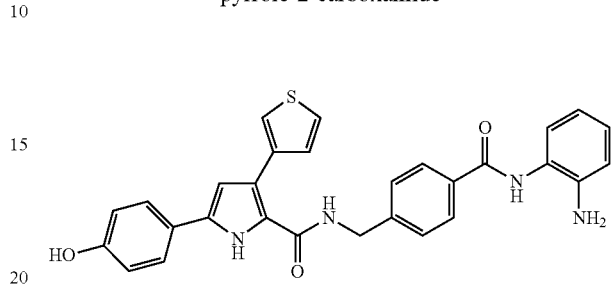

This material was prepared using a method substantially similar to that of Example 21, yielding the title compound. Yield 20%; IR 3370, 3256, 1643, 1613, 1501, 1450, 1259 cm$^{-1}$; $^1$H-NMR (500 MHz, δ ppm, DMSO-d$_6$) 11.25 (s, 1H), 9.60 (s, 1H), 9.52 (s, 1H), 8.19 (t, J=5.8 Hz, 1H), 7.95 (d, J=8.2 Hz, 2H), 7.82 (dd, J=2.7 Hz, J'=1.3 Hz, 1H), 7.60 (d, J=8.6 Hz, 2H), 7.48-7.43 (m, 4H), 7.17 (d, J=7.0 Hz, 1H), 6.96 (t, J=7.1 Hz, 1H), 6.84-6.76 (m, 3H), 6.65 (d, J=2.6 Hz, 1H), 6.60 (t, J=7.6 Hz, 1H), 4.86 (s, 2H), 4.53 (d, J=5.6 Hz, 2H); $^{13}$C-NMR (126 MHz, δ ppm, DMSO-d$_6$) 172.5, 161.0, 158.5, 149.5, 141.3, 139.6, 138.7, 132.2, 128.9, 128.4, 128.3, 128.2, 127.3, 127.0, 125.5, 125.1, 124.7, 123.0, 122.8, 122.6, 118.9, 116.4, 114.5, 113.2, 43.7.

Example 34

Preparation of N-(4-{[(2-aminophenyl)amino)carbonyl]benzyl}-5-(3-furyl)-3-(4-hydroxyphenyl)-1H-pyrrole-2-carboxamide

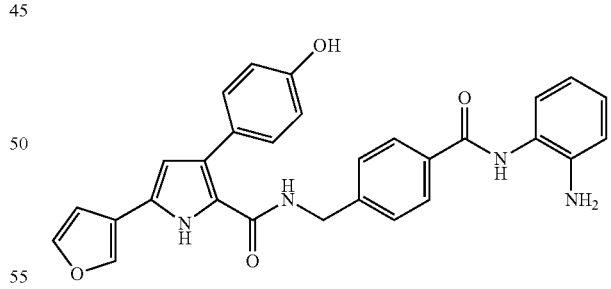

This material was prepared using a method substantially similar to that of Example 21, yielding the title compound. Yield 50%; m.p. 70-72° C.; IR 3397, 3223, 1621, 1522, 1450, 1265 cm$^{-1}$; $^1$H-NMR (300 MHz, δ ppm, DMSO-d$_6$) 11.53 (s, 1H), 9.60 (s, 1H), 9.40 (s, 1H), 8.14 (s, 1H), 7.93 (d, J=8.2 Hz, 2H), 7.68 (t, J=1.7 Hz, 1H), 7.36 (d, J=8.3 Hz, 3H), 7.28 (d, J=8.5 Hz, 2H), 7.17 (d, J=6.9 Hz, 1H), 7.02-6.91 (m, 2H), 6.77 (t, J=8.1 Hz, 3H), 6.60 (t, J=7.5 Hz, 1H), 6.39 (d, J=2.6 Hz, 1H), 4.86 (s, 2H), 4.45 (d, J=5.9 Hz, 2H); $^{13}$C-NMR (126 MHz, δ ppm, DMSO-d$_6$) 172.5, 161.0, 158.5, 149.5, 144.1, 141.3, 139.5, 138.7, 138.5, 132.2, 130.1, 129.3, 127.3, 127.0, 125.5, 125.1, 124.2, 122.8, 119.3, 118.9, 116.4, 114.5, 111.1, 108.8, 43.7.

Example 35

Preparation of N-(4-{[(2-Aminophenyl)amino)carbonyl]benzyl}-5-(4-hydroxyphenyl)-3-phenyl-1H-pyrrole-2-carboxamide

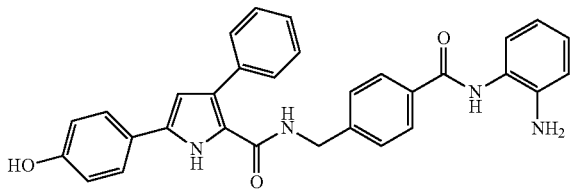

This material was prepared using a method substantially similar to that of Example 21, yielding the title compound. Yield 25%; m.p. 241-242° C.; IR 3372, 3266, 1640, 1625, 1566, 1449, 1258 cm$^{-1}$; $^1$H-NMR (300 MHz, δ ppm, DMSO-d$_6$) 11.37 (s, 1H), 9.60 (s, 1H), 9.50 (s, 1H), 8.00 (t, J=5.8 Hz, 1H), 7.94 (d, J=8.2 Hz, 2H), 7.61 (d, J=8.7 Hz, 2H), 7.51 (d, J=7.0 Hz, 2H), 7.41 (d, J=8.2 Hz, 2H), 7.33 (t, J=7.3 Hz, 2H), 7.26 (t, J=1.3 Hz, 1H), 7.17 (d, J=7.0 Hz, 1H), 7.02-6.93 (m, 1H), 6.84-6.75 (m, 3H), 6.60 (td, J=7.7 Hz, J'=1.2 Hz, 1H), 6.54-6.49 (m, 1H), 4.86 (s$_b$, 2H), 4.48 (d, J=5.5 Hz, 2H); $^{13}$C-NMR (126 MHz, δ ppm, DMSO-d$_6$) 165.3, 161.6, 157.2, 149.5, 143.3, 136.3, 134.2, 133.6, 129.4, 128.9, 128.3, 128.2, 127.6, 127.1, 126.9, 126.6, 123.8, 123.3, 122.3, 119.3, 116.8, 116.6, 115.9, 107.5, 42.6.

Example 36

Preparation of N-(4-{[(2-aminophenyl)amino)carbonyl]benzyl}-3-(4-hydroxyphenyl)-5-(3-thienyl)-1H-pyrrole-2-carboxamide

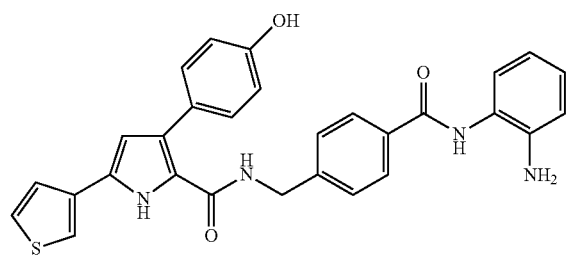 [SMILES: Nc1ccccc1NC(=O)c1ccc(CNC(=O)c2[nH]c(-c3ccoc3)cc2-c2ccc(O)cc2)cc1]

This material was prepared using a method substantially similar to that of Example 21, yielding the title compound. Yield 15%; m.p. 135-137° C.; IR 3528, 3229, 1732, 1612, 1524, 1449, 1263 cm$^{-1}$; $^1$H-NMR (300 MHz, δ ppm, DMSO-d$_6$) 11.54 (s, 1H), 9.60 (s, 1H), 9.37 (s, 1H), 8.15-8.07 (m, 1H), 7.93 (d, J=8.2 Hz, 2H), 7.90-7.87 (m, 1H), 7.59-7.51 (m, 2H), 7.38 (d, J=8.2 Hz, 2H), 7.30 (d, J=8.5 Hz, 2H), 7.18 (dd, J=7.9, 1.2 Hz, 1H), 7.01-6.93 (m, 1H), 6.80 (d, J=1.3 Hz, 1H), 6.75 (d, J=8.6 Hz, 2H), 6.60 (td, J=7.6 Hz, J'=1.4 Hz, 1H), 6.51 (d, J=2.6 Hz, 1H), 4.88 (s$_b$, 2H), 4.47 (d, J=5.7 Hz, 2H); $^{13}$C-NMR (126 MHz, δ ppm, DMSO-d$_6$) 165.6, 161.8, 156.8, 143.5, 143.4, 133.8, 133.6, 130.5, 130.1, 128.2, 127.6, 127.54, 127.1, 127.0, 126.9, 126.5, 126.3, 125.3, 123.8, 122.0, 119.3, 116.7, 116.6, 115.5, 109, 42.6.

Example 37

Preparation of N-(4-{[(2-aminophenyl)amino)carbonyl]benzyl}-3-(3-furyl)-5-(4-hydroxyphenyl)-1H-pyrrole-2-carboxamide

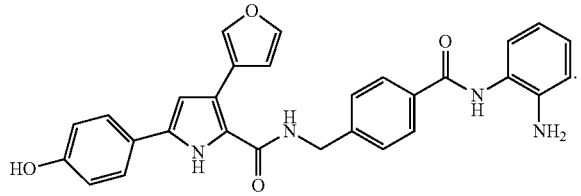 [SMILES: Nc1ccccc1NC(=O)c1ccc(CNC(=O)c2[nH]c(-c3ccc(O)cc3)cc2-c2ccoc2)cc1]

This material was prepared using a method substantially similar to that of Example 21, yielding the title compound. Yield 23%; IR 3387, 3221, 1641, 1523, 1450, 1257 cm$^{-1}$; $^1$H-NMR (500 MHz, δ ppm, DMSO-d$_6$) 11.24 (s, 1H), 9.60 (s, 1H), 9.55 (s, 1H), 8.18 (t, J=5.8 Hz, 1H), 7.95 (d, J=8.2 Hz, 2H), 7.69 (d, J=1.8 Hz, 1H), 7.49 (d, J=8.3 Hz, 2H), 7.41 (d, J=8.1 Hz, 2H), 7.37-7.33 (m, 2H), 7.17 (d, J=7.0 Hz, 2H), 6.86 (d, J=1.4 Hz, 2H), 6.79 (d, J=8.6 Hz, 2H), 6.60 (t, J=7.6 Hz, 1H), 4.86 (s, 2H), 4.51 (d, J=5.7 Hz, 2H); $^{13}$C-NMR (126 MHz, δ ppm, DMSO-d$_6$) 167.5, 161.3, 158.5, 149.5, 144.1, 141.3, 138.7, 138.5, 132.2, 129.3, 128.9, 128.4, 127.3, 127.0, 125.5, 125.1, 123.0, 122.8, 122.6, 118.9, 116.4, 114.5, 113.2, 109.8, 42.7.

Example 38

Preparation of N-{4-[(hydroxyamino)carbonyl]benzyl}-3-(4-methoxyphenyl)-5-phenyl-1H-pyrrole-2-carboxamide

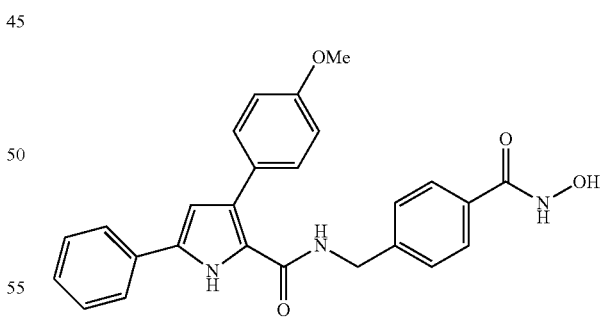

This material was prepared using a method substantially similar to that of Example 9, yielding the title compound. Yield 90%; m.p. 187-188° C.; IR 3394, 3198, 1636, 1612, 1526, 1493, 1243 cm$^{-1}$; $^1$H-NMR (500 MHz, δ ppm, DMSO-d$_6$) 11.51 (s, 1H), 11.15 (s, 1H), 8.94 (s, 1H), 7.91 (t, J=5.7 Hz, 1H), 7.79 (d, J=7.8, 2H), 7.71 (d, J=8.1 Hz, 2H), 7.46-7.33 (m, 6H), 7.25 (t, J=7.2 Hz, 1H), 6.88 (d, J=8.6 Hz, 2H), 6.66 (d, J=8.6 Hz, 1H), 4.44 (d, J=5.7 Hz, 2H), 3.76 (s, 3H); $^{13}$C-NMR (75 MHz, δ ppm, DMSO-d$_6$) 163.0, 161.0, 160.6, 141.3, 139.5, 138.7, 132.2, 131.2, 129.7, 129.2, 128.7, 127.5, 127.3, 127.0, 123.9, 119.3, 114.8, 111.1, 55.8, 43.7.

Example 39

Preparation of N-{4-[(hydroxyamino)carbonyl]benzyl}-5-phenyl-3-(4-trifluoromethylphenyl)-1H-pyrrole-2-carboxamide

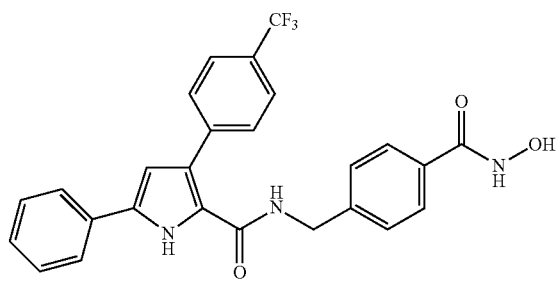

This material was prepared using a method substantially similar to that of Example 9, yielding the title compound. Yield 17%; m.p. 137-138° C.; IR 3431, 3355, 1622, 1620, 1533, 1321, 1121 cm$^{-1}$; $^1$H-NMR (500 MHz, δ ppm, DMSO-d$_6$) 11.82 (s, 1H), 11.17 (s, 1H), 8.99 (s, 1H), 8.52 (s, 1H), 7.82 (d, J=7.1 Hz, 2H), 7.73 (d, J=7.0 Hz, 4H), 7.66 (d, J=7.5 Hz, 2H), 7.42 (dd, J=17.0 Hz, J'=8.3 Hz, 4H), 7.29 (t, J=6.8 Hz, 1H), 6.83 (s, 1H), 4.47 (d, J=4.5 Hz, 2H); $^{13}$C-NMR (75 MHz, δ ppm, DMSO-d$_6$) 163.5, 161.0, 141.3, 139.9, 138.7, 133.3, 132.2, 131.4, 131.0, 129.3, 128.8, 127.8, 127.4, 127.3, 126.9, 125.6, 123.7, 119.3, 108.3, 42.3.

Example 40

Preparation of 3-(4-bromophenyl)-N-{4-[(hydroxyamino)carbonyl]benzyl}-5-phenyl-1H-pyrrole-2-carboxamide

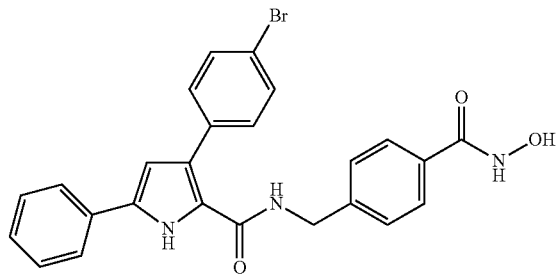

This material was prepared using a method substantially similar to that of Example 9, yielding the title compound. Yield 28%; m.p. 174-176° C.; IR 3427, 3218, 1630, 1624, 1534, 1487, 130 cm$^{-1}$; $^1$H-NMR (500 MHz, δ ppm, CDCl$_3$) 11.67 (s, 1H), 11.17 (s, 1H), 8.97 (s, 1H), 8.32 (s, 1H), 7.79 (d, J=7.7 Hz, 2H), 7.72 (d, J=8.1 Hz, 2H), 7.56-7.43 (m, 4H), 7.43-7.32 (m, 4H), 7.27 (t, J=7.3 Hz, 1H), 6.75 (s, 1H), 4.46 (d, J=5.6 Hz, 2H); $^{13}$C-NMR (126 MHz, δ ppm, DMSO-d$_6$) 164.0, 160.9, 142.6, 139.5, 138.7, 133.1, 131.4, 130.8, 129.7, 129.2, 128.7, 127.5, 127.3, 126.9, 123.1, 121.7, 119.3, 108.1, 43.1.

Example 41

Preparation of N-{4-[(hydroxyamino)carbonyl]benzyl}-3-(3,4-dimethoxyphenyl)-5-phenyl-1H-pyrrole-2-carboxamide

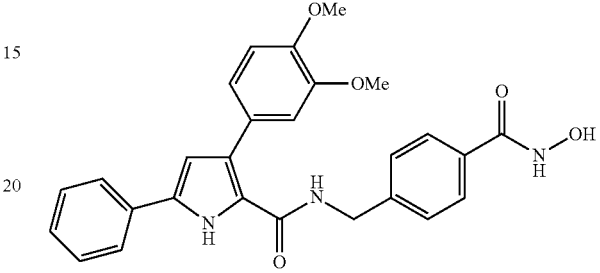

This material was prepared using a method substantially similar to that of Example 9, yielding the title compound. Yield 18%; m.p. 134-136° C.; IR 3396, 3295, 1631, 1628, 1530, 1501, 1260 cm$^{-1}$; $^1$H-NMR (500 MHz, δ ppm, CDCl$_3$) 11.56 (s, 1H), 11.16 (s, 1H), 8.96 (s, 1H), 7.87 (t, J=5.9 Hz, 1H), 7.81 (d, J=7.9 Hz, 2H), 7.70 (d, J=8.1 Hz, 2H), 7.39 (t, J=7.6 Hz, 2H), 7.35 (d, J=8.1 Hz, 2H), 7.25 (t, J=7.6 Hz, 1H), 7.12 (d, J=1.1 Hz, 1H), 7.02 (dd, J=8.2 Hz, J'=1.4 Hz, 1H), 6.90 (d, J=8.3 Hz, 1H), 6.70 (d, J=2.4 Hz, 1H), 4.44 (d, J=5.5 Hz, 2H), 3.76 (s, 3H), 3.69 (s, 3H); $^{13}$C-NMR (75 MHz, δ ppm, DMSO-d$_6$) 163.3, 161.2, 150.3, 149.8, 141.3, 139.5, 138.7, 132.9, 131.6, 129.7, 129.2, 128.6, 127.5, 127.1, 126.7, 122.8, 120.9, 113.6, 111.7, 108.8, 55.5, 55.3, 42.2.

Example 42

Preparation of 3-(3,4-difluorophenyl)-N-{4-[(hydroxyamino)carbonyl]benzyl}-5-phenyl-1H-pyrrole-2-carboxamide

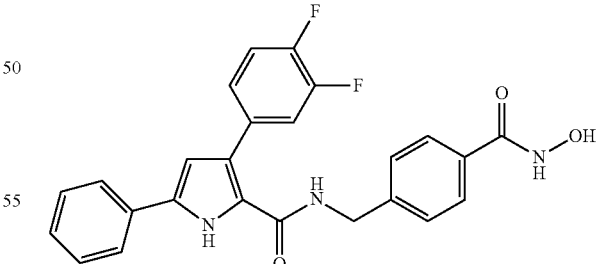

This material was prepared using a method substantially similar to that of Example 9, yielding the title compound. Yield 13%; m.p. 148-150° C.; IR 3431, 3349, 1634, 1603, 1527, 1495, 1275 cm$^{-1}$; $^1$H-NMR (300 MHz, δ ppm, DMSO-d$_6$) 11.65 (s, 1H), 11.15 (s, 1H), 8.97 (s, 1H), 8.37 (s, 1H), 7.79 (d, J=6.4 Hz, 2H), 7.72 (d, J=6.1 Hz, 2H), 7.65-7.52 (m, 1H), 7.45-7.33 (m, 5H), 7.28 (t, J=7.6 Hz, 1H), 6.79 (s, 1H), 4.47 (s, 2H); $^{13}$C-NMR (75 MHz, δ ppm, DMSO-d$_6$) 163.0, 161.0, 150.0, 149.5, 141.3, 139.5, 138.7, 133.6, 132.2, 131.2, 129.2, 128.7, 127.5, 127.3, 127.0, 126.4, 119.3, 118.6, 115.1, 111.1, 43.7.

Example 43

Preparation of N-{4-[(hydroxyamino)carbonyl]benzyl}-3-(4-nitrophenyl)-5-phenyl-1H-pyrrole-2-carboxamide

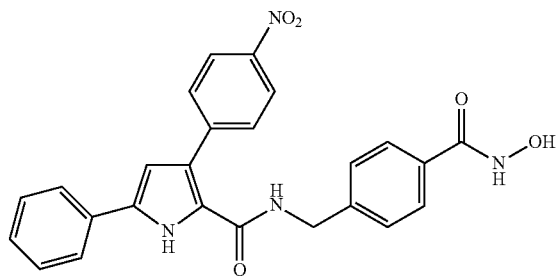

This material was prepared using a method substantially similar to that of Example 9, yielding the title compound. Yield 95%; m.p. 179-180° C.; IR 3390, 3230, 1634, 1595, 1514, 1339, 1149 cm$^{-1}$; $^1$H-NMR (500 MHz, δ ppm, DMSO-d$_6$) 11.59 (s, 1H), 11.16 (s, 1H), 8.96 (s, 1H), 8.19 (t, J=5.6 Hz, 1H), 7.79 (d, J=7.8 Hz, 2H), 7.72 (d, J=8.0 Hz, 2H), 7.53 (dd, J=8.1 Hz, 5.8 Hz, 2H), 7.44-7.34 (m, 4H), 7.27 (t, J=7.3 Hz, 1H), 7.13 (t, J=8.7 Hz, 2H), 6.72 (d, J=2.1 Hz, 1H), 4.45 (d, J=5.6 Hz, 2H); $^{13}$C-NMR (126 MHz, δ ppm, DMSO-d$_6$) 163.9, 161.8, 160.9, 159.9, 142.5, 132.9, 131.3, 130.6, 130.5, 128.6, 127.2, 126.8, 126.7, 124.5, 122.8, 114.5, 114.3, 108.3, 42.0.

Example 44

Preparation of 3-(3,4-dichlorophenyl)-N-{4-[(hydroxyamino)carbonyl]benzyl}-5-phenyl-1H-pyrrole-2-carboxamide

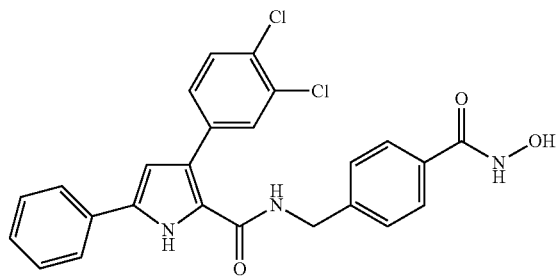

This material was prepared using a method substantially similar to that of Example 9, yielding the title compound. Yield 60%; m.p. 187-188° C.; IR 3398, 3202, 1630, 1618, 1534, 1481, 1296 cm$^{-1}$; $^1$H-NMR (500 MHz, δ ppm, DMSO-d$_6$) 11.70 (s, 1H), 11.17 (s, 1H), 8.97 (s, 1H), 8.44 (t, J=5.7 Hz, 1H), 7.80 (d, J=6.8 Hz, 2H), 7.73 (d, J=8.1 Hz, 2H), 7.55 (d, J=8.3 Hz, 1H), 7.50 (dd, J=8.4 Hz, J'=1.8 Hz, 1H), 7.44-7.39 (m, 5H), 7.28 (t, J=7.4 Hz, 1H), 6.84 (d, J=2.2 Hz, 1H), 4.47 (d, J=5.7 Hz, 2H); $^{13}$C-NMR (126 MHz, δ ppm, DMSO-d$_6$) 164.0, 160.9, 142.6, 136.3, 133.3, 131.3, 130.4, 130.3, 129.8, 128.9, 128.7, 128.5, 127.3, 127.0, 126.8, 125.7, 124.6, 123.4, 108.3, 42.2.

Example 45

Preparation of 3-(3-bromophenyl)-N-{4-[(hydroxyamino)carbonyl]benzyl}-5-phenyl-1H-pyrrole-2-carboxamide

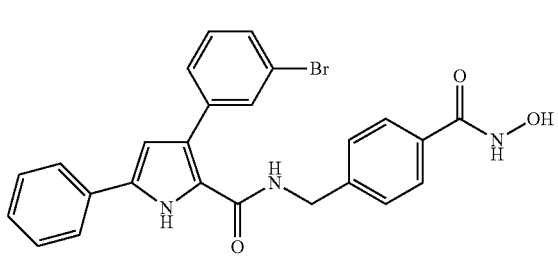 [SMILES: O=C(NO)c1ccc(CNC(=O)c2[nH]c(-c3ccccc3)cc2-c2cccc(Br)c2)cc1]

This material was prepared using a method substantially similar to that of Example 9, yielding the title compound. Yield 34%; m.p. 145-146° C.; IR 3418, 3259, 1632, 1616, 1536, 1483, 1294 cm$^{-1}$; $^1$H-NMR (500 MHz, δ ppm, DMSO-d$_6$) 11.69 (s, 1H), 11.18 (s, 1H), 8.97 (s, 1H), 8.37 (s, 1H), 7.81 (d, J=7.5 Hz, 2H), 7.73 (d, J=8.3 Hz, 2H), 7.51 (d, J=7.7 Hz, 1H), 7.46-7.36 (m, 5H), 7.28 (t, J=7.7 Hz, 2H), 6.81 (d, J=2.4 Hz, 1H), 6.81 (d, J=2.4 Hz, 1H), 4.47 (d, J=5.5 Hz, 2H); $^{13}$C-NMR (126 MHz, δ ppm, DMSO-d$_6$) 164.0, 161.0, 142.6, 138.0, 133.1, 131.2, 129.9, 128.8, 128.7, 127.7, 127.3, 126.9, 126.8, 126.5, 125.2, 124.6, 123.4, 121.2, 108.3, 42.2.

Example 46

Preparation of 3-(4-fluorophenyl)-N-{4-[(hydroxyamino)carbonyl]benzyl}-5-(3-pyridinyl)-1H-pyrrole-2-carboxamide

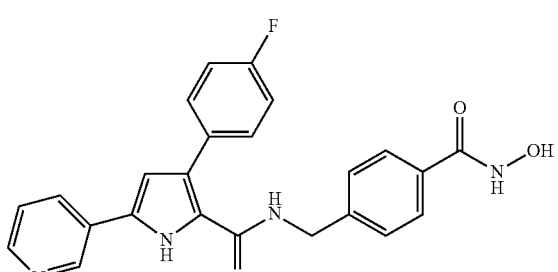

This material was prepared using a method substantially similar to that of Example 9, yielding the title compound. Yield 15%; IR 3406, 3283, 1733, 1630, 1522, 1438, 1258 cm$^{-1}$; $^1$H-NMR (500 MHz, δ ppm, DMSO-d$_6$) 11.78 (s, 1H), 11.19 (s, 1H), 9.00 (s, 1H), 8.11 (s, 1H), 7.71 (d, J=7.5 Hz, 2H), 7.52-7.43 (m, 5H), 7.37 (m, 2H), 7.15 (m, 3H), 6.50 (s, 1H), 4.49 (d, J=5.5 Hz, 2H); $^{13}$C-NMR (75 MHz, δ ppm, DMSO-$d_6$) 163.0, 162.9, 161.0, 147.9, 147.5, 141.3, 139.5, 138.7, 134.0, 133.0, 132.2, 130.8, 127.3, 127.2, 127.0, 124.0, 119.3, 116.0, 111.1, 43.7.

Example 47

Preparation of 3-(4-fluorophenyl)-N-{4-[(hydroxyamino)carbonyl]benzyl}-5-(4-methylphenyl)-1H-pyrrole-2-carboxamide

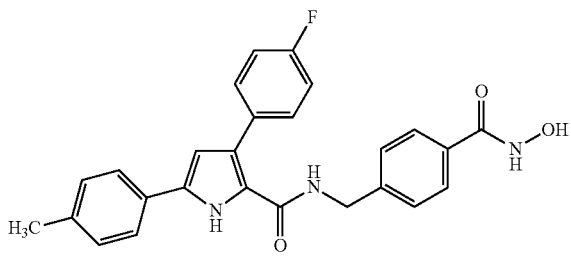 [SMILES: Cc1ccc(-c2cc(-c3ccc(F)cc3)c(C(=O)NCc3ccc(C(=O)NO)cc3)[nH]2)cc1]

This material was prepared using a method substantially similar to that of Example 9, yielding the title compound. Yield 26%; m.p. 213-215° C.; IR 3370, 3210, 1636, 1619, 1538, 1438, 1270 cm$^{-1}$; $^1$H-NMR (500 MHz, δ ppm, DMSO-$d_6$) 11.57 (s, 1H), 11.18 (s, 1H), 8.99 (s, 1H), 8.27 (s, 1H), 7.71 (m, 4H), 7.56-7.48 (m, 2H), 7.37 (d, J=7.8 Hz, 2H), 7.22 (d, J=7.8 Hz, 2H), 7.13 (t, J=8.6 Hz, 2H), 6.66 (s, 1H), 4.44 (d, J=5.5 Hz, 2H), 2.32 (s, 3H); $^{13}$C-NMR (126 MHz, δ ppm, DMSO-$d_6$) 164.0, 161.8, 160.9, 159.9, 142.6, 136.2, 133.1, 132.1, 131.2, 130.6, 129.2, 128.7, 127.5, 127.2, 126.8, 124.5, 122.4, 114.5, 114.3, 107.9, 42.0, 20.5.

Example 48

In vitro Inhibitory Activity of Histone Deacetylase: Rat Liver HDAC, Human Isoforms HDAC1, 2, 3, 4, 5, 6, 7, 8, 9, 10 and 11 and HeLa Cell Line Nuclear Extract (IC50 Data)

Components of Assay
Substrate peptides: All HDAC assays were performed using acetylated AMC-labeled peptide substrate:
  Substrate for isoforms HDAC1, 2, 3, 4, 5, 6, 7, 9, 10, 11 and HeLa nuclear extract assays: Acetylated fluorogenic peptide from p53 residues 379-382 (RHKKAc) (BioMol Cat. # KI-104).
  Substrate for HDAC8 assays: Acetylated fluorogenic peptide from p53 residues 379-382 (RHKAcKAc) (BioMol Cat. # KI-178).
  Substrate for rat liver HDAC assays: Acetylated fluorogenic peptide Boc-Lys(Ac)-AMC (Bachem, Switzerland, Cat. # I-1875).
Assay buffer: 50 mM Tris-HCl, pH 8.0, 137 mM NaCl, 2.7 mM KCl, 1 mM MgCl$_2$ (supplement with 1 mg/ml BSA for dilution) (BioMol Cat. # KI-143).
Enzymes:
  HDAC1 assay: 75 nM Human HDAC1 (GenBank Accession No. NM_004964): Full length with C-terminal GST tag, MW=79.9 kDa, expressed by baculovirus expression system in Sf9 cells (BioMol Cat. # SE-456).
  HDAC2 assay: 5 nM Human HDAC2 (GenBank Accession No. Q92769): Full length with C-terminal His tag, MW=60 kDa, expressed by baculovirus expression system in Sf9 cells (BioMol Cat. # SE-500).
  HDAC3 assay: 2.3 nM Human HDAC3/NcoR2 (GenBank Accession No. NM_003883 for HDAC3, GenBank Accession No. NM_006312 for NcoR2): Complex of human HDAC3, full length with C-terminal His tag, MW=49.7 kDa, and human NCOR2, N-terminal GST tag, MW=39 kDa, co-expressed in baculovirus expression system (BioMol Cat. # SE-507).
  HDAC4 assay: 266 nM Human HDAC4 (GenBank Accession No. NM_006037): Amino acids 627-1085 with N-terminal GST tag, MW=75.2 kDa, expressed in baculovirus expression system (BioMol, Hamburg, Germany).
  HDAC5 assay: 588 nM Human HDAC5 (GenBank Accession No. NM_001015053): Full length with Nterminal GST tag, MW=150 kDa, expressed by baculovirus expression system in Sf9 cells (BioMol, Hamburg, Germany).
  HDAC6 assay: 13 nM Human HDAC6 (GenBank Accession No. BC069243): Full length with N-terminal GST tag, MW=159 kDa, expressed by baculovirus expression system in Sf9 cells (BioMol Cat. # SE-508).
  HDAC7 assay: 962 nM Human HDAC7 (GenBank Accession No. AY302468): Amino acids 518-end with N-terminal GST tag, MW=78 kDa, expressed in baculovirus expression system (BioMol, Hamburg, Germany).
  HDAC8 assay: 119 nM Human HDAC8 (GenBank Accession No. NM018486): Full length, MW=42 kDa, expressed in an E. coli expression system (BioMol Cat. # SE-145).
  HDAC9 assay: 986 nM Human HDAC9 (GenBank Accession No. NM178423): Amino acids 604-1066 with C-terminal His tag, MW=50.7 kDa, expressed in baculovirus expression system (BioMol, Hamburg, Germany).
  HDAC10 assay: 781 nM Human HDAC10 (GenBank Accession No. NM_032019): Amino acids 1-631 with Nterminal GST tag, MW=96 kDa, expressed by baculovirus expression system in Sf9 cells (BioMol Cat. # SE-559).
  HDAC11 assay: 781 nM Human HDAC11 (GenBank Accession No. NM_BC009676) with N-terminal GST tag, MW=66 kDa, expressed in baculovirus expression system (BioMol Cat. # SE-560).
  HeLaNuclear Extract assay: 25 ng/µl Nuclear Extract from HeLa Cells: Prepared by high salt extraction of HeLa nuclei (human cervical cancer cell line), this extract is a rich source of HDAC activity (BioMol Cat. # KI-140).
  Rat liver HDAC assay: 7.8 ng/µl native, enzymatically active, partially purified histone deacetylase from rat liver (Calbiochem Cat. #382165)
Assay Procedure
  50 µM of substrate peptide (see 'substrate peptides' section above) and an optimal concentration of the corresponding enzyme (see 'enzymes' section above) in the assay buffer and 1% final concentration of DMSO were incubated in the presence of gradient concentrations of inhibitors (10-dose IC50 mode with 3-fold serial dilution) at 30° C. for 2 h. The reactions were carried out in a 96-well microplate for fluorometry in a 50 µl reaction volume. After the deacetylation reaction, Fluor-de-Lys-Developer (BioMol Cat. # KI-105) was added to each well to digest the deacetylated substrate, thus producing the fluorescent signal. The reaction was allowed to develop for 45 minutes at 30° C. with 5% CO$_2$; then the fluorescent signal was measured with an excitation wavelength at 360 nm and an emission wavelength at 460 nm in a microplate-reading fluorometer (GeminiXS; Molecular Devices, Sunnyvale, Calif.). A curve of Deacetylated Standard (Biomol, Cat. # KI-142; made from 100 μM with 1:2 dilution and 10-doses, 6 μl) allowed the conversion of fluorescent signal into micromoles of deacetylated product. All experiments were performed in triplicate. IC50 was calculated by fitting the experimental data to a dose-response curve. DMSO was used as negative control; Trichostatin A (Biomol Cat. # GR-309), SAHA (suberoylanilide hydroxamic acid, obtained in house) and Kendine 91 (IUPAC name: N-[6-(hydroxyamino)-6-oxohexyl]-3-(4-methoxyphenyl)-5-phenyl-1H-pyrrole-2-carboxamide, obtained in house) were used as positive control inhibitors.

| Human cancer | Cell line | Medium |
|---|---|---|
| Breast Cancer | BT474 | MEM |
|  | MCF-7 | MEM + 0.1 mM NEAA |
|  | MCF-7-218 | DMEM |
|  | MCF-7-FL | DMEM |
|  | MDA-MB-231 | L15 |
|  | SK-BR-3 | McCoys'5a |
| Prostate Cancer | DU145 | RPMI-1640 |
|  | LNCaP | RPMI-1640 |
|  | PC-3 | F12K |

| | IC50 (nM) of enzyme activity | | | | | | | | | | | | |
|---|---|---|---|---|---|---|---|---|---|---|---|---|---|
| Compound | HDAC1 | HDAC2 | HDAC3 | HDAC4 | HDAC5 | HDAC6 | HDAC7 | HDAC8 | HDAC9 | HDAC10 | HDAC11 | HeLa | Rat liver |
| SAHA | 254.2 | 1045 | 460.4 | — | — | 44.8 | — | 335.2 | — | — | — | 24.5 | — |
| Kendine 91 | 508.3 | 1690 | 612.9 | — | — | 34.9 | — | 146 | — | — | — | 43.0 | — |
| Example 9 | 378 | 909 | 298 | — | — | 6.8 | — | 227 | — | — | — | 26.0 | — |
| Example 10 | 473.1 | 1393 | 512.3 | — | — | 10.8 | — | 340.1 | — | — | — | 34.0 | 66 |
| Example 11 | 744.5 | 2529 | 753.7 | — | — | 52 | — | 180.6 | — | — | — | 68.3 | — |
| Example 12 | 383.7 | 1147 | 451.3 | — | — | 42.8 | — | 124.2 | — | — | — | 46.4 | 56 |
| Example 13 | 865 | 1909 | 614 | — | — | 6.6 | — | 559 | — | — | — | 42 | — |
| Example 14 | 84.2 | 317.8 | 123.9 | 956 | 172 | 0.44 | 692 | 64.1 | 277 | 316 | 319 | 6.7 | — |
| Example 15 | 49.9 | 144.4 | 46.1 | 338 | 60 | 0.7 | 178 | 74.8 | 59 | 35 | 72 | 3.4 | — |
| Example 16 | — | — | — | — | — | — | — | — | — | — | — | — | >10000 |
| Example 17 | — | — | — | — | — | — | — | — | — | — | — | — | 9790 |
| Example 18 | — | — | — | — | — | — | — | — | — | — | — | — | >10000 |
| Example 19 | — | — | — | — | — | — | — | — | — | — | — | — | 101 |
| Example 21 | 390 | 1265 | 3900 | — | — | >5000 | — | >5000 | — | — | — | 7010 | >10000 |
| Example 22 | >5000 | >5000 | >5000 | — | — | >5000 | — | >5000 | — | — | — | >5000 | >10000 |
| Example 23 | — | — | — | — | — | — | — | — | — | — | — | — | >10000 |
| Example 25 | >5000 | >5000 | >5000 | — | — | >5000 | — | >5000 | — | — | — | >5000 | — |
| Example 26 | >5000 | >5000 | >5000 | — | — | >5001 | — | >5001 | — | — | — | >5000 | — |
| Example 27 | 71 | 157 | 75 | 1083 | 222 | 1.6 | 290 | 148 | 163 | 294 | 341 | 3.9 | — |
| Example 28 | 184 | 392 | 273 | 2431 | 640 | 2 | 762 | 174 | 478 | 723 | 718 | 22 | — |
| Example 29 | — | — | — | — | — | — | — | — | — | — | — | 73 | 71 |
| Example 30 | — | — | — | — | — | — | — | — | — | — | — | 90 | 82 |
| Example 31 | — | — | — | — | — | — | — | — | — | — | — | 58 | 49 |
| Example 32 | — | — | — | — | — | — | — | — | — | — | — | 390 | — |
| Example 33 | 103 | 364 | 732 | — | — | >5000 | — | >5000 | — | — | — | 3270 | — |
| Example 34 | 86 | 349 | 770 | — | — | 1255 | — | >5000 | — | — | — | 1537 | — |
| Example 35 | 108 | 433 | 806 | — | — | >5000 | — | >5000 | — | — | — | 4277 | — |
| Example 36 | 222 | 752 | 2068 | — | — | >5000 | — | >5000 | — | — | — | 4079 | — |
| Example 37 | 332 | 1836 | 5830 | >5000 | 8644 | 2886 | >5000 | >5000 | >5000 | 8547 | 5662 | 1075 | — |
| Example 38 | — | — | — | — | — | — | — | — | — | — | — | — | 70 |
| Example 39 | — | — | — | — | — | — | — | — | — | — | — | — | 170 |
| Example 40 | — | — | — | — | — | — | — | — | — | — | — | — | 99 |
| Example 41 | — | — | — | — | — | — | — | — | — | — | — | — | 119 |
| Example 42 | — | — | — | — | — | — | — | — | — | — | — | — | 129 |
| Example 43 | — | — | — | — | — | — | — | — | — | — | — | — | 62 |
| Example 44 | — | — | — | — | — | — | — | — | — | — | — | — | 153 |
| Example 45 | — | — | — | — | — | — | — | — | — | — | — | — | 115 |
| Example 46 | — | — | — | — | — | — | — | — | — | — | — | — | 70 |
| Example 47 | — | — | — | — | — | — | — | — | — | — | — | — | 108 |

Example 49

Biological Activity in Cancer Cell Lines

Cell culture-based assays were used to evaluate the ability of compounds of the invention to inhibit cancer cell growth inhibition.

Cells were obtained from the American Type Culture Collection (ATCC). Cells were cultured at 37° C. with 5% $CO_2$ in the appropriate growth medium (see table below), and harvested respectively during the logarithmic growth period and counted with hemocytometer. The cell viability was over 98% by trypan blue exclusion. Cell concentrations were adjusted between $5 \times 10^4$ and $2 \times 10^5$ cells/ml with respective medium.

| Human cancer | Cell line | Medium |
|---|---|---|
| Colorectal Cancer | Colo205 | RPMI-1640 |
|  | DLD-1 | RPMI-1640 |
|  | HCT-116 | McCoys'5a |
|  | HT-29 | DMEM + F12 |
|  | LoVo | F12K |
|  | SW620 | L15 |
| Lung Cancer | A549 | F12K |
|  | Calu-6 | MEM + 0.1 mM NEAA |
|  | NCI-H226 | RPMI-1640 |
|  | NCI-H460 | RPMI-1640 |
|  | SK-MES-1 | MEM + 0.1 mM NEAA |
| Glioblastoma | U87MG | DMEM + 0.1 mM NEAA |
| Fibrosarcoma | HT-1080 | MEM + 0.1 mM NEAA |
| Pancreatic Cancer | MIAPACA-2 | DMEM |

| Human cancer | Cell line | Medium |
|---|---|---|
| | Bx-PC-3 | RPMI-1640 |
| | PANC-1 | DMEM |
| Kindney Cancer | 786-O | RPMI-1640 |
| Liver Cancer | Hep3B | DMEM + 0.1 mM NEAA |
| | HepG2 | DMEM |
| | SK-HEP-1 | MEM + 0.1 mM NEAA |
| Osteosarcoma | 143b | EMEM |
| Melanoma | A375 | DMEM |
| | SK-MEL-5 | MEM + 0.1 mM NEAA |
| Nasopharyngeal Cancer | CNE2 | DMEM (low glucose) |
| Gastric Cancer | MCG803 | DMEM (low glucose) |
| | BGC823 | RPMI-1640 |
| Ovarian Cancer | SK-OV-3 | McCoys'5a |
| | OVCAR3 | DMEM (low glucose) |
| CML | K562 | RPMI-1640 |
| Oral Cancer | KB | RPMI-1640 |
| Orthotopic Multiple Myeloma | RPMI-8226 | RPMI-1640 |

Stock solutions of test compounds and positive drugs Doxorubicin (Zhejiang, Haizheng, China), Paclitaxel (Beijing, Xiehe, China), Vincristin (Shenzhen Wanle, China), 5-FU (Tianjin jinyaoanjisuan, China), Irinotecan (Jiangsu Hengrui, China) and Cisplatin Nanjing zhiyao, China) were prepared in dimethyl sulphoxide (DMSO) or PBS at 20 mM.

In order to determine the 72 hour $IC_{50}$ for each compound, experiments were carried out in 96-well plates and the cell lines seeded at a density of 5,000 to 20,000 cells/well. In each cell line, 72 h treatment $IC_{50}$ values were determined for each compound using the MTD assay. All treatments were performed in triplicate. 10 μl drug solution was added to each well and incubated for 72 hours. At the end of the incubation, 20 μl of the freshly prepared MTS/PMS mixture solution was added to each well and incubated for 4 hours at 37° C. in a humidified, 5% $CO_2$ atmosphere. Absorbance was read at 490 nm using SpectraMAX Plus microplate spectrophotometer. For data analysis, data were displayed graphically using GraphPad Prism 5.0. In order to calculate $IC_{50}$, a dose-responsive curve was fitted using nonlinear regression model with a sigmoidal dose response.

| | | | $IC_{50}$ (μM) | | | | |
|---|---|---|---|---|---|---|---|
| Human cancer | Cell lines | Positive drug | | Examp 9 | Examp 14 | Examp 15 | Examp 27 | Examp 28 |
| Breast Cancer | BT474 | Doxorubicin | 4.502 | 3.632 | 1.626 | 0.4422 | 0.1191 | 12.94 |
| | MCF-7 | Cisplatin | 7.746 | 4.490 | 10.10 | 2.091 | 0.3765 | 2.765 |
| | MCF-7-218 | Paclitaxel | 0.2850 | 12.77 | 37.57 | 26.52 | — | — |
| | MCF-7- FL | Doxorubicin | 2.374 | 7.724 | 6.636 | 3.308 | — | — |
| | MDA-MB-231 | Cisplatin | 99.76 | 4.255 | 4.065 | 1.826 | 1.49 | 73.83 |
| | SK-BR-3 | Cisplatin | 1.738 | 1.495 | 0.3345 | 0.4529 | 0.7714 | 4.085 |
| Prostate Cancer | DU145 | Cisplatin | 4.009 | 4.514 | 1.519 | 0.4601 | 0.3385 | 1.862 |
| | LNCaP | Cisplatin | 8.920 | 9.910 | 4.109 | 1.720 | 0.3659 | 3.066 |
| | PC-3 | Cisplatin | 11.48 | 3.000 | 2.405 | 0.2806 | 0.4196 | 1.312 |
| Colorectal Cancer | Colo205 | Irinotecan | 16.64 | 4.914 | 1.563 | 0.3651 | 0.2482 | 3.099 |
| | DLD-1 | Cisplatin | 18.29 | 6.867 | 24.52 | 4.483 | 0.5917 | 3.221 |
| | HCT-116 | 5-FU | 1.708 | 1.993 | 0.08038 | 0.08197 | 0.4161 | 1.461 |
| | HT-29 | Cisplatin | 14.93 | 10.67 | 5.781 | 2.294 | 1.015 | 25.88 |
| | LoVo | Cisplatin | 4.645 | 1.908 | 0.4977 | 0.1500 | 0.4301 | 3.854 |
| | SW480 | Cisplatin | 10.76 | — | — | — | 0.5742 | 2.375 |
| | SW620 | Cisplatin | 84.28 | 1.822 | 1.531 | 0.3341 | 0.3771 | 1.997 |
| Lung Cancer | A549 | Cisplatin | 28.41 | 11.39 | 10.97 | 2.462 | 1.021 | 3.434 |
| | Calu-6 | Cisplatin | 1.612 | 9.605 | 4.067 | 1.217 | 0.4924 | 0.7259 |
| | NCI-H226 | Cisplatin | 9.501 | 11.90 | 21.30 | 3.052 | 1.765 | 12.56 |
| | NCI-H460 | Cisplatin | 6.93 | 10.48 | 26.68 | 6.292 | 1.682 | 12.11 |
| | SK-MES-1 | Cisplatin | 5.123 | 7.762 | 18.53 | 3.512 | 0.5878 | 1.776 |
| Glioblastoma | U87MG | Cisplatin | 7.611 | 10.79 | 9.354 | 6.559 | 1.391 | 8.963 |
| Fibrosarcoma | HT-1080 | Doxorubicin | 0.02565 | 1.837 | 1.528 | 0.5939 | 0.1605 | 1.093 |
| Pancreatic Cancer | MIAPACA-2 | 5-FU | 7.614 | 2.814 | 0.4282 | 0.27 | 0.8808 | 7.518 |
| | Bx-PC-3 | Cisplatin | 6.118 | 7.726 | 6.834 | 2.250 | 0.7753 | 8.279 |
| | PANC-1 | Cisplatin | 24.83 | 10.73 | 9.844 | 6.445 | 0.9651 | 11.48 |
| Kindney Cancer | 786-O | Cisplatin | 4.323 | 13.43 | 8.658 | 2.290 | 1.91 | 10.03 |
| Liver Cancer | Hep3B | Cisplatin | 3.959 | 3.179 | 2.699 | 0.8592 | 0.6136 | 4.271 |
| | HepG2 | 5-FU | 3.277 | 5.009 | 2.008 | 2.28 | 0.4982 | 1.772 |
| | SK-HEP-1 | Doxorubicin | 0.1645 | 4.471 | 1.754 | 0.4502 | 1.096 | 9.926 |
| Osteosarcoma | 143b | Doxorubicin | 0.08614 | 12.87 | 2.621 | 1.933 | 2.573 | 11.07 |
| Melanoma | A375 | Cisplatin | 6.553 | 10.20 | 7.696 | 3.684 | 1.036 | 4.271 |
| | SK-MEL-5 | Cisplatin | 2.871 | 3.335 | 0.8512 | 0.2925 | 0.2555 | 3.786 |
| Nasopharyngeal Cancer | CNE2 | Cisplatin | 11.80 | 9.537 | 11.39 | 16.15 | 0.5903 | 5.014 |
| Gastric Cancer | MCG803 | Cisplatin | 11.38 | 1.099 | 3.274 | 2.009 | 0.738 | 6.082 |
| | NCI-N87 | Cisplatin | 8.242 | — | — | — | 0.1531 | 1.48 |
| | BGC823 | Cisplatin | 1.293 | 9.675 | 13.73 | 5.136 | 0.6761 | 7.795 |
| Ovarian Cancer | SK-OV-3 | Cisplatin | 4.425 | 4.17 | 1.628 | 0.6513 | 1.666 | 8.433 |
| | OVCAR3 | Cisplatin | 11.68 | 9.989 | 25.25 | 8.048 | 0.9042 | 4.764 |
| CML | K562 | Cisplatin | 13.16 | 1.044 | 1.300 | 0.7391 | 0.3068 | 1.374 |
| Oral Cancer | KB | Cisplatin | 3.969 | 2.960 | 0.7021 | 0.1836 | 0.3151 | 3.425 |
| Orthotopic Multiple Myeloma | RPMI-8226 | Cisplatin | 1.059 | 1.311 | 0.3361 | 0.4263 | 0.05857 | 0.4621 |

The invention claimed is:

1. A compound of general formula (I)

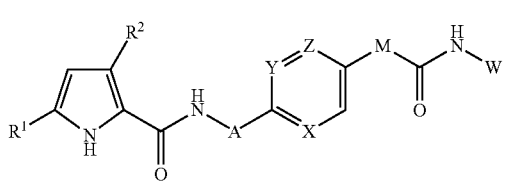

wherein:
- R[1] and R[2] represent, independently of each other, an optionally substituted $C_6$-$C_{10}$ aryl radical or an optionally substituted heteroaryl radical;
- A and M represent, independently of each other, a methylene group or a single bond, in which case the adjacent aromatic ring would be attached directly to the amide group;
- the Y=Z group represents together and indistinctly an oxygen atom (—O—), a sulfur atom (—S—), a cis-vinylidene group (—CH=CH—), an imino group (—N=CH— or —CH=N—), or a methine group with a $sp^2$-hybridized carbon atom (=CH—);
- X represents indistinctly a methine group (=CH—), a cis-vinylidene group (—CH=CH—) or a nitrogen atom (=N—); and
- W represents a hydroxyl group (—OH), an optionally substituted $C_1$-$C_6$ alkyl group, an optionally substituted heteroaryl group or an optionally substituted $C_6$-$C_{10}$ aryl group;

or a salt or solvate thereof.

2. Compound according to claim 1, wherein R[1] and R[2] represent, independently of each other, an optionally substituted phenyl group or an optionally substituted 5 or 6 membered heteroaryl group.

3. Compound according to claim 1, wherein at least one of the groups A or M is a methylene group or a single bond.

4. Compound according to claim 1, wherein Y=Z and X form together with the carbon atoms to which they are attached, a phenyl, a pyridine, a pyrazine or a furan ring.

5. Compound according to claim 1, wherein W represents a hydroxyl group, an optionally substituted $C_1$-$C_3$ alkyl group, an optionally substituted 5 or 6 membered heteroaryl group, or an optionally substituted phenyl group.

6. Compound according to claim 1, selected from the group consisting of:

[1] 5-(3-Furyl)-N-{4-[(hydroxyamino)carbonyl]benzyl}-3-(4-hydroxyphenyl)-1H-pyrrole-2-carboxamide, with the following structural formula:

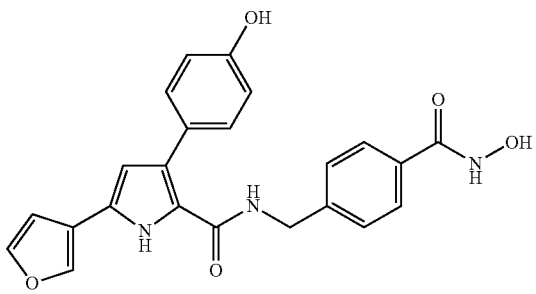 [SMILES: O=C(NO)c1ccc(CNC(=O)c2[nH]c(-c3ccoc3)cc2-c2ccc(O)cc2)cc1]

[2] N-{4-[(Hydroxyamino)carbonyl]benzyl}-3-(4-hydroxyphenyl)-5-phenyl-1H-pyrrole-2-carboxamide, with the following structural formula:

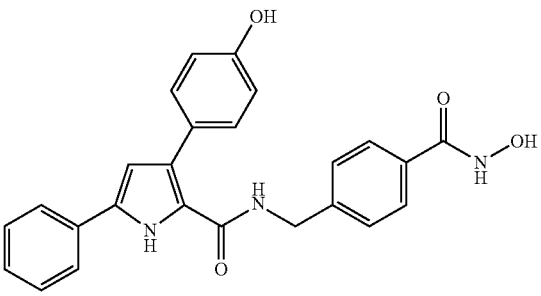 [SMILES: O=C(NO)c1ccc(CNC(=O)c2[nH]c(-c3ccccc3)cc2-c2ccc(O)cc2)cc1]

[3] 6-[({[3-(4-Fluorophenyl)-5-(2-thienyl)-1H-pyrrol-2-yl]carbonyl}amino)methyl]-N-hydroxynicotinamide, with the following structural formula:

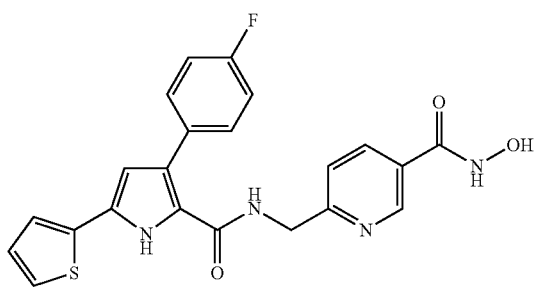 [SMILES: O=C(NO)c1ccc(CNC(=O)c2[nH]c(-c3cccs3)cc2-c2ccc(F)cc2)nc1]

[4] 3-(4-Fluorophenyl)-5-(3-furyl)-N-{4-[(hydroxyamino)carbonyl]benzyl}-1H-pyrrole-2-carboxamide, with the following structural formula:

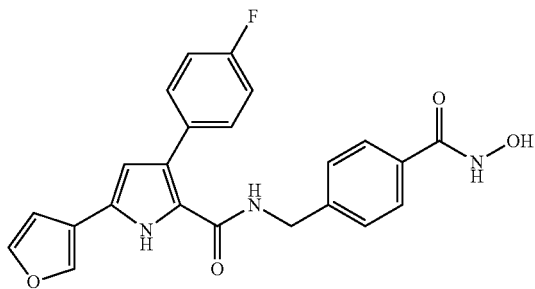 [SMILES: O=C(NO)c1ccc(CNC(=O)c2[nH]c(-c3ccoc3)cc2-c2ccc(F)cc2)cc1]

[5] N-{4-[(Hydroxyamino)carbonyl]benzyl}-3-(4-hydroxyphenyl)-5-(2-thienyl)-1H-pyrrole-2-carboxamide, with the following structural formula:

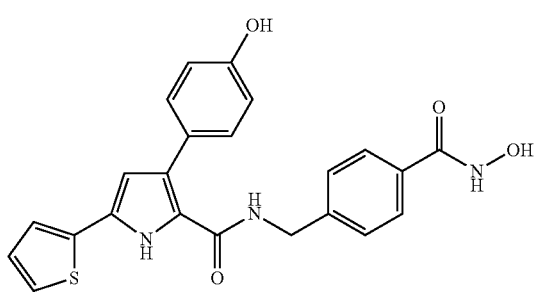 [SMILES: O=C(NO)c1ccc(CNC(=O)c2[nH]c(-c3cccs3)cc2-c2ccc(O)cc2)cc1]

[6] N-{5-[(Hydroxyamino)carbonyl]-2-furyl}-3-(4-methoxyphenyl)-5-phenyl-1H-pyrrole-2-carboxamide, with the following structural formula:

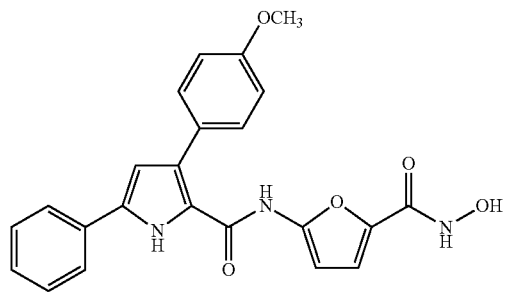 [SMILES: COc1ccc(-c2cc(-c3ccccc3)[nH]c2C(=O)Nc2ccc(C(=O)NO)o2)cc1]

[7] 3-(4-Fluorophenyl)-N-({5-[(hydroxyamino)carbonyl]-2-furyl}methyl)-5-phenyl-1H-pyrrole-2-carboxamide, with the following structural formula:

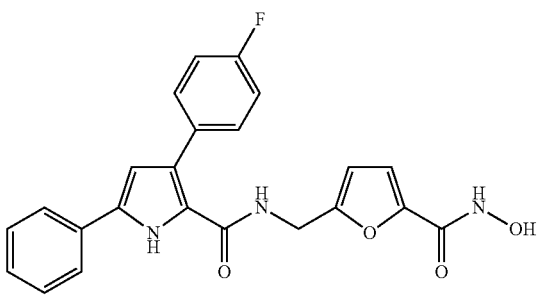 [SMILES: O=C(NO)c1ccc(CNC(=O)c2[nH]c(-c3ccccc3)cc2-c2ccc(F)cc2)o1]

[8] N-{3-[2-(hydroxyamino)-2-oxoethyl]phenyl}-3-(4-methoxyphenyl)-5-phenyl-1H-pyrrole-2-carboxamide, with the following structural formula:

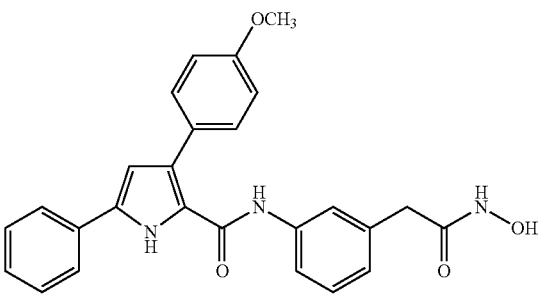 [SMILES: COc1ccc(-c2cc(-c3ccccc3)[nH]c2C(=O)Nc2cccc(CC(=O)NO)c2)cc1]

[9] N-{4-[(Hydroxyamino)carbonyl]benzyl}-5-(4-hydroxyphenyl)-3-(3-thienyl)-1H-pyrrole-2-carboxamide, with the following structural formula:

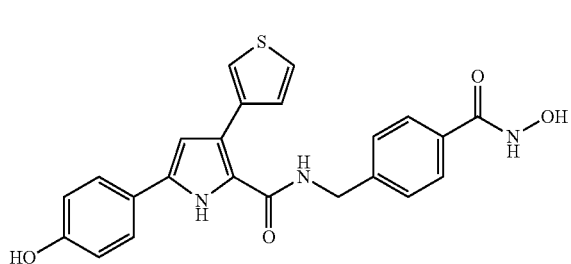

[10] 3-(3-Furyl)-N-{4-[(hydroxyamino)carbonyl]benzyl}-5-(4-hydroxyphenyl)-1H-pyrrole-2-carboxamide, with the following structural formula:

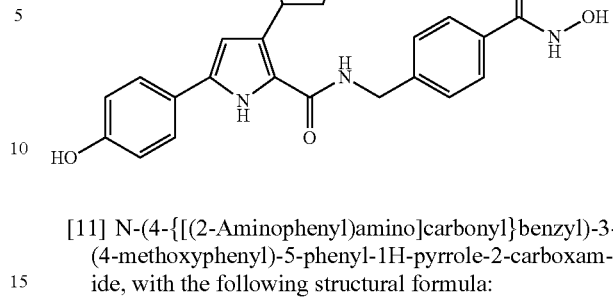

[11] N-(4-{[(2-Aminophenyl)amino]carbonyl}benzyl)-3-(4-methoxyphenyl)-5-phenyl-1H-pyrrole-2-carboxamide, with the following structural formula:

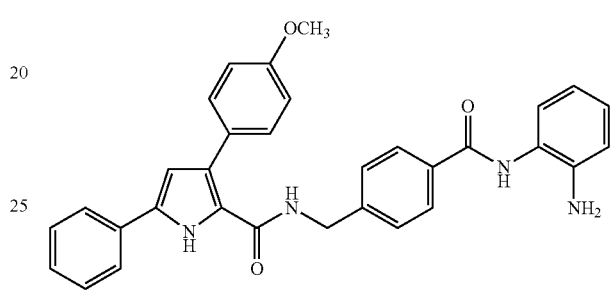

[12] 3-(4-Methoxyphenyl)-5-phenyl-N-(4-{[(2-sulfanylphenyl)amino]carbonyl}benzyl)-1H-pyrrole-2-carboxamide, with the following structural formula:

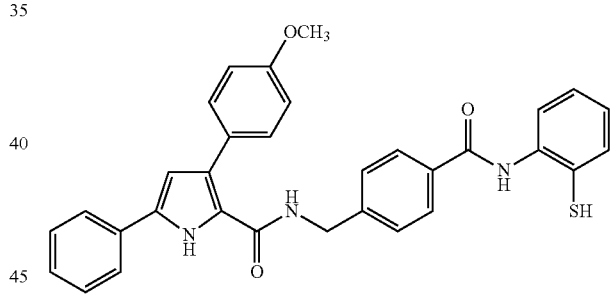

[13] 3-(4-Methoxyphenyl)-5-phenyl-N-(4-{[(2-sulfanylethyl)amino]carbonyl}benzyl)-1H-pyrrole-2-carboxamide, with the following structural formula:

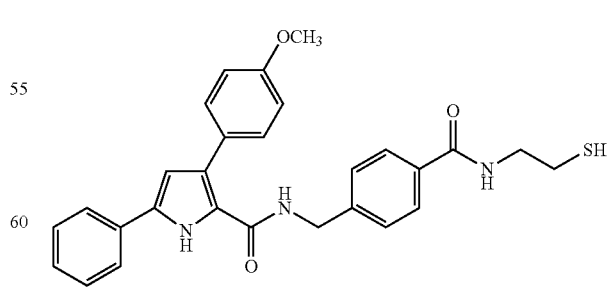

[14] 3-(4-Methoxyphenyl)-5-phenyl-N-{4-[(pyridin-2-ylamino)carbonyl]benzyl}-1H-pyrrole-2-carboxamide, with the following structural formula:

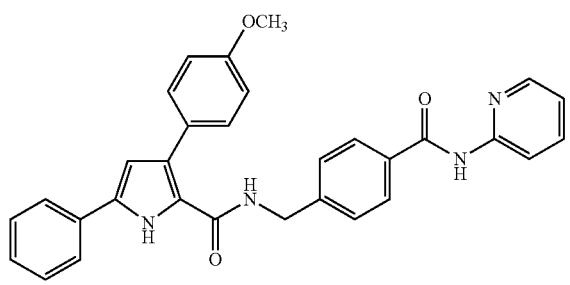 [SMILES: COc1ccc(-c2cc(-c3ccccc3)[nH]c2C(=O)NCc2ccc(C(=O)Nc3ccccn3)cc2)cc1]

[15] 3-(4-Methoxyphenyl)-5-phenyl-N-{4-[(pyrimidin-2-ylamino)carbonyl]benzyl}-1H-pyrrole-2-carboxamide, with the following structural formula:

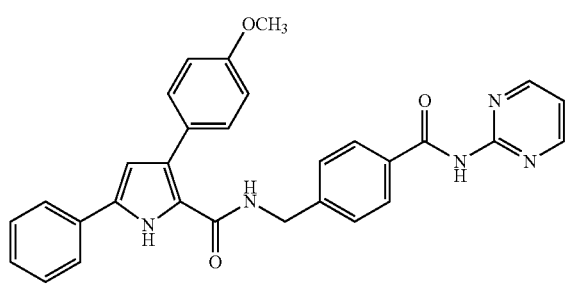 [SMILES: COc1ccc(-c2cc(-c3ccccc3)[nH]c2C(=O)NCc2ccc(C(=O)Nc3ncccn3)cc2)cc1]

[16] N-{4-[(hydroxyamino)carbonyl]phenyl}-3-(4-methoxyphenyl)-5-phenyl-1H-pyrrole-2-carboxamide, with the following structural formula:

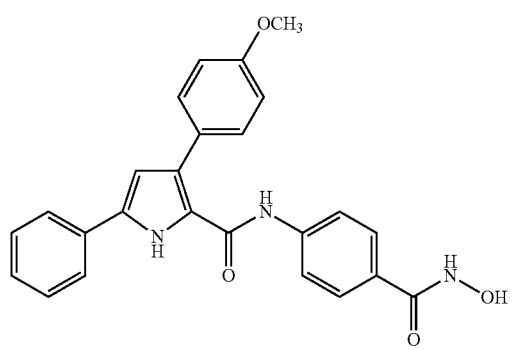 [SMILES: COc1ccc(-c2cc(-c3ccccc3)[nH]c2C(=O)Nc2ccc(C(=O)NO)cc2)cc1]

[17] 3-(3-Furyl)-N-{4-[(hydroxyamino)carbonyl]benzyl}-5-(4-methoxyphenyl)-1H-pyrrole-2-carboxamide, with the following structural formula:

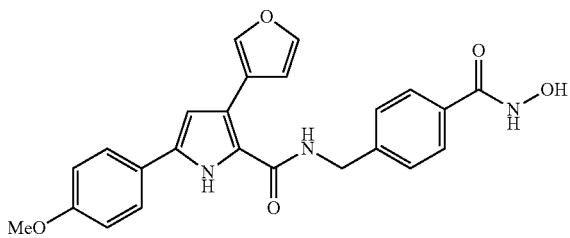 [SMILES: COc1ccc(-c2cc(-c3ccoc3)c(C(=O)NCc3ccc(C(=O)NO)cc3)[nH]2)cc1]

[18] N-{4-[(hydroxyamino)carbonyl]benzyl}-5-(4-methoxyphenyl)-3-(3-thienyl)-1H-pyrrole-2-carboxamide, with the following structural formula:

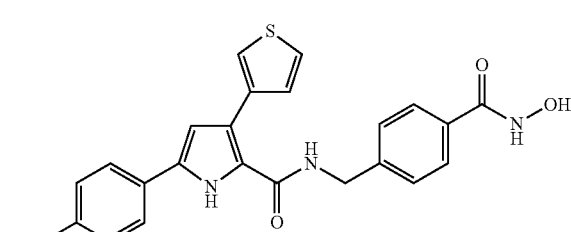

[19] 3-(4-Fluorophenyl)-N-{4-[(hydroxyamino)carbonyl]benzyl}-5-phenyl-1H-pyrrole-2-carboxamide, with the following structural formula:

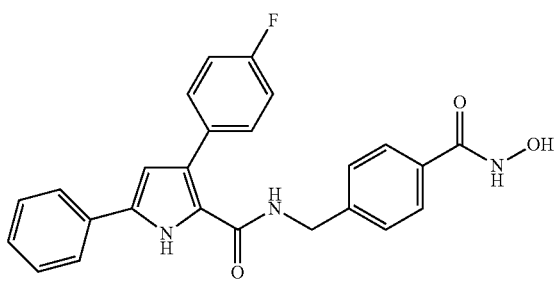 [SMILES: O=C(NO)c1ccc(CNC(=O)c2[nH]c(-c3ccccc3)cc2-c2ccc(F)cc2)cc1]

[20] 3,5-Bis-(4-fluorophenyl)-N-{4-[(hydroxyamino)carbonyl]benzyl}-1H-pyrrole-2-carboxamide, with the following structural formula:

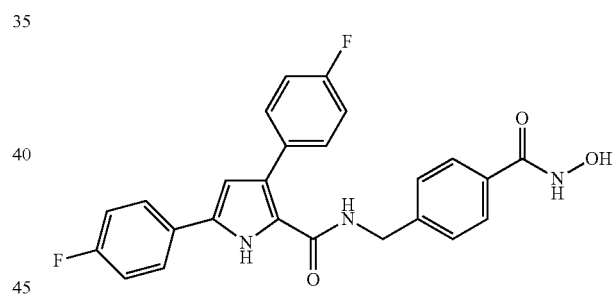

[21] 3-(4-Fluorophenyl)-N-{4-[(hydroxyamino)carbonyl]benzyl}-5-(2-thienyl)-1H-pyrrole-2-carboxamide, with the following structural formula:

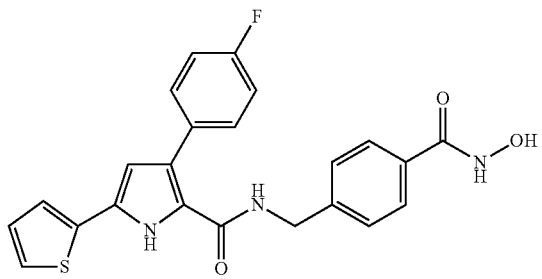

[22] 3-(4-Fluorophenyl)-N-{2-[(hydroxyamino)carbonyl]-5-pyridyl-methyl}-5-(2-thienyl)-1H-pyrrole-2-carboxamide, with the following structural formula:

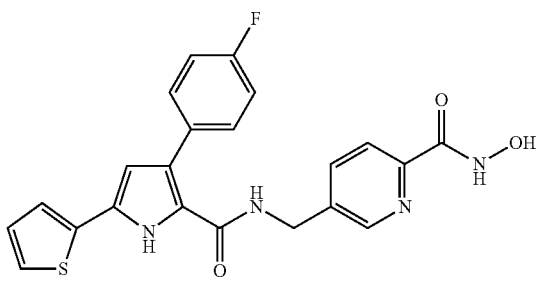 [SMILES: O=C(NO)c1ccc(CNC(=O)c2[nH]c(-c3cccs3)cc2-c2ccc(F)cc2)cn1]

[23] N-(4-{[(2-Aminophenyl)amino)carbonyl]benzyl}-5-(4-hydroxyphenyl)-3-(3-thienyl)-1H-pyrrole-2-carboxamide, with the following structural formula:

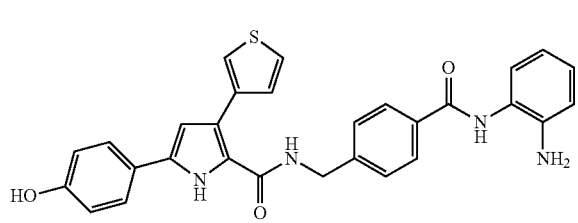 [SMILES: Nc1ccccc1NC(=O)c1ccc(CNC(=O)c2[nH]c(-c3ccc(O)cc3)cc2-c2ccsc2)cc1]

[24] N-(4-{[(2-Aminophenyl)amino)carbonyl]benzyl}-5-(3-furyl)-3-(4-hydroxyphenyl)-1H-pyrrole-2-carboxamide, with the following structural formula:

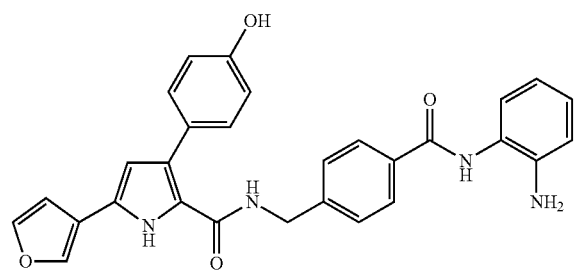

[25] N-(4-{[(2-Aminophenyl)amino)carbonyl]benzyl}-5-(4-hydroxyphenyl)-3-phenyl-1H-pyrrole-2-carboxamide, with the following structural formula:

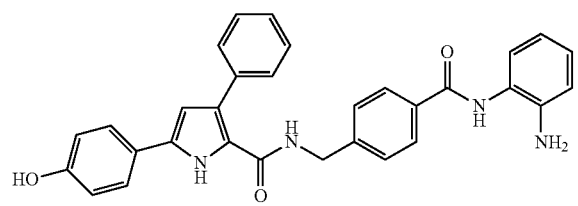 [SMILES: Nc1ccccc1NC(=O)c1ccc(CNC(=O)c2[nH]c(-c3ccc(O)cc3)cc2-c2ccccc2)cc1]

[26] N-(4-{[(2-Aminophenyl)amino)carbonyl]benzyl}-3-(4-hydroxyphenyl)-5-(3-thienyl)-1H-pyrrole-2-carboxamide, with the following structural formula:

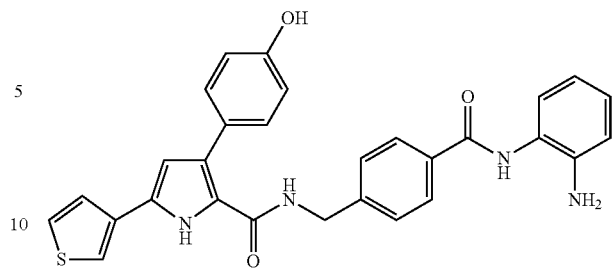

[27] N-(4-{[(2-Aminophenyl)amino)carbonyl]benzyl}-3-(3-furyl)-5-(4-hydroxyphenyl)-1H-pyrrole-2-carboxamide, with the following structural formula:

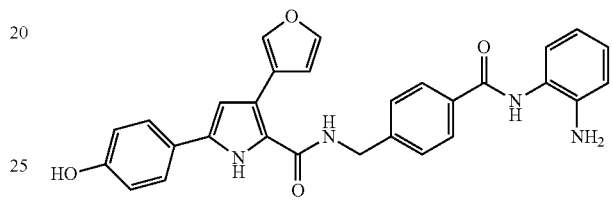

[28] N-{4-[(Hydroxyamino)carbonyl]benzyl}-3-(4-methoxyphenyl)-5-phenyl-1H-pyrrole-2-carboxamide, with the following structural formula:

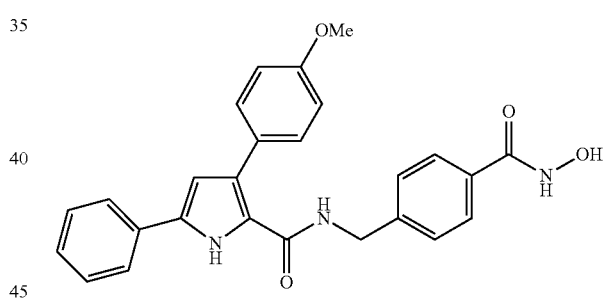

[29] N-{4-[(Hydroxyamino)carbonyl]benzyl}-5-phenyl-3-(4-trifluoromethylphenyl)-1H-pyrrole-2-carboxamide, with the following structural formula:

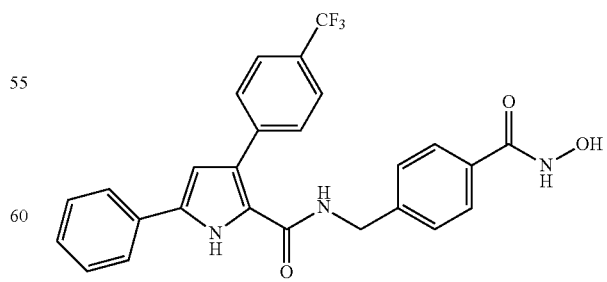

[30] 3-(4-Bromophenyl)-N-{4-[(Hydroxyamino)carbonyl]benzyl}-5-phenyl-1H-pyrrole-2-carboxamide, with the following structural formula:

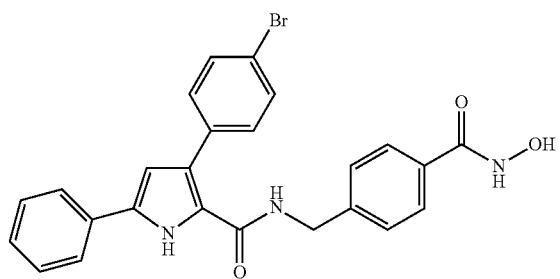

[31] N-{4-[(Hydroxyamino)carbonyl]benzyl}-3-(3,4-dimethoxyphenyl)-5-phenyl-1H-pyrrole-2-carboxamide, with the following structural formula:

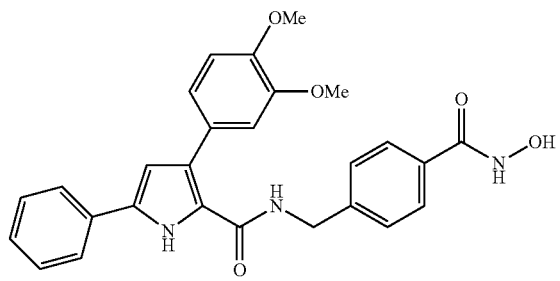 [SMILES: COc1ccc(-c2cc(-c3ccccc3)[nH]c2C(=O)NCc2ccc(C(=O)NO)cc2)cc1OC]

[32] 3-(3,4-Difluorophenyl)-N-{4-[(hydroxyamino)carbonyl]benzyl}-5-phenyl-1H-pyrrole-2-carboxamide, with the following structural formula:

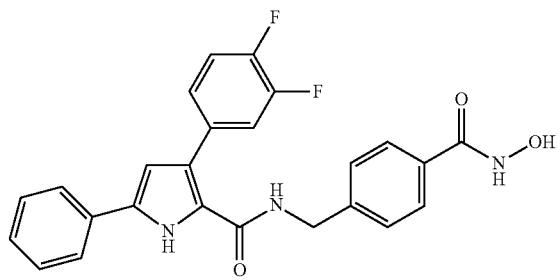

[33] N-{4-[(Hydroxyamino)carbonyl]benzyl}-3-(4-nitrophenyl)-5-phenyl-1H-pyrrole-2-carboxamide, with the following structural formula:

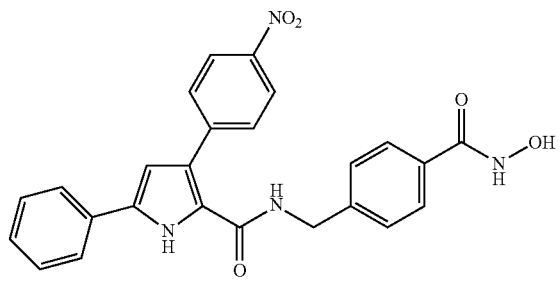

[34] 3-(3,4-Dichlorophenyl)-N-{4-[(hydroxyamino)carbonyl]benzyl}-5-phenyl-1H-pyrrole-2-carboxamide, with the following structural formula:

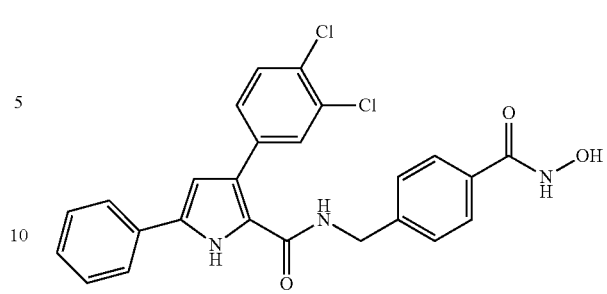

[35] 3-(3-Bromophenyl)-N-{4-[(hydroxyamino)carbonyl]benzyl}-5-phenyl-1H-pyrrole-2-carboxamide, with the following structural formula:

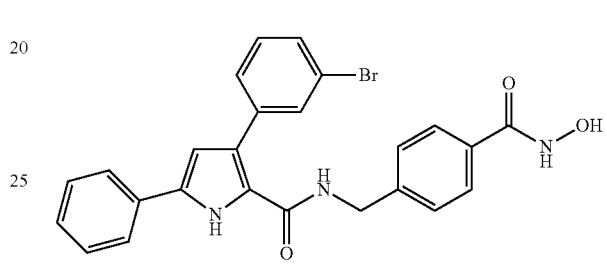

[36] 3-(4-Fluorophenyl)-N-{4-[(hydroxyamino)carbonyl]benzyl}-5-(3-pyridinyl)-1H-pyrrole-2-carboxamide, with the following structural formula:

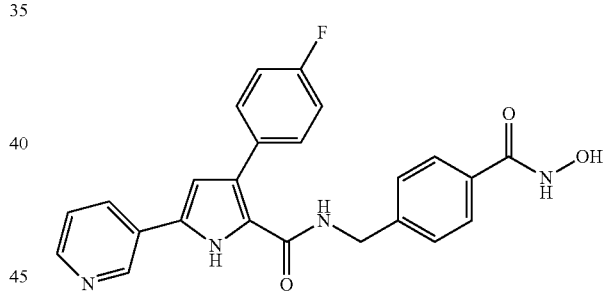

[37] 3-(4-Fluorophenyl)-N-{4-[(hydroxyamino)carbonyl]benzyl}-5-(4-methylphenyl)-1H-pyrrole-2-carboxamide, with the following structural formula:

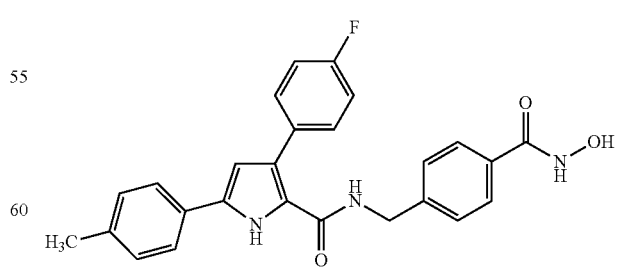

or a salt or solvate thereof.

7. A process for the preparation of a compound of general formula (I)

(I)

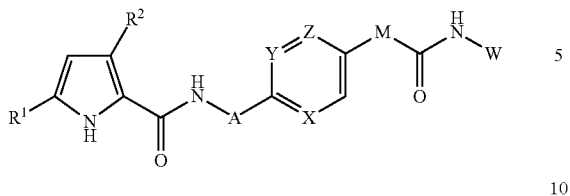

wherein:
- $R^1$ and $R^2$ represent, independently of each other, an optionally substituted $C_6$-$C_{10}$ aryl radical or an optionally substituted heteroaryl radical;
- A and M represent, independently of each other, a methylene group or a single bond, in which case the adjacent aromatic ring would be attached directly to the amide group;
- the Y=Z group represents together and indistinctly an oxygen atom (—O—), a sulfur atom (—S—), a cis-vinylidene group (—CH=CH—), an imino group (—N=CH— or —CH=N—), or a methine group with a sp²-hybridized carbon atom (=CH—);
- X represents indistinctly a methine group (=CH—), a cis-vinylidene group (—CH=CH—) or a nitrogen atom (=N—); and
- W represents a hydroxyl group (—OH), an optionally substituted $C_1$-$C_6$ alkyl group, an optionally substituted heteroaryl group or an optionally substituted $C_6$-$C_{10}$ aryl group;

or a salt or solvate thereof,
which comprises:
a) preparing a compound of general formula (IV);

(IV)

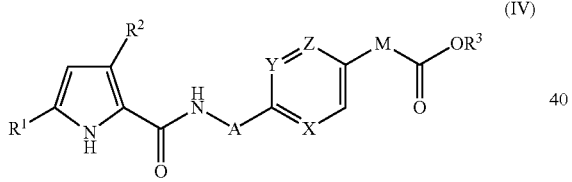

b) subjecting said compound of general formula (IV) to a hydrolysis reaction, to yield a compound of general formula (V):

(V)

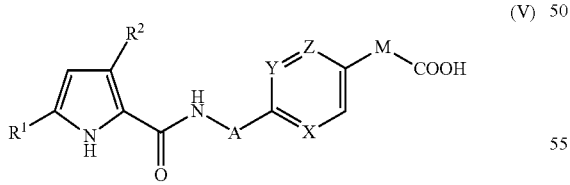

wherein $R^1$, $R^2$, A, M, X, Y and Z are those previously defined; and
c) reacting said compound of formula (V) with a compound of general formula (VI)

 (VI)

wherein W is that previously defined;
in the presence of a reagent for the activation of the carboxyl group, an organic solvent and a tertiary amine.

8. A process for the preparation of a compound of general formula (I)

(I)

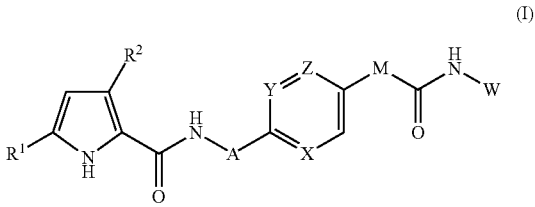

wherein:
- $R^1$ and $R^2$ represent, independently of each other, an optionally substituted $C_6$-$C_{10}$ aryl radical or an optionally substituted heteroaryl radical;
- A and M represent, independently of each other, a methylene group or a single bond, in which case the adjacent aromatic ring would be attached directly to the amide group;
- the Y=Z group represents together and indistinctly an oxygen atom (—O—), a sulfur atom (—S—), a cis-vinylidene group (—CH=CH—), an imino group (—N=CH— or —CH=N—), or a methine group with a sp²-hybridized carbon atom (=CH—);
- X represents indistinctly a methine group (=CH—), a cis-vinylidene group (—CH=CH—) or a nitrogen atom (=N—); and
- W represents a hydroxyl group (—OH), an optionally substituted $C_1$-$C_6$ alkyl group, an optionally substituted heteroaryl group or an optionally substituted $C_6$-$C_{10}$ aryl group;

or a salt or solvate thereof,
which comprises reacting a mixture comprising:
a) a compound of general formula (II)

(II)

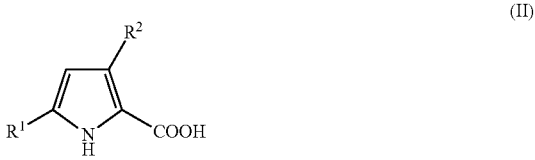

wherein $R^1$ and $R^2$ are those previously defined;
b) a compound of general formula (VII)

(VII)

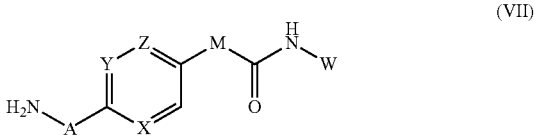

wherein A, M, X, Y, Z and W are those previously defined;
c) at least one reagent for the activation of the carboxyl group; and
d) a tertiary amine 9. A process according to claim 8, wherein the compound of general formula (II),

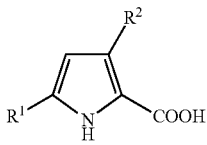

(II)

wherein:
R¹ and R² represent, independently of each other, an optionally substituted $C_6$-$C_{10}$ aryl radical or an optionally substituted heteroaryl radical;

is obtained by a process which comprises:
a) reacting a α,β-unsaturated carbonylic compound of formula (VIII)

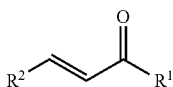

(VIII)

wherein R¹ and R² are those previously defined;
an ester of the nitroacetic acid of general formula (IX)

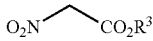

(IX)

wherein R³ is a $C_1$-$C_6$ alkyl group; and
a primary, secondary or tertiary amine, to obtain a compound of general formula (X)

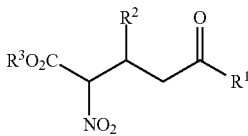

(X)

wherein R¹, R² and R³ are those previously defined;
b) subjecting said compound of formula (X) to an oxidation reaction to yield a compound of general formula (XI)

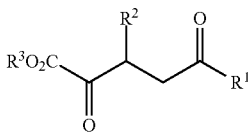

(XI)

wherein R¹, R² and R³ are those previously defined;
c) treating said compound of general formula (XI) with ammonium hydroxide or an ammonium salt of an aliphatic carboxylic acid of less than 5 carbon atoms, and subsequent alkaline hydrolysis.

10. A pharmaceutical composition that comprises at least a compound of formula (I) according to claim 1, or a pharmaceutically acceptable salt or solvate thereof, and a pharmaceutically acceptable excipient.

11. Compound according to claim 2, wherein at least one of the groups A or M is a methylene group or a single bond.

12. Compound according to claim 2, wherein Y=Z and X form together with the carbon atoms to which they are attached, a phenyl, a pyridine, a pyrazine or a furan ring.

13. Compound according to claim 3, wherein Y=Z and X form together with the carbon atoms to which they are attached, a phenyl, a pyridine, a pyrazine or a furan ring.

14. Compound according to claim 11, wherein Y=Z and X form together with the carbon atoms to which they are attached, a phenyl, a pyridine, a pyrazine or a furan ring.

15. Compound according to claim 2, wherein W represents a hydroxyl group, an optionally substituted $C_1$-$C_3$ alkyl group, an optionally substituted 5 or 6 membered heteroaryl group, or an optionally substituted phenyl group.

16. Compound according to claim 3, wherein W represents a hydroxyl group, an optionally substituted $C_1$-$C_3$ alkyl group, an optionally substituted 5 or 6 membered heteroaryl group, or an optionally substituted phenyl group.

17. Compound according to claim 4, wherein W represents a hydroxyl group, an optionally substituted $C_1$-$C_3$ alkyl group, an optionally substituted 5 or 6 membered heteroaryl group, or an optionally substituted phenyl group.

18. Compound according to claim 11, wherein W represents a hydroxyl group, an optionally substituted $C_1$-$C_3$ alkyl group, an optionally substituted 5 or 6 membered heteroaryl group, or an optionally substituted phenyl group.

19. Compound according to claim 13, wherein W represents a hydroxyl group, an optionally substituted $C_1$-$C_3$ alkyl group, an optionally substituted 5 or 6 membered heteroaryl group, or an optionally substituted phenyl group.

20. Compound according to claim 15, wherein W represents a hydroxyl group, an optionally substituted $C_1$-$C_3$ alkyl group, an optionally substituted 5 or 6 membered heteroaryl group, or an optionally substituted phenyl group.

21. Compound according to claim 16, wherein W represents a hydroxyl group, an optionally substituted $C_1$-$C_3$ alkyl group, an optionally substituted 5 or 6 membered heteroaryl group, or an optionally substituted phenyl group.

22. A method for the treatment of cancer which comprises administering to a subject in need thereof a compound of formula (I) according to claim 1, or a pharmaceutically acceptable salt or solvate thereof, wherein the cancer is selected from the group consisting of breast cancer, chronic myelogenous (or myeloid) leukemia (CML), colorectal cancer, fibrosarcoma, gastric cancer, glioblastoma, kidney cancer, liver cancer, lung cancer, melanoma, nasopharyngeal cancer, oral cancer, orthotopic multiple myeloma, osteosarcoma, ovarian cancer, pancreatic cancer, and prostate cancer.

23. The process of claim 7, further comprising reacting the obtained compound of formula (IV) with a mixture of hydroxylamine hydrochloride and phenolphthalein in the presence of an excess of sodium methoxide in methanol to prepare a compound of general formula (Ia):

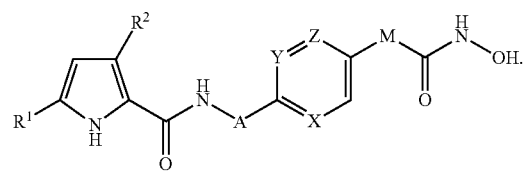

(Ia)

* * * * *

UNITED STATES PATENT AND TRADEMARK OFFICE
CERTIFICATE OF CORRECTION

PATENT NO. : 8,685,992 B2
APPLICATION NO. : 13/499839
DATED : April 1, 2014
INVENTOR(S) : Cossío Mora et al.

It is certified that error appears in the above-identified patent and that said Letters Patent is hereby corrected as shown below:

On the title page item (75), line 4, Inventor: change "Yosu Vara Zalazar" to -- Yosu Ion Vara Salazar --

On the title page item (75), lines 5-6, Inventor: change "Eider Ion San Sebastián Larzabal" to -- Eider San Sebastián Larzabal --

On the title page item (73), line 2, Assignee: change "Ikerschem, S.L." to -- Ikerchem, S.L. --

In the Claims:

Column 59, Line 14: change "[23] N-(4-{[(2-Aminophenyl)amino)carbonyl]benzyl}-5-" to
-- [23] N-(4-{[(2-Aminophenyl)amino]carbonyl]benzyl}-5- --

Column 59, Line 32: change "[24] N-(4-{[(2-Aminophenyl)amino)carbonyl]benzyl}-5-" to
-- [24] N-(4-{[(2-Aminophenyl)amino]carbonyl]benzyl}-5- --

Column 59, Line 49: change "[25] N-(4-{[(2-Aminophenyl)amino)carbonyl]benzyl}-5-" to
-- [25] N-(4-{[(2-Aminophenyl)amino]carbonyl]benzyl}-5- --

Column 59, Line 65: change "[26] N-(4-{[(2-Aminophenyl)amino)carbonyl]benzyl}-3-" to
-- [26] N-(4-{[(2-Aminophenyl)amino]carbonyl]benzyl}-3- --

Column 60, Line 14: change "[27] N-(4-{[(2-Aminophenyl)amino)carbonyl]benzyl}-3-" to
-- [27] N-(4-{[(2-Aminophenyl)amino]carbonyl]benzyl}-3- --

Signed and Sealed this
Sixteenth Day of September, 2014

Michelle K. Lee
*Deputy Director of the United States Patent and Trademark Office*